(12) United States Patent
Schrauder et al.

(10) Patent No.: US 11,083,882 B2
(45) Date of Patent: Aug. 10, 2021

(54) SYRINGE AND CONNECTOR SYSTEM

(71) Applicant: BAYER HEALTHCARE LLC, Whippany, NJ (US)

(72) Inventors: Matthew Schrauder, Mars, PA (US); Brian Cain, Elizabeth, PA (US); Michael Cousley, Gibsonia, PA (US); Kevin Cowan, Allison Park, PA (US); Michael Spohn, Fenelton, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 236 days.

(21) Appl. No.: 15/778,367

(22) PCT Filed: Nov. 23, 2016

(86) PCT No.: PCT/US2016/063448
§ 371 (c)(1),
(2) Date: May 23, 2018

(87) PCT Pub. No.: WO2017/091635
PCT Pub. Date: Jun. 1, 2017

(65) Prior Publication Data
US 2018/0339146 A1 Nov. 29, 2018

Related U.S. Application Data

(60) Provisional application No. 62/259,891, filed on Nov. 25, 2015.

(51) Int. Cl.
*A61M 39/10* (2006.01)
*A61M 5/28* (2006.01)

(52) U.S. Cl.
CPC ........ *A61M 39/1011* (2013.01); *A61M 5/281* (2013.01); *A61M 2039/1044* (2013.01);
(Continued)

(58) Field of Classification Search
CPC .. A61M 2039/1044; A61M 2039/1061; A61M 2039/1077; A61M 39/1011;
(Continued)

(56) References Cited

U.S. PATENT DOCUMENTS 798,093 A 8/1905 Edward
817,054 A 4/1906 Daniel
(Continued)

FOREIGN PATENT DOCUMENTS

EP 2005934 A2 12/2008
EP 2719420 A1 4/2014
(Continued)

OTHER PUBLICATIONS

International Preliminary Report on Patentability and Written Opinion dated Sep. 24, 2015 from corresponding PCT Application No. PCT/US2014/022629.
(Continued)

*Primary Examiner* — Jason E Flick
(74) *Attorney, Agent, or Firm* — Joseph L. Kent; David Schramm; James R. Stevenson

(57) ABSTRACT

A connector assembly may include a body and a fluid fitting, the fluid fitting configured for releasably engaging a syringe nozzle, at least one deflectable locking arm connected to the body and radially deflectable relative to the distal end, the proximal end of the at least one deflectable locking arm configured for deflecting in a radial direction relative to the distal end to releasably engage the syringe nozzle, and at least one locking element disposed on the at least one deflectable locking arm, the at least one locking element movable with movement of the at least one deflectable locking arm between a first position where the at least one locking element is released from an engagement portion of the syringe nozzle and a second position where the at least
(Continued)

one locking element is engaged with the engagement portion of the syringe nozzle.

20 Claims, 42 Drawing Sheets

(52) U.S. Cl.
CPC .............. *A61M 2039/1061* (2013.01); *A61M 2039/1077* (2013.01)

(58) Field of Classification Search
CPC ...... A61M 5/281; A61M 39/00; A61M 39/10; A61M 2039/1027; A61M 5/178
See application file for complete search history.

(56) References Cited

U.S. PATENT DOCUMENTS

| | | |
|---|---|---|
| 1,388,946 A | 8/1921 | Goold |
| 2,514,575 A | 7/1950 | Hein et al. |
| 2,616,422 A | 11/1952 | Jones |
| 2,672,866 A | 3/1954 | Kater |
| 2,690,179 A | 9/1954 | Fox |
| 2,915,986 A | 12/1959 | Sisson |
| 3,101,712 A | 8/1963 | Strazdins |
| 3,166,070 A | 1/1965 | Everett |
| 3,199,511 A | 8/1965 | Kulick |
| 3,412,906 A | 11/1968 | Dinger |
| 3,507,278 A | 4/1970 | Winfried |
| 3,527,215 A | 9/1970 | Harry |
| 3,699,961 A | 10/1972 | Roman |
| 3,736,932 A | 6/1973 | Satchell |
| 3,785,367 A | 1/1974 | Fortin et al. |
| 3,998,223 A | 12/1976 | Dawe |
| 4,041,944 A | 8/1977 | Rhodes |
| 4,131,217 A | 12/1978 | Sandegren |
| 4,140,117 A | 2/1979 | Buckles et al. |
| 4,236,516 A | 12/1980 | Nilson |
| 4,245,655 A | 1/1981 | Patel |
| 4,312,344 A | 1/1982 | Nilson |
| 4,318,400 A | 3/1982 | Peery et al. |
| 4,325,369 A | 4/1982 | Nilson |
| 4,419,096 A | 12/1983 | Leeper et al. |
| 4,438,845 A | 3/1984 | Mochow |
| 4,444,310 A | 4/1984 | Odell |
| 4,741,733 A | 5/1988 | Winchell et al. |
| 4,747,839 A | 5/1988 | Tarello et al. |
| 4,824,145 A | 4/1989 | Carlsson |
| 4,895,570 A | 1/1990 | Larkin |
| 4,904,239 A | 2/1990 | Winchell et al. |
| 5,011,477 A | 4/1991 | Winchell et al. |
| 5,033,631 A | 7/1991 | Nightingale |
| 5,048,684 A | 9/1991 | Scott |
| 5,120,315 A | 6/1992 | Hessel |
| 5,147,311 A | 9/1992 | Pickhard |
| 5,178,610 A | 1/1993 | Tsujikawa et al. |
| 5,192,272 A | 3/1993 | Faure |
| 5,199,567 A | 4/1993 | Discko, Jr. |
| 5,237,309 A | 8/1993 | Frantz et al. |
| 5,238,003 A | 8/1993 | Baidwan et al. |
| 5,263,940 A | 11/1993 | Kriesel |
| 5,312,018 A | 5/1994 | Evezich |
| 5,316,452 A | 5/1994 | Bogen et al. |
| 5,318,540 A | 6/1994 | Athayde et al. |
| 5,342,313 A | 8/1994 | Campbell et al. |
| 5,383,858 A | 1/1995 | Reilly et al. |
| 5,399,173 A | 3/1995 | Parks et al. |
| 5,492,147 A | 2/1996 | Challender et al. |
| 5,520,653 A | 5/1996 | Reilly et al. |
| 5,578,005 A | 11/1996 | Sancoff et al. |
| 5,683,369 A | 11/1997 | Tsukada |
| 5,827,233 A | 10/1998 | Futagawa et al. |
| 5,873,861 A | 2/1999 | Hitchins et al. |
| 5,893,843 A | 4/1999 | Rodrigues Claro |
| 5,899,889 A | 5/1999 | Futagawa et al. |
| 5,957,898 A | 9/1999 | Jepson et al. |
| 5,976,112 A | 11/1999 | Lyza, Jr. |
| 5,980,489 A | 11/1999 | Kriesel |
| 6,056,724 A | 5/2000 | Lacroix |
| 6,063,058 A | 5/2000 | Sakamoto |
| 6,077,252 A | 6/2000 | Siegel |
| 6,142,976 A | 11/2000 | Kubo |
| 6,270,482 B1 | 8/2001 | Rosoff et al. |
| 6,319,235 B1 | 11/2001 | Yoshino |
| 6,322,542 B1 | 11/2001 | Nilson et al. |
| 6,328,715 B1 | 12/2001 | Dragan et al. |
| 6,450,993 B1 | 9/2002 | Lin |
| 6,465,024 B1 | 10/2002 | Di Scala et al. |
| 6,485,471 B1 | 11/2002 | Zivitz et al. |
| 6,497,684 B2 | 12/2002 | Witowski et al. |
| 6,578,738 B1 | 6/2003 | Keller |
| 6,620,134 B1 | 9/2003 | Trombley, III et al. |
| 6,652,489 B2 | 11/2003 | Trocki et al. |
| 6,723,074 B1 | 4/2004 | Halseth |
| 6,726,657 B1 | 4/2004 | Dedig et al. |
| 6,855,130 B2 | 2/2005 | Saulenas et al. |
| 6,869,419 B2 | 3/2005 | Dragan et al. |
| 7,011,650 B2 | 3/2006 | Rosoff et al. |
| 7,094,216 B2 | 8/2006 | Trombley et al. |
| 7,240,926 B2 | 7/2007 | Dalle et al. |
| 7,419,478 B1 | 9/2008 | Reilly et al. |
| 7,462,166 B2 | 12/2008 | Kowan et al. |
| 7,497,843 B1 | 3/2009 | Castillo et al. |
| 7,540,856 B2 | 6/2009 | Hitchins |
| 7,556,619 B2 | 7/2009 | Spohn et al. |
| 7,581,559 B2 | 9/2009 | Bausmith, III |
| 7,597,683 B2 | 10/2009 | Myhrberg et al. |
| 7,621,395 B2 | 11/2009 | Mogensen et al. |
| 7,686,788 B2 | 3/2010 | Freyman et al. |
| 8,147,464 B2 | 4/2012 | Spohn et al. |
| 8,337,456 B2 | 12/2012 | Schriver et al. |
| 8,795,240 B2 | 8/2014 | Chelak |
| 9,498,570 B2 | 11/2016 | Cowan et al. |
| 2001/0018575 A1 | 8/2001 | Lyza |
| 2002/0147429 A1* | 10/2002 | Cowan ............... A61M 39/1011 604/187 |
| 2003/0216695 A1 | 11/2003 | Yang |
| 2004/0064041 A1 | 4/2004 | Lazzaro et al. |
| 2004/0068224 A1 | 4/2004 | Couvillon et al. |
| 2004/0254541 A1* | 12/2004 | Wong .................... A61M 5/158 604/239 |
| 2005/0113754 A1 | 5/2005 | Cowan et al. |
| 2005/0225082 A1 | 10/2005 | Dalle et al. |
| 2006/0200083 A1 | 9/2006 | Freyman et al. |
| 2007/0129705 A1 | 6/2007 | Trombley, III |
| 2008/0086087 A1 | 4/2008 | Spohn et al. |
| 2009/0069792 A1 | 3/2009 | Frey et al. |
| 2009/0216192 A1 | 8/2009 | Schriver et al. |
| 2009/0218243 A1 | 9/2009 | Gyrn et al. |
| 2010/0089475 A1 | 4/2010 | Tracey |
| 2012/0123257 A1 | 5/2012 | Stokes, Jr. et al. |
| 2012/0209111 A1 | 8/2012 | Cowan et al. |
| 2014/0276652 A1 | 9/2014 | Gittard et al. |

FOREIGN PATENT DOCUMENTS

| | | |
|---|---|---|
| JP | H02-88664 | 7/1990 |
| WO | 9528195 A1 | 10/1995 |
| WO | 02066100 A2 | 8/2002 |
| WO | 2004033023 A1 | 4/2004 |
| WO | 2013043868 A1 | 3/2013 |
| WO | 2013043881 A1 | 3/2013 |
| WO | 2013043889 A1 | 3/2013 |
| WO | 2015164783 A1 | 10/2015 |
| WO | 2016172467 A1 | 10/2016 |
| WO | 2017091643 A1 | 6/2017 |

OTHER PUBLICATIONS

International Search Report and Written Opinion dated Jul. 30, 2014 from corresponding PCT Application No. PCT/US2014/022629.
"International Search Report and Written Opinion from PCT Application No. PCT/US2016/063448", dated Feb. 24, 2017.

(56) References Cited

OTHER PUBLICATIONS

"Supplementary European Search Report from EP 14770001", dated Nov. 25, 2016.

* cited by examiner

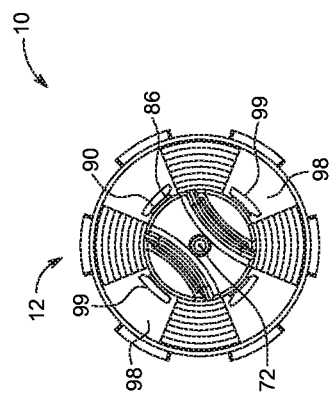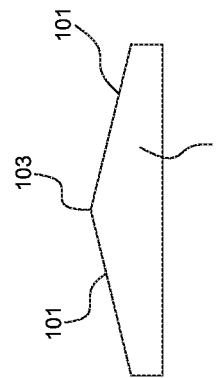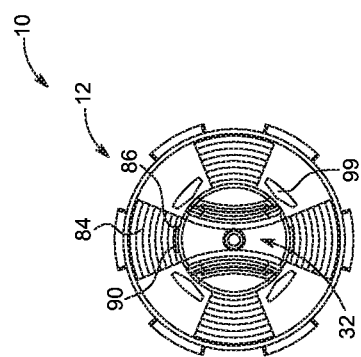

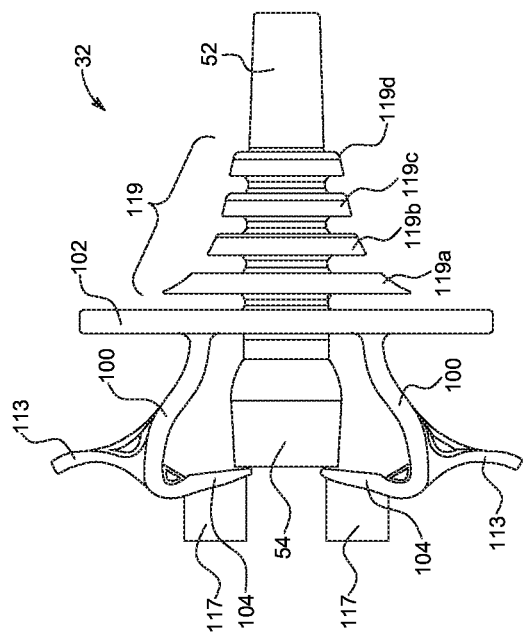
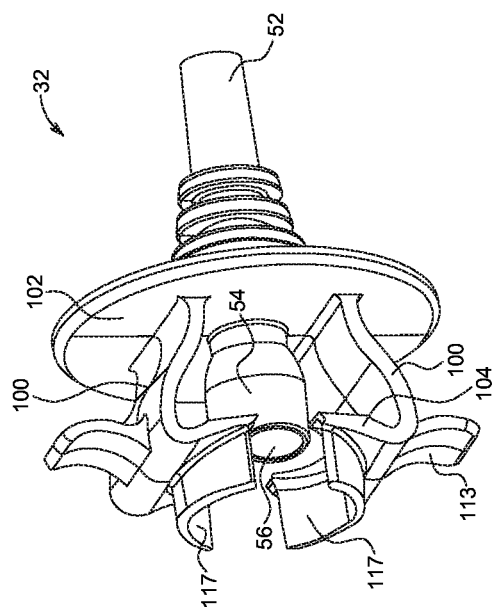
FIG. 43A
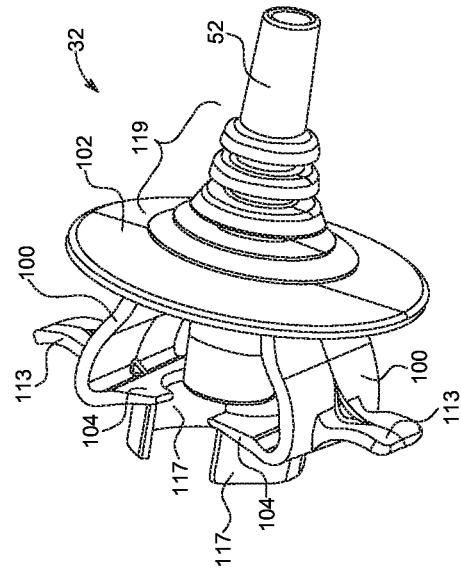
FIG. 43B
FIG. 43C

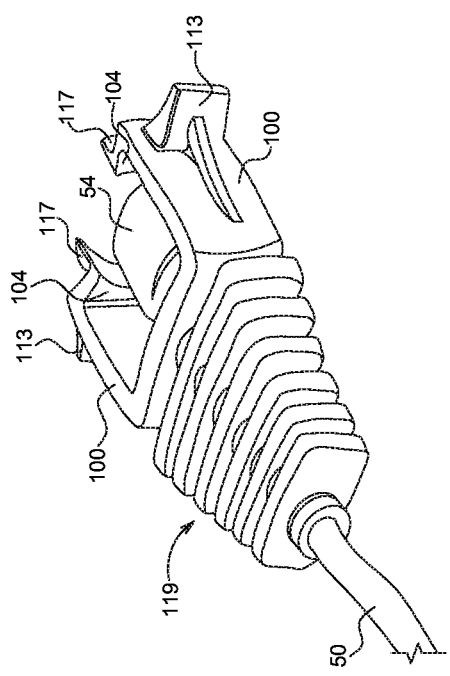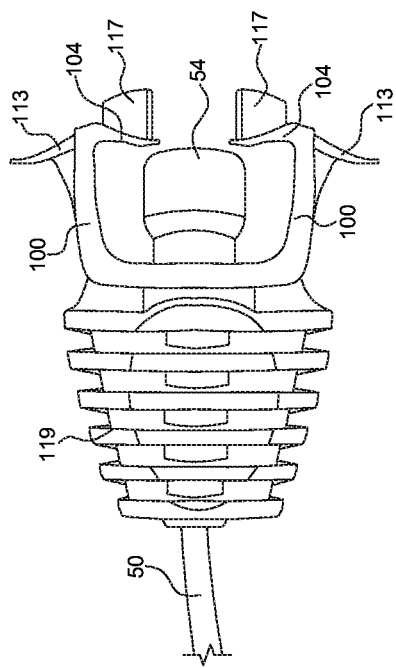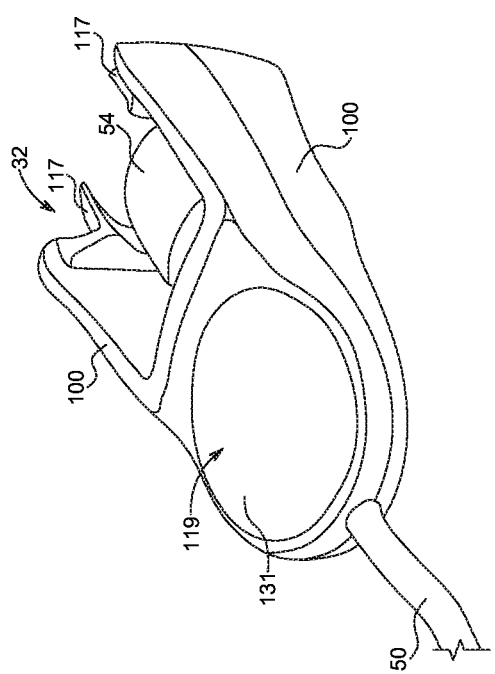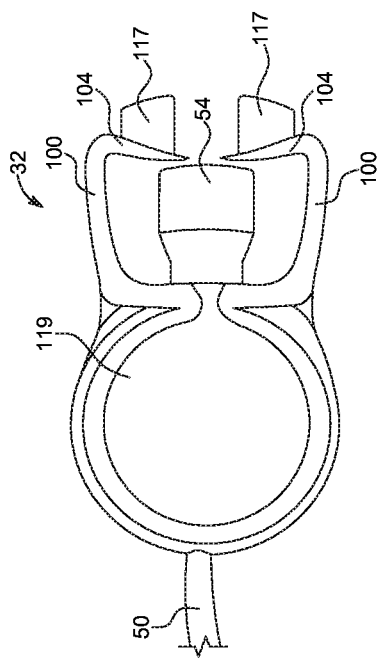
FIG. 54A
FIG. 54B
FIG. 53A
FIG. 53B

SYRINGE AND CONNECTOR SYSTEM

CROSS REFERENCE TO RELATED APPLICATIONS

This application is a 371 national phase application of PCT International Application No. PCT/US2016/063448, filed Nov. 23, 2016, and claims the benefit of U.S. Provisional Patent Application Nos. 62/259,891 filed Nov. 25, 2015, the disclosures of each of which is hereby incorporated by reference in their entirety.

BACKGROUND OF THE DISCLOSURE

Field of the Disclosure

The present disclosure relates to syringes, connectors, and syringe and connector systems for use in fluid delivery systems, and, especially, to syringes, connectors, and syringe and connector systems for use in medical fluid delivery systems in which one or more fluids are delivered to a patient.

Description of the Related Art

In many medical diagnostic and therapeutic procedures, it is desirable to inject a medical fluid into a patient. In some medical procedures, for example, computed tomography (CT), angiography, and magnetic resonance imaging (MRI), it is desirable to deliver one or more medical fluids, such as a contrast solution (often referred to simply as "contrast") and a flushing agent (such as saline), in a timed fashion under pressure. Relatively high pressures and timed boluses are typically achieved through the use of fluid delivery systems having one or more powered injectors.

In many of such fluid delivery systems, it is necessary to form a fluid connection between separate fluid path components. For example, it may be necessary to connect one or more injector-driven syringes to flexible tubing that, in turn, is connected to a patient. A common fluid connector used in the medical arts for connecting the syringe to tubing is a luer connector or luer lock. FIG. 1 illustrates a common design of a luer connector 200 in accordance with a prior art aspect. The luer connector 200 includes a male connector or member 202 and a female connector or member 204. The male member 202 includes a conduit 206 having a taper on an outside wall thereof angled at approximately 6 degrees relative to a longitudinal axis 216 of the luer connector 200. The female member 204 includes a conduit or fitting 208 therein having a taper of approximately 6 degrees to form a mating fit with the outside wall of the conduit or fitting 206 of the male member 202. The male member 202 and female member 204 are typically connected via radially inwardly protruding threading 210 on the male member 202 which cooperates with one or more radially outwardly protruding flanges 212 and 214 on female luer member 204 to create a sealed connection between the male member 202 and female member 204. In general, luer fittings create a sealed connection via an "interference fit," which refers generally to cooperating fittings in which the internal member or fitting is slightly larger than the external member or fitting and has to be forced inside the external member or fitting. In the case of a tapered fitting such as a luer fitting, the interference fit is created upon application of an axial compressive force to the cooperating/mating fittings.

Many fluid connectors for use in medical procedures, including luer connectors, exhibit drawbacks, not the least of which include fragility, breakability (for example, from over tightening), and difficulty in forming a connection, for example by having to rotate one or both connectors. Because medical personnel are under increasingly difficult time and physical constraints during various medical procedures, quite often, many fluid path elements must be connected and/or disconnected in a relatively short time under stressed and/or emergency conditions. Additionally, the seal between the male member 202 and the female member 204 may be compromised due to tolerance stacking between the male member 202 and the female member 204 due to variances in the manufacturing process.

It is thus very desirable to develop syringes, connectors, and syringe and connector systems that are durable, connect and disconnect simply and quickly, and yet provide a reliable fluid path connection.

SUMMARY OF THE DISCLOSURE

In general, the present disclosure provides syringes, connectors, adapters, and systems and methods of connection for use in medical fluid delivery systems in which many of the problems associated with prior fluid path connections are eliminated. The connectors of the present disclosure are suitable for use both at low pressures and at the relatively high pressures used in powered injection procedures (for example, pressures of 300 psi and above). In general, the connectors of the present disclosure can be connected with one hand. With many of the connectors of the present disclosure, rotation is not required to form an adequate seal. In those connectors of the present disclosure in which rotation is desirable, such rotation is generally no more than approximately ½ turn (or 180°), and more preferably, no more than approximately ¼ turn (or 90°). In several aspects, the connectors of the present disclosure prevent over tightening and the damage associated therewith. Further, connectors of the present disclosure can be fabricated to be generally open or non-enclosing so that fluid paths near the connectors are readily visible to the operator.

In accordance with one aspect, a connector assembly may include a body having a proximal end and a distal end spaced apart along a longitudinal axis and a fluid fitting at the proximal end of the body, the fluid fitting configured for releasably engaging a syringe nozzle, a passageway defined by and extending through the body with the fluid fitting provided at a proximal end of the body for releasably engaging the syringe nozzle, at least one deflectable locking arm having a distal end connected to the body and a proximal end radially deflectable relative to the distal end, the proximal end of the at least one deflectable locking arm configured for deflecting in a radial direction relative to the distal end to releasably engage the syringe nozzle, and at least one locking element disposed on at least a portion of the at least one deflectable locking arm, the at least one locking element movable with movement of the at least one deflectable locking arm between a first position where the at least one locking element is released from an engagement portion of the syringe nozzle and a second position where the at least one locking element is engaged with the engagement portion of the syringe nozzle.

In accordance with further aspects, at least one releasing tab may be provided on the at least one deflectable locking arm to assist in deflecting the proximal end of the at least one deflectable locking arm in the radial direction relative to the distal end of the at least one deflectable locking arm. At least one gripping tab may be provided on the body for gripping the connector assembly. The at least one deflectable locking arm may include two deflectable locking arms provided on opposing sides of the longitudinal axis of the body. The deflectable locking arms may be movable apart from one another to move the at least one locking element of each deflectable locking arm radially outward relative to the longitudinal axis of the body. A protective skirt may be provided at the proximal end of the at least one deflectable locking arm. The protective skirt may be shaped to surround at least a portion of the syringe nozzle when the connector assembly is connected to the syringe nozzle. An opposing fitting may be provided at the distal end of the body for releasably engaging tubing. The at least one deflectable locking arm may be deflected radially outward upon pressing the connector assembly against the syringe nozzle. A piercing member may extend from a distal end of the body and in fluid communication with the passageway. A tubing manifold may be provided on a distal end of the connector assembly. The at least one deflectable locking arm may disengage the engagement portion of the syringe nozzle by rotation of the connector assembly about the longitudinal axis of the syringe.

In accordance with another aspect, a syringe and connector system for use in a medical injection procedure is disclosed, the syringe and connector system may include a syringe having a proximal end and a distal end with a syringe nozzle on the distal end, and a connector assembly configured for releasably engaging the syringe nozzle, the connector assembly may include a body having a proximal end and a distal end spaced apart along a longitudinal axis and a fluid fitting at the proximal end of the body, the fluid fitting configured for releasably engaging the syringe nozzle, a passageway defined by and extending through the body with the fluid fitting provided at a proximal end of the body for releasably engaging the syringe nozzle, at least one deflectable locking arm having a distal end connected to the body and a proximal end radially deflectable relative to the distal end, the proximal end of the at least one deflectable locking arm configured for deflecting in a radial direction relative to the distal end to releasably engage the syringe nozzle, and at least one locking element disposed on at least a portion of the at least one deflectable locking arm, the at least one locking element movable with movement of the at least one deflectable locking arm between a first position where the at least one locking element is released from an engagement portion of the syringe nozzle and a second position where the at least one locking element is engaged with the engagement portion of the syringe nozzle.

In accordance with further aspects, at least one releasing tab may be provided on the at least one deflectable locking arm to assist in deflecting the proximal end of the at least one deflectable locking arm in the radial direction relative to the distal end. At least one gripping tab may be provided on the body for gripping the connector assembly. The at least one deflectable locking arm may include two deflectable locking arms provided on opposing sides of the longitudinal axis of the body. The deflectable locking arms may be movable apart from one another to move the at least one locking element of each deflectable locking arm radially outward relative to the longitudinal axis of the body. A protective skirt may be provided on at the proximal end of the at least one deflectable locking arm. The protective skirt may be shaped to surround at least a portion of the syringe nozzle when the connector assembly is connected to the syringe nozzle. An opposing fitting may be provided at the distal end of the body for releasably engaging tubing. The at least one deflectable locking arm may be deflected radially outward upon pressing the connector assembly against the syringe nozzle. The syringe nozzle may include an inner member having a fluid channel in fluid communication with an interior of the syringe, an outer annular skirt spaced apart from the inner member by an annular space, and an engagement portion on a radially outer surface of the outer annular skirt. A tubing manifold may be provided on a distal end of the connector assembly. The at least one deflectable locking arm may disengage the engagement portion of the syringe nozzle by rotation of the connector assembly about the longitudinal axis of the syringe.

Further aspects will now be described in the following numbered clauses.

Clause 1: A connector assembly comprising: a body having a proximal end and a distal end spaced apart along a longitudinal axis and a fluid fitting at the proximal end of the body, the fluid fitting configured for releasably engaging a syringe nozzle, a passageway defined by and extending through the body with the fluid fitting provided at a proximal end of the body for releasably engaging the syringe nozzle, at least one deflectable locking arm having a distal end connected to the body and a proximal end radially deflectable relative to the distal end, the proximal end of the at least one deflectable locking arm configured for deflecting in a radial direction relative to the distal end to releasably engage the syringe nozzle, and at least one locking element disposed on at least a portion of the at least one deflectable locking arm, the at least one locking element movable with movement of the at least one deflectable locking arm between a first position where the at least one locking element is released from an engagement portion of the syringe nozzle and a second position where the at least one locking element is engaged with the engagement portion of the syringe nozzle.

Clause 2: The connector assembly of clause 1, further comprising at least one releasing tab provided on the at least one deflectable locking arm to assist in deflecting the proximal end of the at least one deflectable locking arm in the radial direction relative to the distal end of the at least one deflectable locking arm.

Clause 3: The connector assembly of either clause 1 or clause 2, further comprising at least one gripping tab provided on the body for gripping the connector assembly.

Clause 4: The connector assembly of any of clauses 1-3, wherein the at least one deflectable locking arm comprises two deflectable locking arms provided on opposing sides of the longitudinal axis of the body, and wherein the deflectable locking arms are movable apart from one another to move the at least one locking element of each deflectable locking arm radially outward relative to the longitudinal axis of the body.

Clause 5: The connector assembly of any of clauses 1-4, further comprising a protective skirt provided at the proximal end of the at least one deflectable locking arm, wherein the protective skirt is shaped to surround at least a portion of the syringe nozzle when the connector assembly is connected to the syringe nozzle.

Clause 6: The connector assembly of any of clause 1-5, further comprising an opposing fitting provided at the distal end of the body for releasably engaging tubing.

Clause 7: The connector assembly of any of clauses 1-6, wherein the at least one deflectable locking arm is deflected radially outward upon pressing the connector assembly against the syringe nozzle.

Clause 8: The connector assembly of any of clauses 1-7, further comprising a piercing member extending from a distal end of the body and in fluid communication with the passageway.

Clause 9: The connector assembly of any of clauses 1-8, further comprising a tubing manifold provided on a distal end of the connector assembly.

Clause 10: The connector assembly of any of clauses 1-9, wherein the at least one deflectable locking arm disengages the engagement portion of the syringe nozzle by rotation of the connector assembly about the longitudinal axis of the syringe.

Clause 11: A syringe and connector system for use in a medical injection procedure, the syringe and connector system comprising: a syringe having a proximal end and a distal end with a syringe nozzle on the distal end, and a connector assembly configured for releasably engaging the syringe nozzle, the connector assembly comprising: a body having a proximal end and a distal end spaced apparat along a longitudinal axis and a fluid fitting at the proximal end of the body, the fluid fitting configured for releasably engaging the syringe nozzle, a passageway defined by and extending through the body with the fluid fitting provided at a proximal end of the body for releasably engaging the syringe nozzle, at least one deflectable locking arm having a distal end connected to the body and a proximal end radially deflectable relative to the distal end, the proximal end of the at least one deflectable locking arm configured for deflecting in a radial direction relative to the distal end to releasably engage the syringe nozzle, and at least one locking element disposed on at least a portion of the at least one deflectable locking arm, the at least one locking element movable with movement of the at least one deflectable locking arm between a first position where the at least one locking element is released from an engagement portion of the syringe nozzle and a second position where the at least one locking element is engaged with the engagement portion of the syringe nozzle.

Clause 12: The syringe and connector system of clause 11, further comprising at least one releasing tab provided on the at least one deflectable locking arm to assist in deflecting the proximal end of the at least one deflectable locking arm in the radial direction relative to the distal end.

Clause 13: The syringe and connector system of either clause 11 or clause 12, further comprising at least one gripping tab provided on the body for gripping the connector assembly.

Clause 14: The syringe and connector system of any of clauses 11-13, wherein the at least one deflectable locking arm comprises two deflectable locking arms provided on opposing sides of the longitudinal axis of the body, and wherein the deflectable locking arms are movable apart from one another to move the at least one locking element of each deflectable locking arm radially outward relative to the longitudinal axis of the body.

Clause 15: The syringe and connector system of any of clauses 11-14, further comprising a protective skirt provided on at the proximal end of the at least one deflectable locking arm, wherein the protective skirt is shaped to surround at least a portion of the syringe nozzle when the connector assembly is connected to the syringe nozzle.

Clause 16: The syringe and connector system of any of clauses 11-15, further comprising an opposing fitting provided at the distal end of the body for releasably engaging tubing.

Clause 17: The syringe and connector system of any of clauses 11-16, wherein the at least one deflectable locking arm is deflected radially outward upon pressing the connector assembly against the syringe nozzle.

Clause 18: The syringe and connector system of any of clauses 11-17, wherein the syringe nozzle comprises: an inner member having a fluid channel in fluid communication with an interior of the syringe, an outer annular skirt spaced apart from the inner member by an annular space, and an engagement portion on a radially outer surface of the outer annular skirt.

Clause 19: The syringe and connector system of any of clauses 11-18, further comprising a tubing manifold provided on a distal end of the connector assembly.

Clause 20: The syringe and connector system of any of clauses 11-19, wherein the at least one deflectable locking arm disengages the engagement portion of the syringe nozzle by rotation of the connector assembly about the longitudinal axis of the syringe.

These and other features and characteristics of the syringes, connectors for syringes, adapters, and systems and methods of connection for use in medical fluid delivery systems, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only, and are not intended as a definition of the limits of the disclosure. As used in the specification and the claims, the singular form of "a", "an", and "the" include plural referents unless the context clearly dictates otherwise.

BRIEF DESCRIPTION OF THE DRAWINGS

FIG. 20 is a top view of the syringe and connector assembly shown in FIG. 15.

FIG. 21A is a top view of the syringe and connector assembly shown in FIG. 16.

FIG. 21B is a top view of a release rib shown in FIG. 21A.

FIG. 43A is a rear perspective view of a connector assembly in accordance with another aspect.

FIG. 43B is a front perspective view of a connector assembly shown in FIG. 43A.

FIG. 43C is a side view of the connector assembly shown in FIG. 43A.

FIG. 53A is a perspective view of a connector assembly in accordance with another aspect.

FIG. 53B is a side view of the connector assembly shown in FIG. 53A.

FIG. 54A is a perspective view of a connector assembly in accordance with another aspect.

FIG. 54B is a side view of the connector assembly shown in FIG. 54A.

DETAILED DESCRIPTION OF THE DISCLOSURE

Figure 2:
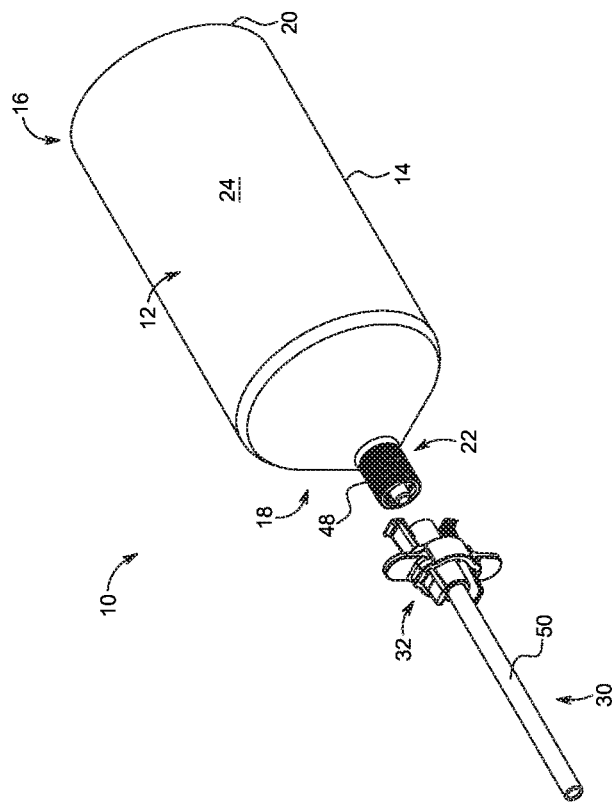
FIG. 2 is an exploded perspective view of a syringe and a connector assembly in accordance with one aspect.
Figure 1:
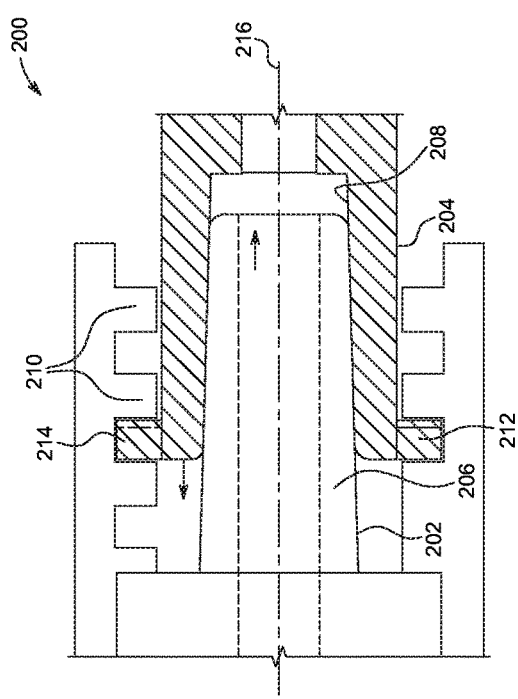
FIG. 1 is a side, cross-sectional view of a standard luer connection in accordance with a prior art aspect.
Figure 4:
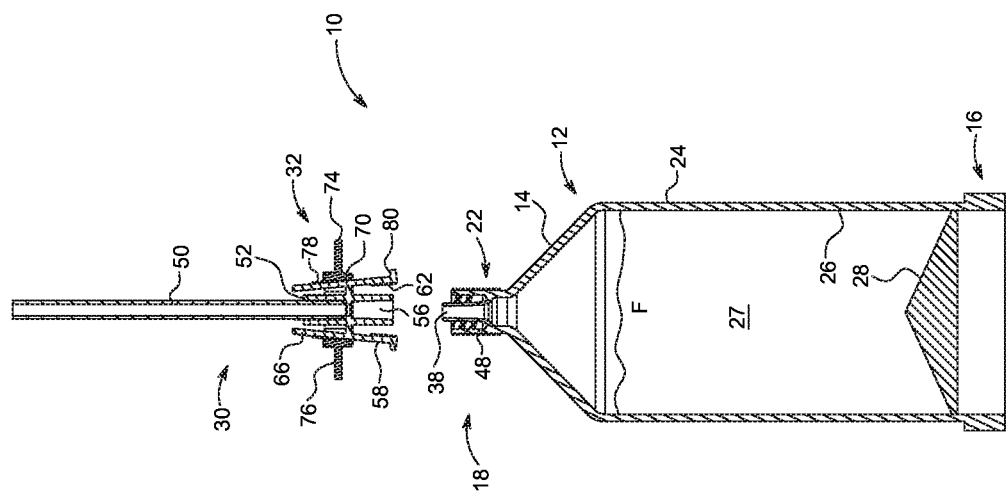
FIG. 4 is an exploded, side, cross-sectional view of the syringe and connector assembly shown in FIG. 2.

The illustrations generally show preferred and non-limiting aspects of the systems and methods of the present disclosure. While the description presents various aspects of the devices, it should not be interpreted in any way as limiting the disclosure. Furthermore, modifications, concepts, and applications of the disclosure's aspects are to be interpreted by those skilled in the art as being encompassed, but not limited to, the illustrations and description provided herein.

The following description is provided to enable those skilled in the art to make and use the described aspects contemplated for carrying out the disclosure. Various modifications, equivalents, variations, and alternatives, however, will remain readily apparent to those skilled in the art. Any and all such modifications, variations, equivalents, and alternatives are intended to fall within the spirit and scope of the present disclosure. Further, for purposes of the description hereinafter, the terms "end", "upper", "lower", "right", "left", "vertical", "horizontal", "top", "bottom", "lateral", "longitudinal", and derivatives thereof shall relate to the disclosure as it is oriented in the figures. The term "proximal" refers generally to an axial or a longitudinal direction toward the end of a syringe nearest the injector and opposite the tubing towards the patient. The term "distal" refers generally to an axial or a longitudinal direction away from the injector and towards the patient. The term "radial" and related terms refers generally to a direction normal to a longitudinal axis of a syringe. However, it is to be understood that the disclosure may assume various alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the aspects disclosed herein are not to be considered as limiting.

Referring to the drawings in which like reference characters refer to like parts throughout the several views thereof, syringes, connector assemblies, adapters, and systems and methods of connection for use in medical fluid delivery systems will be described herein in detail. The present disclosure also provides other connectors suitable for use with the syringes of the present disclosure as well as with other fluid path elements or fluid pumping systems. In general, the connectors of the present disclosure are suitable for use in low pressure and high-pressure procedures. In that regard, pressures in injection procedures, such as contrast enhanced CT scans, can exceed approximately 300 psi, while pressures in angiographic procedures can exceed approximately 1200 psi.

With reference to FIGS. 2-12, a syringe and connector assembly 10 is illustrated in accordance with one aspect. With specific reference to FIGS. 2-5, a syringe 12 has a generally cylindrical syringe barrel 14 formed from glass or a suitable medical-grade plastic. In some aspects, the syringe 12 may be configured for use with a powered fluid injector. The barrel 14 has a proximal end 16 and a distal end 18, with a sidewall 20 extending therebetween. A fluid delivery section, such as a nozzle 22, extends from the distal end 18 of the barrel 14. The barrel 14 has an outer surface 24 and an inner surface 26 (shown in FIG. 4) that define an interior volume 27 (shown in FIG. 4) configured for receiving a fluid F (shown in FIG. 4) therein. The proximal end 16 of the barrel 14 may be sealed with a plunger 28 (shown in FIG. 4) that is reversibly slideable through the barrel 14. In other embodiments, the barrel may be a rolling diaphragm where the proximal end is sealed. The plunger 28 forms a liquid-tight seal against the inner surface 26 of the barrel 14 as the plunger 28 is advanced or withdrawn through the barrel 14.

With continued reference to FIGS. 2-5, the distal end 18 of the syringe 12 may have a nozzle 22 that is configured for releasable fluid connection with a fluid path set 30 that may be connected to the patient. In some aspects, the fluid path set 30 may be in the form of tubing configured for delivering fluid from the syringe 12 to the patient or a container for receiving the fluid. A connector assembly 32 is formed on a proximal end of the fluid path set 30 and is configured for connecting the fluid path set 30 to the nozzle 22 of the syringe 12. The proximal end 16 of the syringe 12 is sized and adapted to be inserted in a syringe port of an injector (not shown). In certain aspects, the proximal end 16 of the syringe 12 may include one or more syringe retaining members configured for releasable engagement with the syringe port of the injector.

Figure 5:
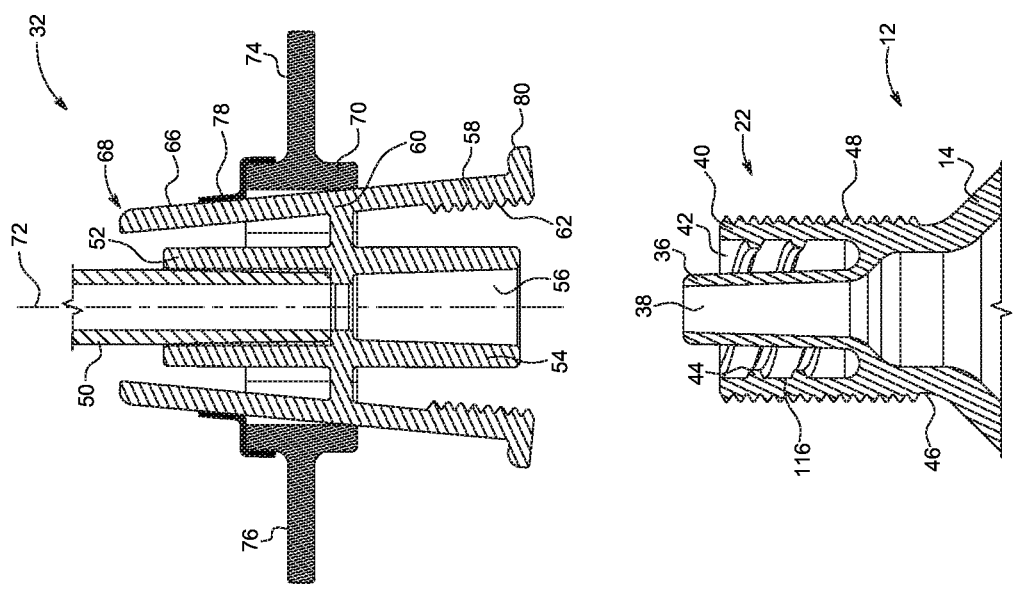
FIG. 5 is a detailed, side, cross-sectional view of the syringe nozzle and the connector assembly shown in FIG. 3.
Figure 8:
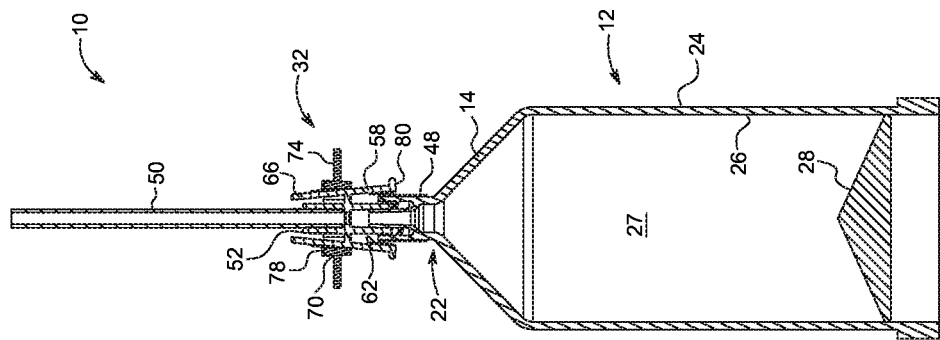
FIG. 8 is a side, cross-sectional view of the syringe and connector assembly shown in FIG. 6.
Figure 7:
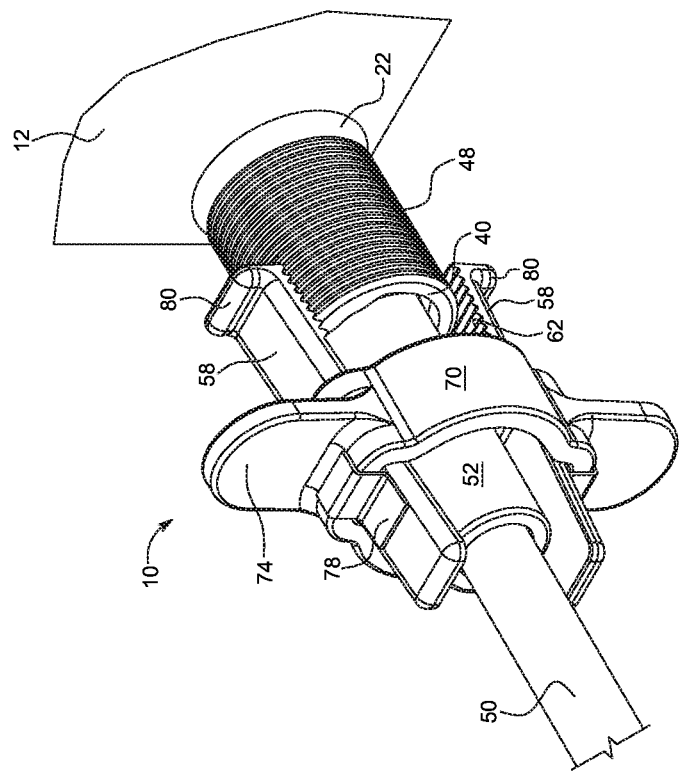
FIG. 7 is a detailed perspective view of the syringe nozzle and the connector assembly shown in FIG. 6.

With specific reference to FIG. 5, the nozzle 22 of the syringe 12 has an inner member 36 that tapers inwardly from the proximal end 16 to the distal end 18 of the syringe 12. The inner member 36 defines a fluid channel 38 that is in fluid communication with the interior volume 27 of the syringe 12. The inner member 36 is surrounded by an outer annular skirt 40 that extends axially along at least a portion of the longitudinal length of the inner member 36. The inner member 36 is spaced apart radially from the outer annular skirt 40 by an annular space 42. The outer annular skirt 40 has a threaded portion 44 formed on an inner surface 116 facing toward the inner member 36. An outer surface 46 of the outer annular skirt 40 has a toothed engagement portion 48 extending along at least a portion of a longitudinal length of the outer annular skirt 40. The toothed engagement portion 48 is configured for engaging with at least a portion of the connector assembly 32.

Figure 83:
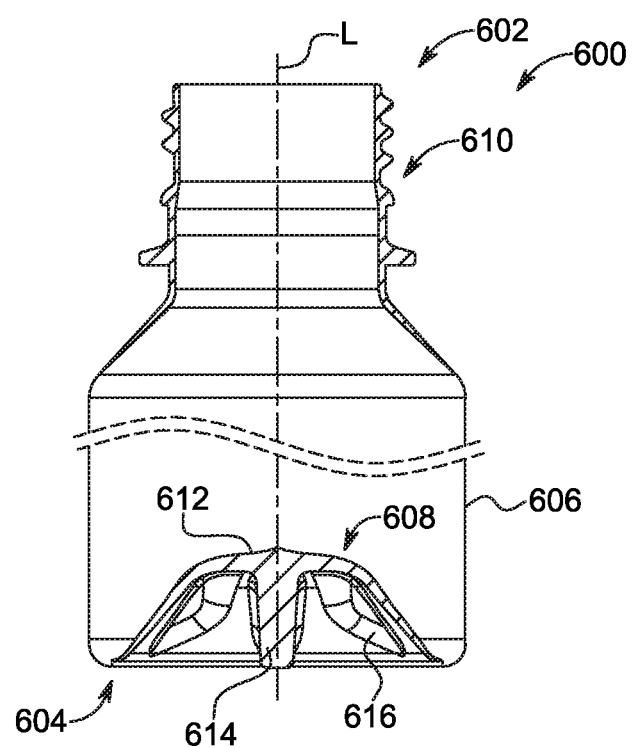
FIG. 83 is a side cross-sectional view of a syringe for use with a connector system in accordance with another aspect.

With reference to FIG. 83, another aspect of the syringe 12 is shown as a rolling diaphragm syringe 600 having a flexible sidewall. The rolling diaphragm syringe 600 may be used as the syringe in any example of the present disclosure described herein. The rolling diaphragm syringe 600 is adapted for use in CT, MRI, PET, and like procedures and operable at typical operating pressures of, for example, about 10-300 psi, such as 200-300 psi, depending on the viscosity of the fluid and the desired rate of injection. In some examples, the rolling diaphragm syringe 600 may be configured for use in procedures requiring pressures on the order to 1,200 psi, such as angiography. In some aspects, the rolling diaphragm syringe 600 may be a syringe disclosed in International Patent Application No. PCT/US2015/027582 and International Patent Application No. PCT/US2016/028824, the disclosures of which are incorporated herein by reference.

With continued reference to FIG. 83, the rolling diaphragm syringe 600 generally includes a hollow body that includes a forward or distal end 602, a rearward or proximal end 604, and a flexible sidewall 606 extending therebetween along a longitudinal axis L. In use, the proximal end 604 is configured for insertion into a throughbore of a pressure jacket attached to a fluid injector such that the sidewall 606 is surrounded by the interior surface of the pressure jacket. At least a portion of the distal end 602 of the rolling diaphragm syringe 600 may be exposed from the distal end 602 of the pressure jacket. In some examples, the rolling diaphragm syringe 600 may be formed using a blow-molding technique. In other examples, the rolling diaphragm syringe 600 may be injection molded.

With continued reference to FIG. 83, the proximal end 604 of the syringe 600 connects to a closed end wall 608, and the distal end 602 of the rolling diaphragm syringe 600 defines a syringe neck 610 opposite the closed end wall 608. The distal end 602 may have a frusto-conical shape that gradually narrows from the sidewall 606 to the syringe neck 610. The syringe neck 610 is open to allow fluid to be introduced into and/or delivered from the syringe interior. The closed end wall 608 may be shaped to interface directly with a drive member of a fluid injector (not shown). For example, the closed end wall 608 may define a receiving end pocket for interfacing directly with a similarly-shaped drive member, which may be shaped to substantially match the shape of the closed end wall 608. The sidewall 606 and/or the end wall 608 may have uniform or non-uniform thickness. For example, the sidewall 606 may have increased thickness at the distal end 602 compared to end wall 608.

The sidewall 606 of the rolling diaphragm syringe 600 defines a soft, pliable or flexible, yet self-supporting body that is configured to roll upon itself under the action of the drive member. In particular, the sidewall 606 of the rolling diaphragm syringe 600 is configured to roll such that its outer surface is folded and inverted in a radially inward direction as the drive member is moved in a distal direction, and unroll and unfold in the opposite manner in a radially outward direction as the drive member is retracted in a proximal direction.

The rolling diaphragm syringe 600 may be made of any suitable medical-grade plastic or polymeric material, desirably a clear or substantially translucent plastic material, such as, but not limited to, polypropylene random copolymer, polypropylene impact copolymer, polypropylene homopolymer, polypropylene, polyethylene terephthalate, POM, ABS, HPDE, nylon, cyclic olefin copolymer, multilayer polypropylene, polycarbonate, ethylene vinyl acetate, polyethylene, and the like. The material of the rolling diaphragm syringe 600 is desirably selected to meet the required tensile and planar stress requirements, water vapor transmission, and chemical/biological compatibility.

The end wall 608 may have a central portion 612 having a substantially dome-shaped structure and a drive member engagement portion 614 extending proximally from the central portion 612, such as an approximate midpoint of the central portion 612. In some aspects, a distal most end of the central portion 612 may be substantially flat. The drive member engagement portion 614 is configured for engagement with the engagement mechanism on the drive member of the fluid injector. The proximal end 604 of the rolling diaphragm syringe 600 may have one or more ribs 616 protruding radially outward from the drive member engagement portion 614 along a proximal surface of the central portion 612. The distal end of the rolling diaphragm syringe 600 may be configured or include an attachment configured to interact with any of the embodiments of the connector assemblies described herein.

Figure 3:
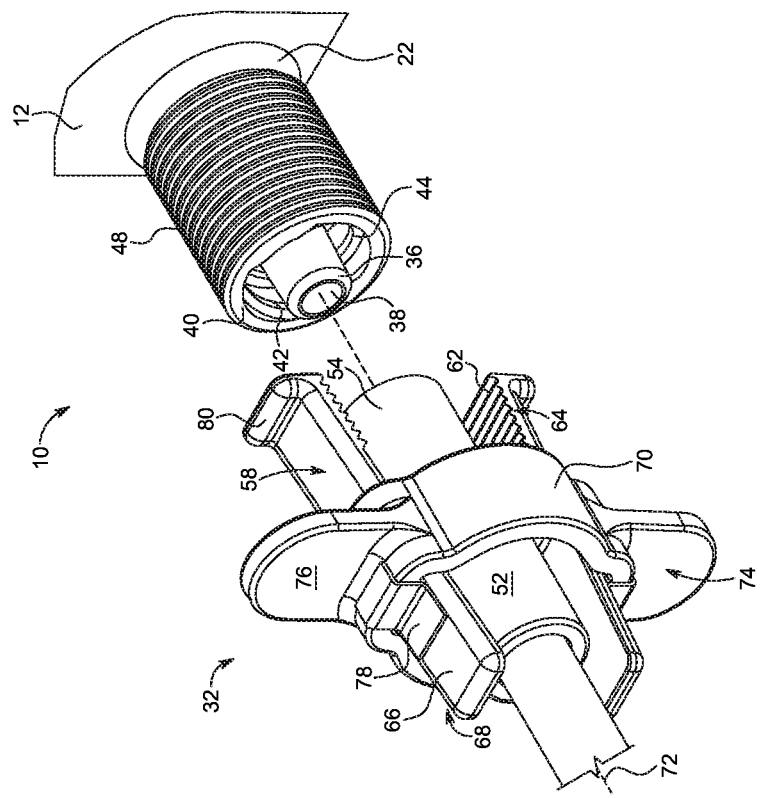
FIG. 3 is a detailed perspective view of the syringe nozzle and connector assembly shown in FIG. 2.
Figure 6:
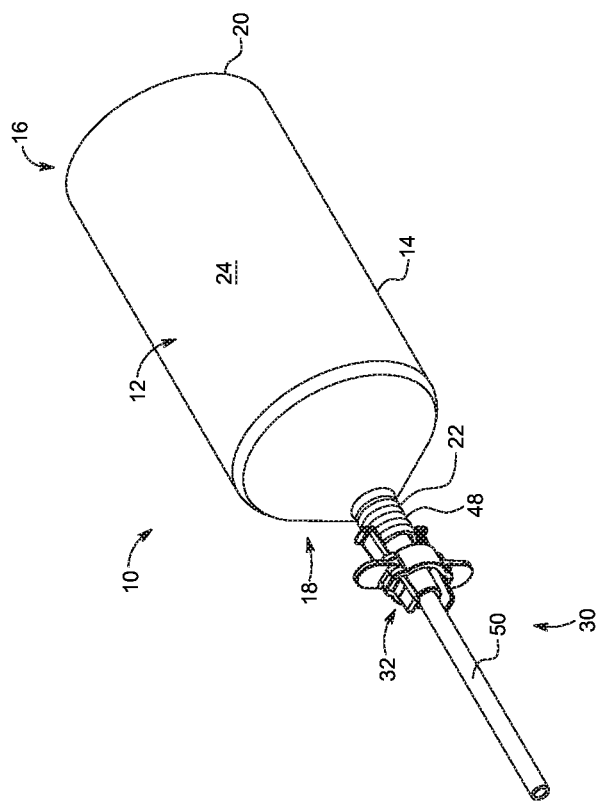
FIG. 6 is a perspective view of the syringe and connector assembly system of FIG. 2 in a first engagement position.

With reference now to FIGS. 2-5, the connector assembly 32 is shown prior to connection with the nozzle 22 of the syringe 12. The connector assembly 32 is connected at its distal end to tubing 50 configured for delivering fluid from the syringe 12. Referring to FIG. 3, the connector assembly 32 has a body 52 having a fluid fitting 54 at a proximal end thereof. The fluid fitting 54 is configured for engaging the inner member 36 of the syringe 12. A central fluid channel 56 (shown in FIGS. 4 and 5) extends through the body 52 of the connector assembly 32. The central fluid channel 56 is configured for establishing fluid communication with the fluid channel 38 of the syringe 12 when the connector assembly 32 is connected to the syringe 12. The connector assembly 32 includes at least a pair of flexible, resilient gripping arms 58 connected to the body 52 by a radial extension 60 (shown in FIG. 5). The gripping arms 58 extend along at least a portion of the longitudinal length of the body 52. The gripping arms 58 are deflectable in a radial direction about the radial extension 60 toward and away from the body 52. The gripping arms 58 are desirably deflectable away from the body 52 of the connector assembly 32 such that the gripping arms 58 can be distanced radially from the outer annular skirt 40 of the syringe 12 in order to allow the fluid fitting 54 to be engaged with the inner member 36 of the syringe 12. Each gripping arm 58 has one or more gripping elements 62 at its proximal end 64. The gripping elements 62 may be oriented to face toward the body 52. The one or more gripping elements 62 are configured for engaging the toothed engagement portion 48 on the syringe 12 when the connector assembly 32 is positioned over the nozzle 22, as described herein. In some aspects, the gripping arms 58 may have an initial position where the proximal end 64 is spread apart from the body 52 such that the fluid fitting 54 can be engaged with the inner member 36 of the nozzle 22 without engagement of the gripping arms 58 with the toothed engagement portion 48. The gripping arms 58 also have a pressing surface 66 at their distal end 68 and facing away from the body 52. The pressing surface 66, when pressed between the user's fingers, causes the proximal end 64 of the gripping arms 58 to be deflected radially outward such that the connector assembly 32 may be removed from the nozzle 22 of the syringe 12.

With continued reference to FIGS. 2-5, the connector assembly 32 further includes a collar 70 extending around at least a portion of the gripping arms 58. In some aspects, the collar 70 extends circumferentially around the gripping arms 58. The collar 70 may be slidable along a longitudinal axis 72 of the body 52 of the connector assembly 32. The collar 70 has at least one flange 74 extending radially outward relative to the body of the collar 70. The at least one flange 74 defines a push surface 76 that the user can engage to slide the collar 70 from the distal end 68 of the gripping arms 58 toward the proximal end 64.

With reference to FIGS. 6-9, the collar 70 is retained in an initial position at the distal end 68 of the gripping arms 58 by a frangible retaining member 78. One portion of the frangible retaining member 78 is secured on at least one of the gripping arms 58 while a second portion of the frangible retaining member 78 is secured to at least a portion of the collar 70. The frangible retaining member 78 may be breakable upon an application of a proximally-directed force on the push surface 76 of the flange 74 (see FIGS. 10-12). In some aspects, the frangible retaining member 78 is breakable upon application of a proximally-directed force of approximately 10 pounds. In other aspects, the force needed to break the frangible retaining member 78 may be more or less than 10 pounds. In some aspects, the force needed to break the frangible retaining member 78 is chosen such that, prior to the breaking of the frangible retaining member 78, the connector assembly 32 is pushed by the user into engagement with the nozzle 22 of the syringe 12 such that a fluid-tight connection is established between the inner member 36 of the nozzle 22 and the fluid fitting 54 of the connector assembly 32. For example, upon the application of the proximally-directed force on the flange 74 of the collar 70 and prior to the breaking of the frangible retaining member 78, the female luer taper 54 of the connector 32 is advanced along the male luer taper 36 of the nozzle 22 with sufficient force to create a seal before breaking frangible retaining member 78. The arms do not move into engagement until the overcoming force to move the collar 70 is achieved. Only when the collar 70 slides, do the teeth 62 engage with the toothed engagement portion 48.

Figure 10:
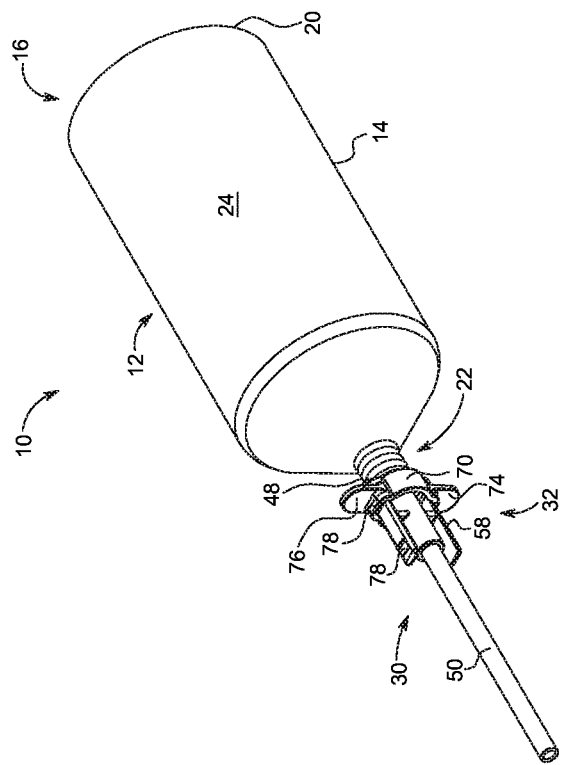
FIG. 10 is a perspective view of the syringe and connector assembly of FIG. 2 in a second engagement position.
Figure 9:
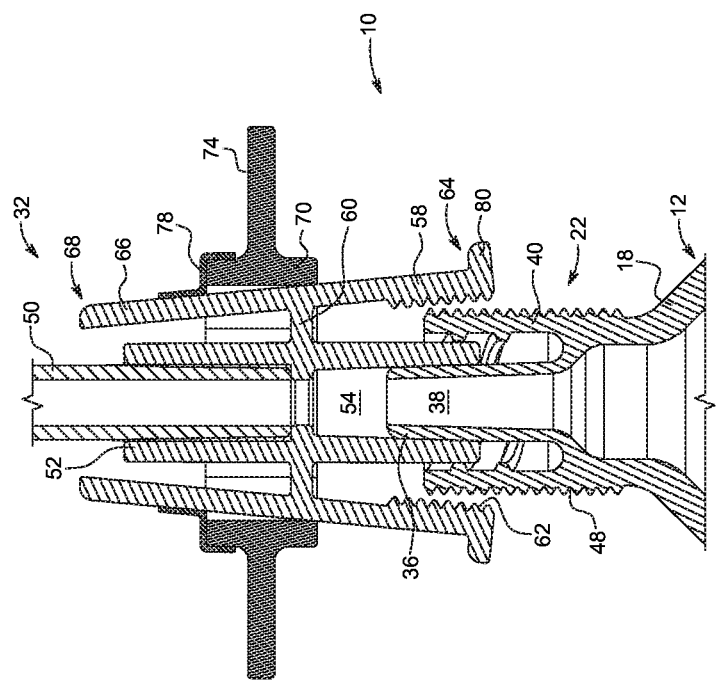
FIG. 9 is a detailed, side, cross-sectional view of the syringe nozzle and the connector assembly shown in FIG. 8.
Figure 12:
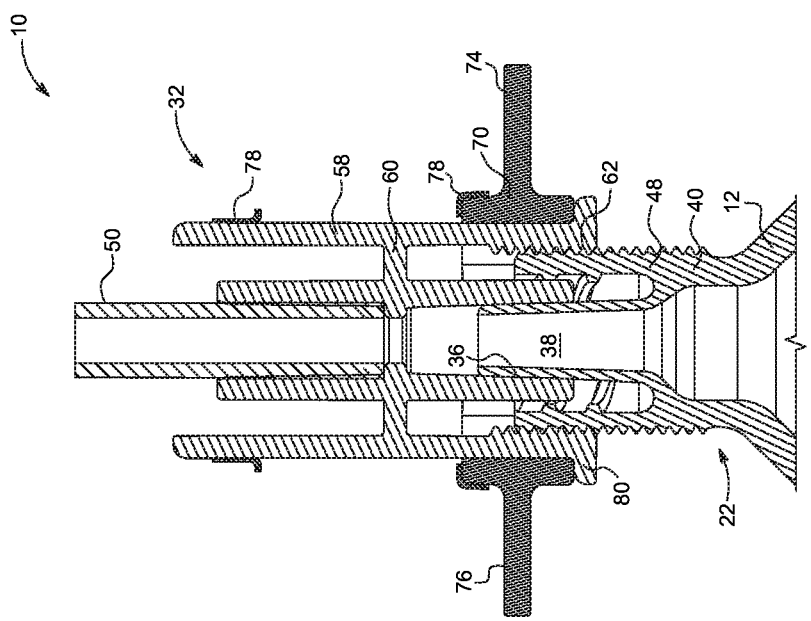
FIG. 12 is a detailed, side, cross-sectional view of the syringe nozzle and the connector assembly shown in FIG. 11.
Figure 11:
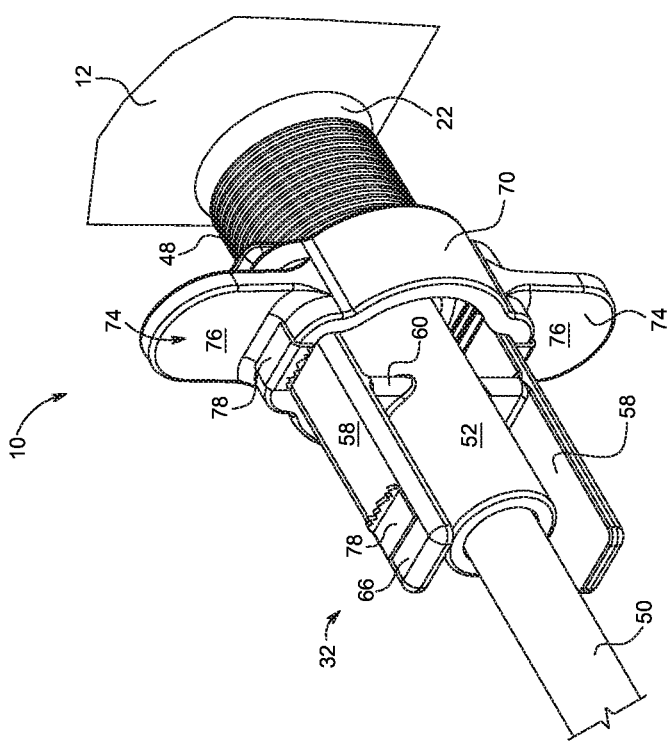
FIG. 11 is a detailed perspective view of the syringe nozzle and the connector assembly shown in FIG. 10.

With reference to FIGS. 10-12, continued distally-directed force on the flange 74 of the collar 70 causes the frangible retaining member 78 to break, thereby freeing the collar 70 from its initial position on the gripping arms 58. The collar 70 is moved proximally along the length of the gripping arms 58 until the collar 70 engages a stop 80 at the proximal end 64 of the gripping arms 58. Movement of the collar 70 along the gripping arms 58 toward the proximal end 64 causes the gripping arms 58 (shown in FIG. 9) to move radially inward toward the exterior of the outer annular skirt 40. In the final position, where the collar 70 is engaged against the stop 80, the collar 70 urges the proximal end 64 of the gripping arms 58 radially inward such that the gripping elements 62 are in engagement with the toothed engagement portion 48 on the nozzle 22. The collar 70 helps retain the connector assembly 32 on the nozzle 22 by preventing the proximal end 64 of the gripping arms 58 from deflecting radially outward relative to the outer annular skirt 40 of the nozzle 22 and out of engagement with the toothed engagement portion 48. It is also contemplated that other methods of establishing the sliding luer to luer sealing force (10 pounds) can be achieved, such as a collar sliding over an interference bump or a spring force.

In various aspects, the angle of orientation of a radially inward surface of the one or more gripping elements 62 and the surface of the toothed engagement portion 48 can be adjusted such that a mating contact of the gripping elements 62 and the surface of the toothed engagement portion 48 is maximized when connector assembly 32 is attached to syringe nozzle 22. Once engaged with the nozzle 22, the connector assembly 32 may be rotated about a longitudinal axis of the syringe 12 without disengaging the fluid path between the connector assembly 32 and the nozzle 22.

To remove the connector assembly 32 from the syringe nozzle 22, the collar 70 is moved from the stop 80 in a distal direction toward the distal end 68 of the gripping arms 58. Movement of the collar 70 in the distal direction frees the proximal end 64 of the gripping arms 58 to move radially outward relative to the outer annular skirt 40 when the pressing surface 66 on the distal end 68 of the gripping arms 58 is engaged in a radially inward direction. Such movement of the gripping arms 58 disengages the gripping elements 62 from the toothed engagement portion 48 on the syringe nozzle 22. The connector assembly 32 can then be removed from the nozzle 22 by pulling the connector assembly 32 in a distal direction relative to the nozzle 22.

The connector assembly 32 and other connectors of the present disclosure can also include an additional fluid path element, such as a multiport connector or a valve mechanism (for example, a check valve, a ball valve, a stopcock valve, other type of valve, transducer or other fluid path element) in fluid connection with the central fluid channel 56.

With reference to FIGS. 13-21B, a syringe and connector assembly 10 is illustrated in accordance with another aspect. With specific reference to FIGS. 13-14, the syringe 12 has the distal end 18 with a conically tapered portion 82 terminating at the nozzle 22. The tapered portion 82 has at least one engagement portion 84 provided thereon. In some aspects, a plurality of engagement portions 84 may be provided on the tapered portion 82. For example, the plurality of engagement portions 84 may be separated radially from each other around a circumference of the tapered portion 82 at equal or unequal radial increments. Each engagement portion 84 defines an engagement surface having one or more teeth 85 configured for engaging a corresponding engagement element on the connector assembly 32 and retaining the connector assembly 32 in fluid connection with the nozzle 22 of the syringe 12, as described herein.

Figure 13:
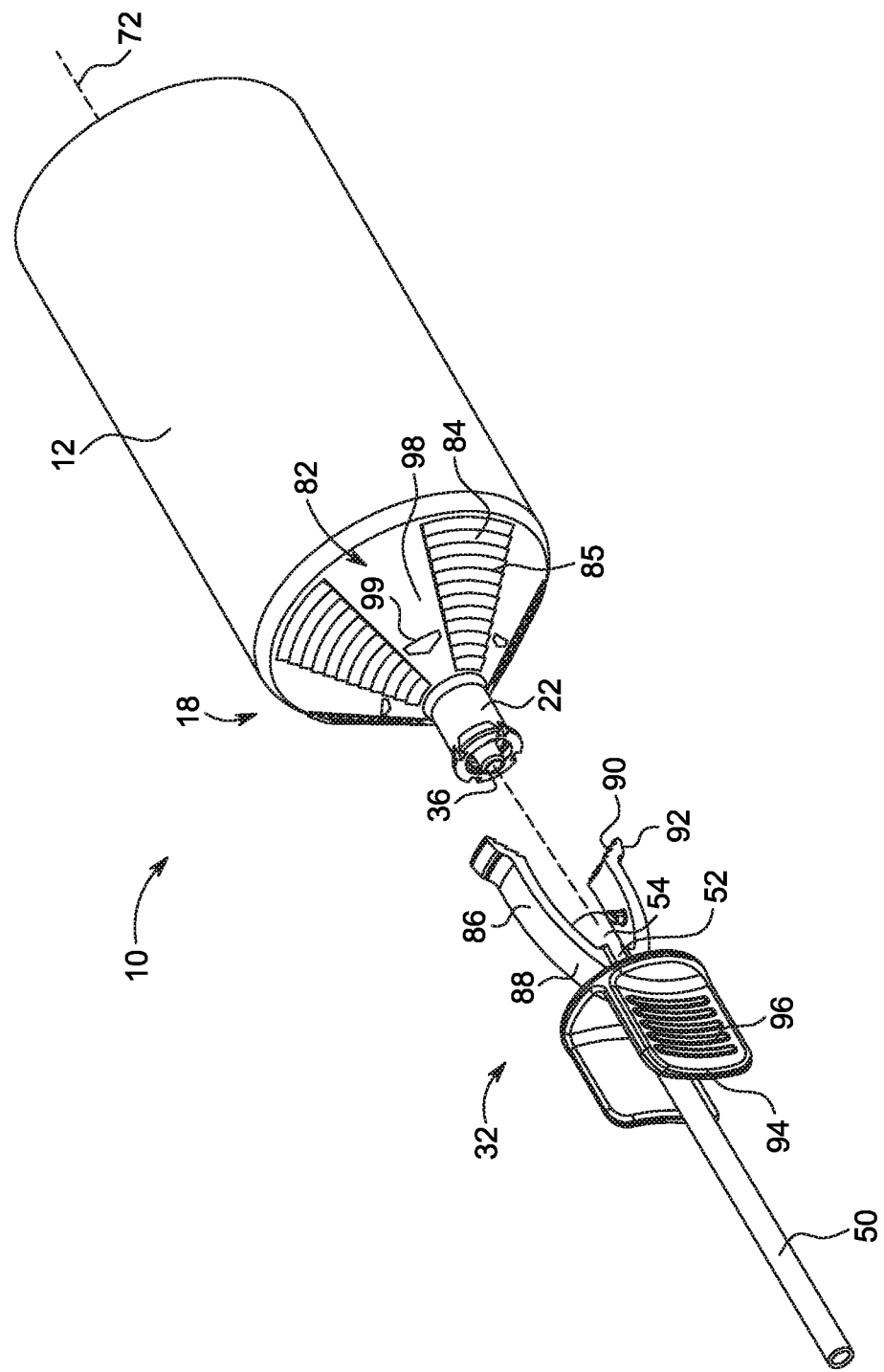
FIG. 13 is an exploded perspective view of a syringe and connector assembly in accordance with another aspect.
Figure 14:
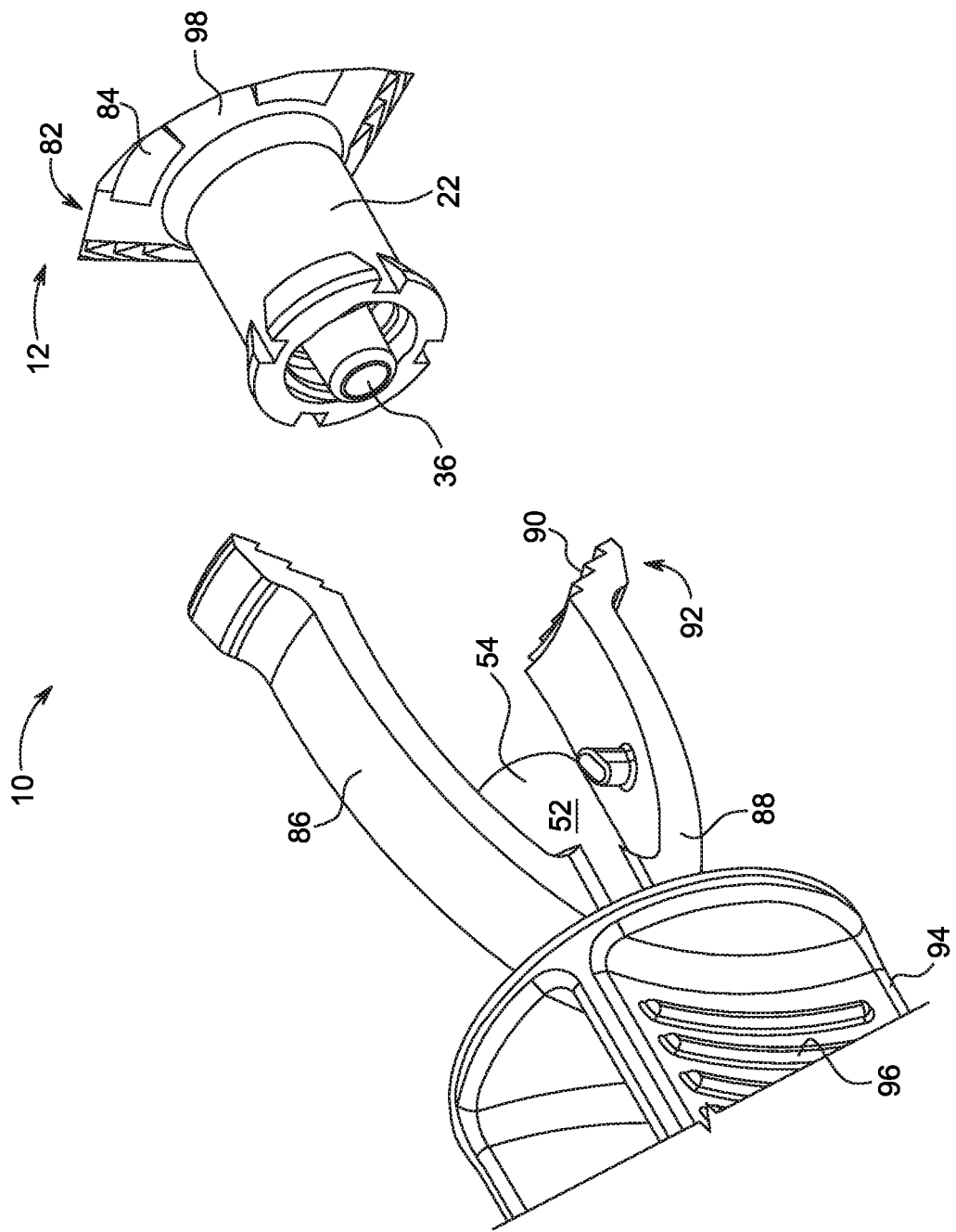
FIG. 14 is a detailed perspective view of the syringe nozzle and connector assembly shown in FIG. 13.
Figure 15:
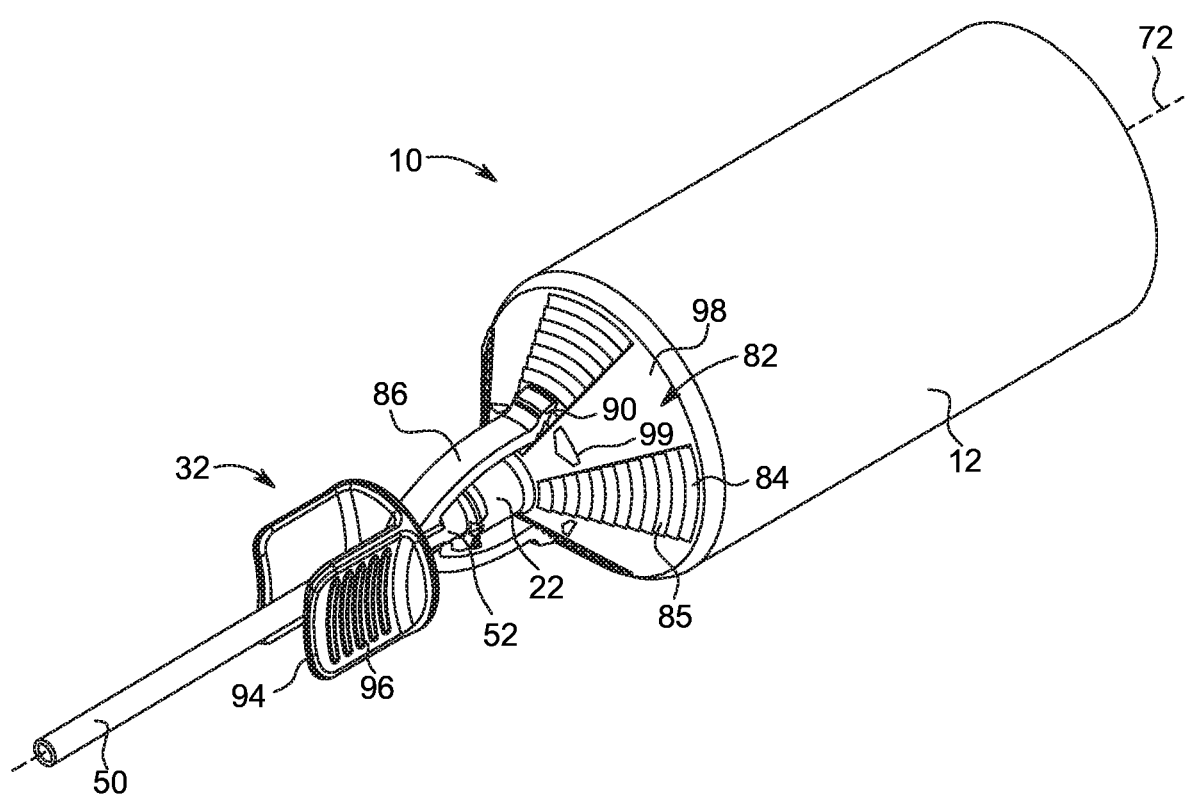
FIG. 15 is a perspective view of the syringe and connector assembly of FIG. 13 in an engaged position.

FIGS. 13-14 illustrate the connector assembly 32 prior to the initial connection with the syringe 12. The connector assembly 32 is connected at its distal end to tubing 50 configured for delivering fluid from the syringe 12. The connector assembly 32 has a body 52 having a fluid fitting 54 at a proximal end thereof. The fluid fitting 54 is configured for engaging the inner member 36 of the syringe 12. A central fluid channel 56 (shown in FIGS. 18-19) extends through the body 52 of the connector assembly 32. The central fluid channel 56 is configured for being in fluid communication with the fluid channel 38 (shown in FIGS. 18-19) of the syringe 12 when the connector assembly 32 is connected to the syringe 12. The connector assembly 32 includes at least a pair of flexible, resilient engagement arms 86 connected at their distal end 88 to the body 52. The engagement arms 86 are deflectable in a radial direction toward and away from the body 52. Each engagement arm 86 has one or more engagement elements 90 at its proximal end 92. The engagement elements 90 may be oriented to face toward the body 52. The one or more engagement arms 86 are configured for engaging the engagement portion 84 on the tapered portion 82 of the syringe 12 when the connector assembly 32 is positioned over the nozzle 22 and when the one or more engagement arms 86 are aligned radially relative to the tapered portion 82 of the syringe 12, as described herein.

Figure 19:
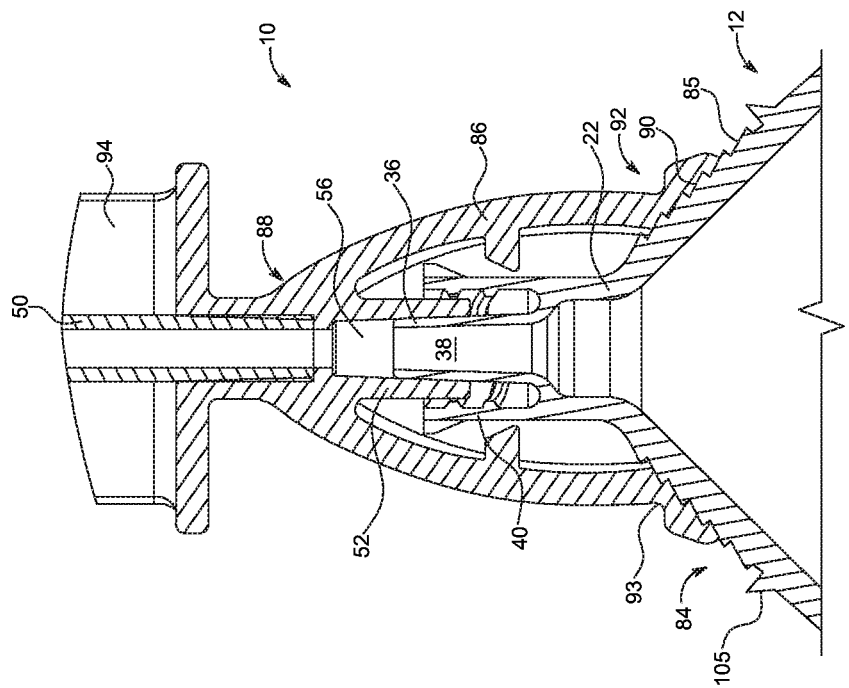
FIG. 19 is a detailed, side, cross-sectional view of the syringe nozzle and the connector assembly shown in FIG. 15.
Figure 18:
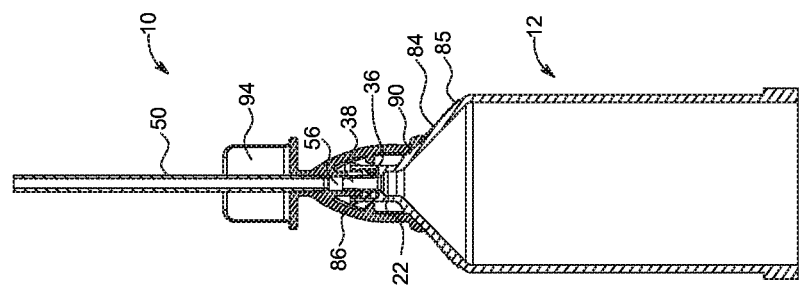
FIG. 18 is a side, cross-sectional view of the syringe and connector assembly shown in FIG. 15.
Figure 23:
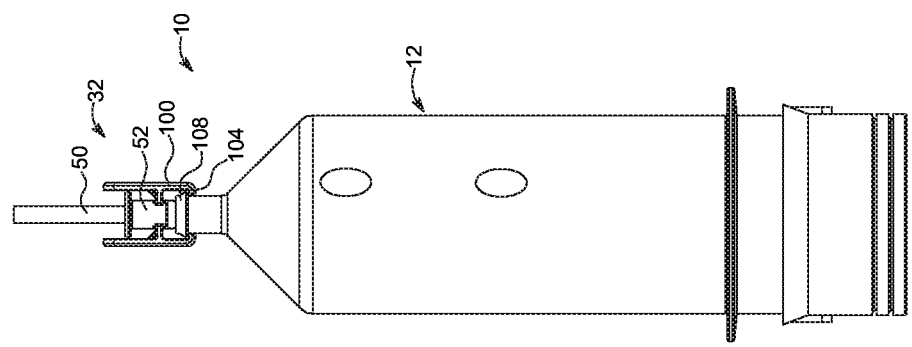
FIG. 23 is a side view of the syringe and connector assembly of FIG. 22 in an assembled position.

With continued reference to FIGS. 13-14, the connector assembly 32 further includes a tab 94 extending distally from the body 52. In some aspects, the tab 94 may define a gripping surface 96 that the user can engage to handle the connector assembly 32. Upon movement of the connector assembly 32 in a proximal direction toward the nozzle 22 (FIG. 15), the engagement elements 90 on the engagement arms 86 may be brought into engagement with the engagement portion 84 of the nozzle 22 to secure the connector assembly 32 to the nozzle 22, such as shown in FIGS. 13-14. Continued movement of the connector assembly 32 in a proximal direction causes the engagement arms 86 to spread apart in a radially outward direction relative to the body 52. The engagement elements 90 grip the engagement portion 84 on the tapered portion 82 of the syringe 12. The engagement elements 90 and the engagement portion 84 are configured such that the engagement elements 90 can move in a proximal direction along the engagement portion 84, but are prevented from movement in a distal direction upon an application of a distally-directed force. In various aspects, the angle of orientation of a radially inward surface of the one or more engagement elements 90 and the surface of the engagement portion 84 can be adjusted such that a mating contact of the engagement elements 90 and the surface of the engagement portion 84 is maximized when the connector assembly 32 is attached to the syringe nozzle 22. During engagement between the engagement elements 90 and the engagement portion 84 of the syringe 12, the fluid fitting 54 on the connector assembly 32 is brought in fluid communication with the inner member 36 on the syringe nozzle 22. The proximal end 92 of the engagement elements 90 may have an area of reduced cross section, indicated by reference numeral 93 in FIG. 19, to increase the flexibility of the engagement elements 90. With reference to FIG. 19, at least one stop element 105 may be provided at a proximal end of the engagement portion 84 to delimit the proximal movement of the connector assembly 32 relative to the nozzle 22. Contact between at least one of the engagement elements 90 with the at least one stop element 105 may provide an indication to the user that the connector assembly 32 has been sufficiently engaged with the nozzle 22 of the syringe 12.

Figure 16:
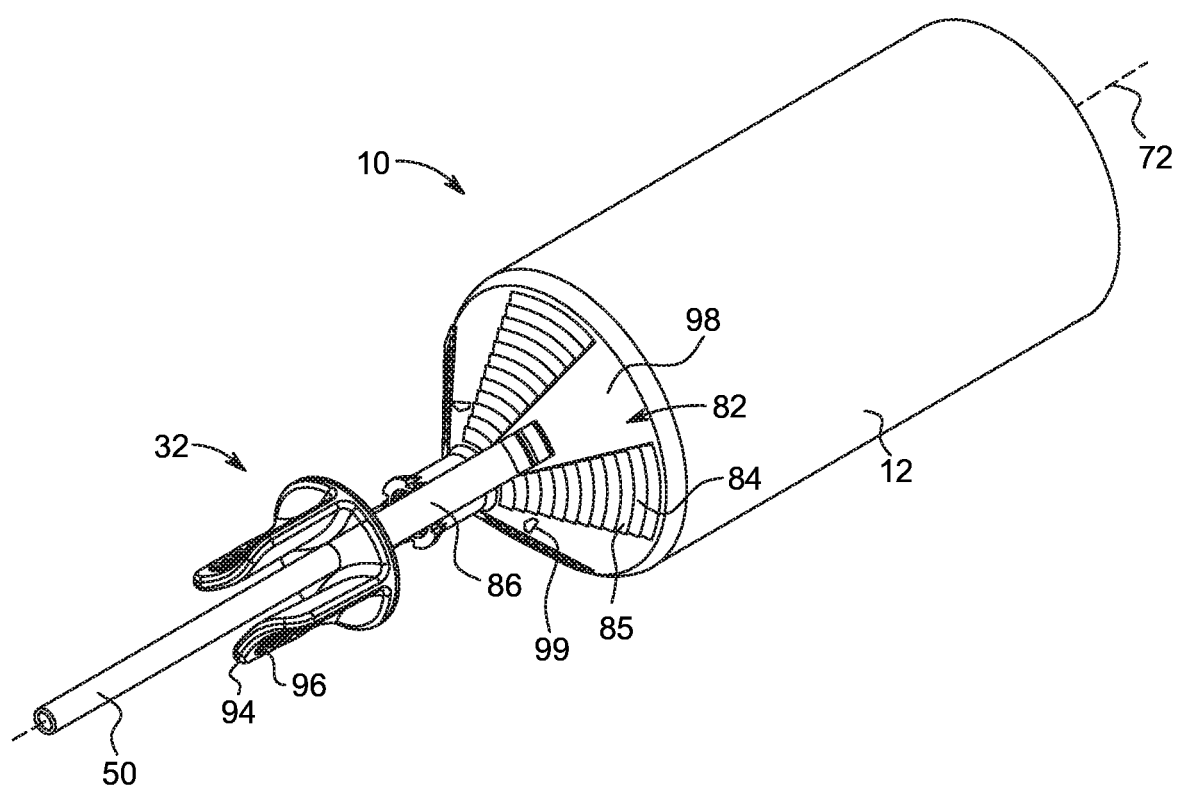
FIG. 16 is a perspective view of the syringe and connector assembly of FIG. 13 in a disengaged position.
Figure 17:
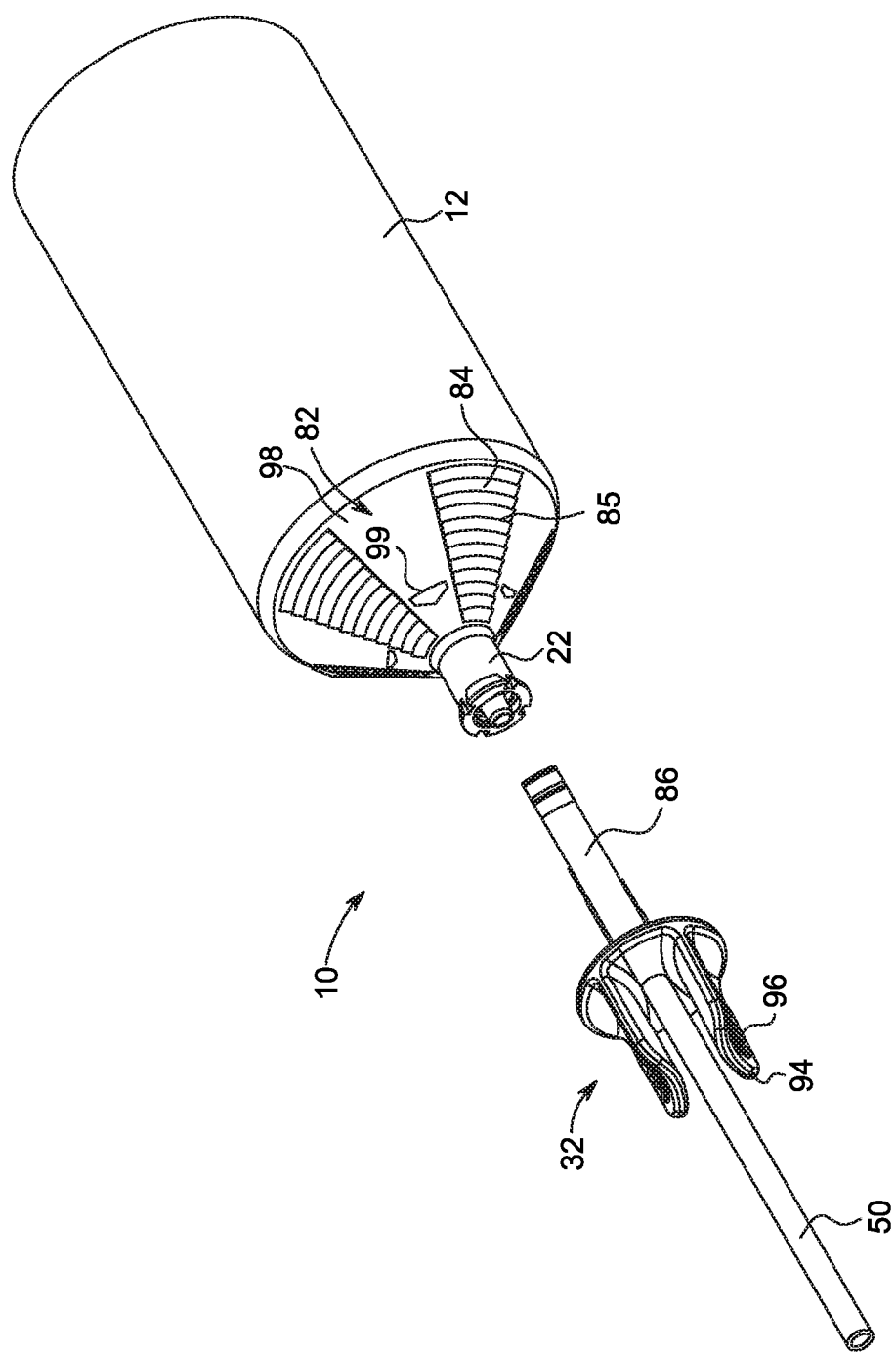
FIG. 17 is a perspective view of the syringe and connector assembly of FIG. 13 with the connector removed from the syringe.

To remove the connector assembly 32 from the syringe nozzle 22, the body 52 of the connector assembly 32 is rotated about the longitudinal axis 72 such that the engagement arms 86 move radially away from the engagement portion 84 on the tapered portion 82 of the syringe 12 into the disengagement region 98 (see FIGS. 16 and 21A). Such movement of the engagement arms 86 disengages the engagement elements 90 from the engagement portion 84 on the syringe nozzle 22. The connector assembly 32 can then be removed from the nozzle 22 by pulling the connector assembly 32 in a distal direction relative to the nozzle 22, as shown in FIG. 17. In some aspects, such as shown in FIG. 21A, at least one release rib 99 protrudes distally from an upper surface of the disengagement region 98 to aid in releasing the connector assembly 32 from the nozzle 22. With reference to FIG. 21A, a plurality of release ribs 99 is provided in each disengagement region 98 of the syringe 12. Referring to FIG. 21B, the at least one release rib 99 may have at least one inclined surface 101 that urges the connector assembly 32 (shown in FIG. 16) in a radial and/or distal direction upon rotation of the connector assembly 32 out of alignment with the engagement portion 84 and into the disengagement region 98 of the syringe 12. In some aspects, a pair of inclined surfaces 101 joins together at a peak 103 located at an approximate midpoint of the release rib 99. Each inclined surface 101 may be pointed toward the nozzle 22 such that rotation of the connector assembly 32 lifts the connector assembly 32 in a distal direction away from the nozzle 22.

With reference to FIGS. 22-27, the syringe and connector assembly 10 is illustrated in accordance with another aspect. The connector assembly 32 is connected at its distal end to tubing 50 configured for delivering fluid from the syringe 12. The connector assembly 32 has a body 52 having a fluid fitting 54 at a proximal end thereof. The fluid fitting 54 is configured for engaging the inner member 36 of the nozzle 22 of the syringe 12. A central fluid channel 56 (shown in FIG. 25) extends through the body 52 of the connector assembly 32. The central fluid channel 56 is configured for being in fluid communication with the fluid channel 38 of the syringe 12 when the connector assembly 32 is connected to the syringe 12.

The connector assembly 32 includes at least a pair of flexible, resilient locking arms 100 connected to the body 52 by a radial extension 102. The locking arms 100 extend along at least a portion of the longitudinal length of the body 52. The locking arms 100 are deflectable in a radial direction about the radial extension 102 toward and away from the body 52. The locking arms 100 are desirably deflectable away from the body 52 of the connector assembly 32 such that the locking arms 100 can be distanced radially from the outer annular skirt 40 of the syringe 12 in order to allow the fluid fitting 54 to be engaged with the inner member 36 of the nozzle 22 of the syringe 12. Each locking arm 100 has one or more locking elements 104 at its proximal end 106. The locking elements 104 are configured for engaging a lip 108 on a distal end of the nozzle 22, as described herein. The locking arms 100 also have a pressing surface 112 at their distal end 110 and facing away from the body 52. The pressing surface 112, when pressed between the user's fingers, causes the proximal end 106 of the locking arms 100 to be deflected radially outward such that the connector assembly 32 may be removed from the nozzle 22.

Figure 27:
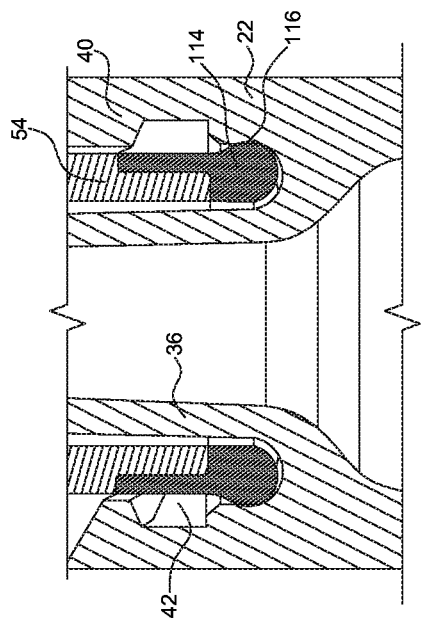
FIG. 27 is a detailed cross-sectional view of a connection interface between the syringe nozzle and the connector assembly shown in FIG. 26.
Figure 28:
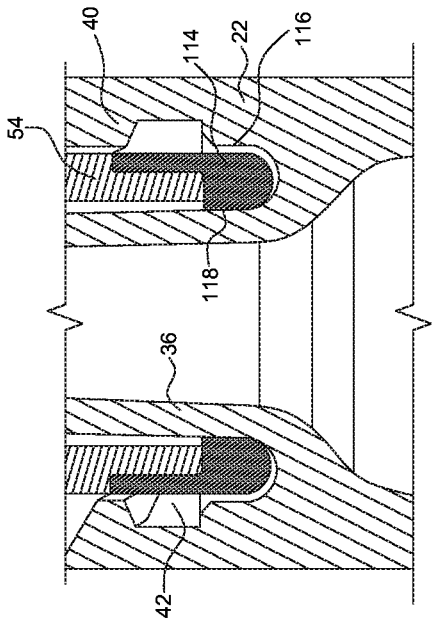
FIG. 28 is a detailed cross-sectional view of a connection interface between a syringe nozzle and a connector assembly in accordance with another aspect.
Figure 26:
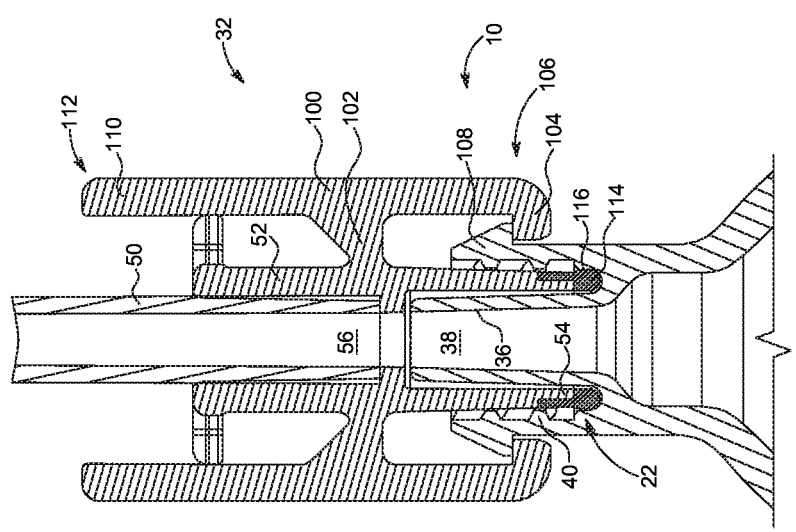
FIG. 26 is a detailed, side, cross-sectional view of the syringe nozzle and the connector assembly shown in FIG. 23.

With continued reference to FIGS. 22-27, the fluid fitting 54 may have a seal 114, such as an elastomeric seal. In some aspects, the seal 114 may be co-molded, adhesively connected, or otherwise attached at the fluid fitting 54 of the body 52. The seal 114 may extend radially outward relative to the fluid fitting 54 and is configured for engaging an inner surface 116 (shown in FIGS. 26-27) of the outer annular skirt 40 of the nozzle 22. With particular reference to FIG. 27, the seal 114 may be compressed when the fluid fitting 54 is inserted into the annular space 42 between the inner member 36 and the outer annular skirt 40 of the nozzle 22. With reference to FIG. 28, in another aspect, the seal 114 may extend radially inward relative to the fluid fitting 54 and is configured for engaging an outer surface 118 of the inner member 36. The seal 114 may be compressed against the outer surface 118 of the inner member 36 when the fluid fitting 54 is inserted into the annular space 42 between the inner member 36 and the outer annular skirt 40 of the nozzle 22. In yet another aspect, the seal 114 may be compressed between the inner surface 116 of the outer annular skirt 40 and the outer surface 118 of the inner member 36. For example, the seal 114 may be formed as a flexible and resilient member that is compressed to fill the void between the inner surface 116 of the outer annular skirt 40 and the outer surface 118 of the inner member 36.

With continued reference to FIGS. 22-27, upon movement of the connector assembly 32 in a proximal direction toward the nozzle 22, the locking arms 100 may be brought into engagement with the lip 108. Continued movement of the connector assembly 32 in a proximal direction causes the locking arms 100 to spread apart in a radially outward direction relative to the body 52. The locking elements 104 grip the lip 108 on the syringe nozzle 22. During engagement between the locking elements 104 and the lip 108 of the syringe 12, the fluid fitting 54 on the connector assembly 32 is brought in fluid communication with the inner member 36 on the syringe nozzle 22.

To remove the connector assembly 32 from the syringe nozzle 22, the locking arms 100 may be moved radially outward relative to the outer annular skirt 40 by engaging the pressing surface 112 on the distal end 110 of the locking arms 100 in a radially inward direction. Such movement of the locking arms 100 disengages the locking elements 104 from the lip 108 on the syringe nozzle 22. The connector assembly 32 can then be removed from nozzle 22 by pulling connector assembly 32 in a distal direction relative to nozzle 22.

Figure 31:
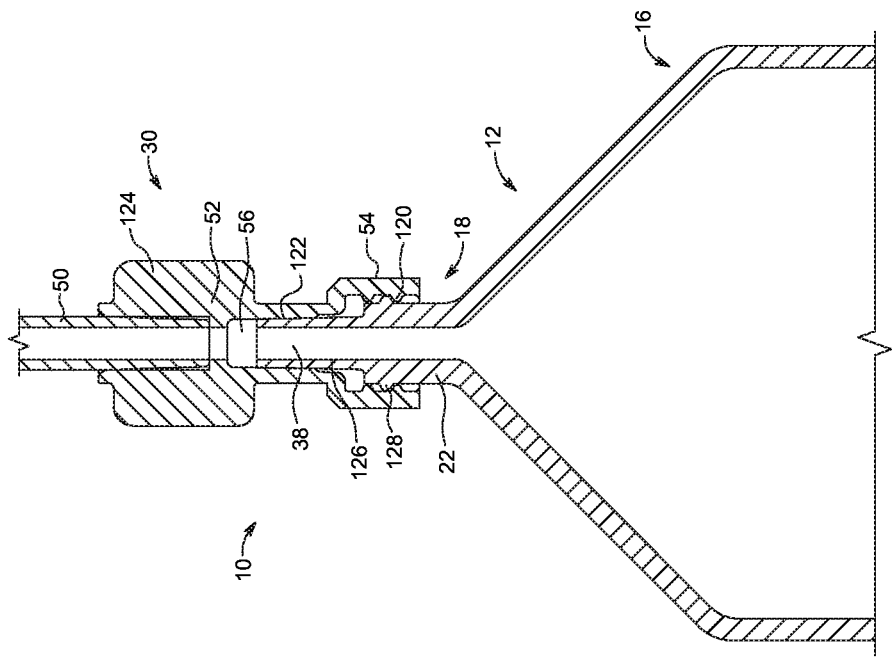
FIG. 31 is a side cross-sectional view of the syringe of FIG. 30 and the connector assembly of FIG. 29.
Figure 29:
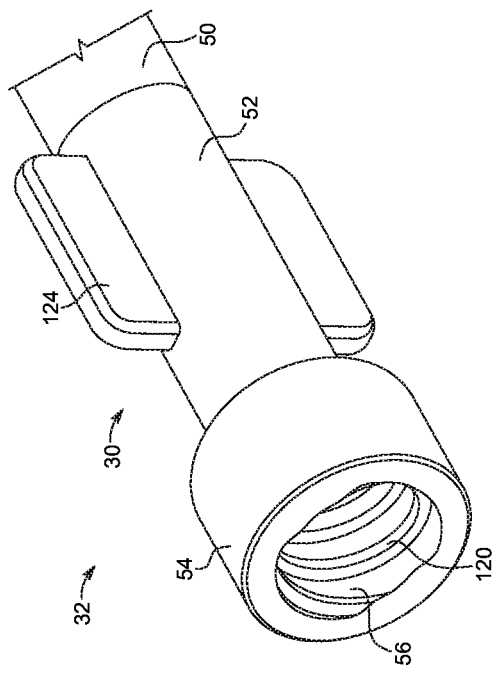
FIG. 29 is a perspective view of a connector assembly in accordance with another aspect.
Figure 30:
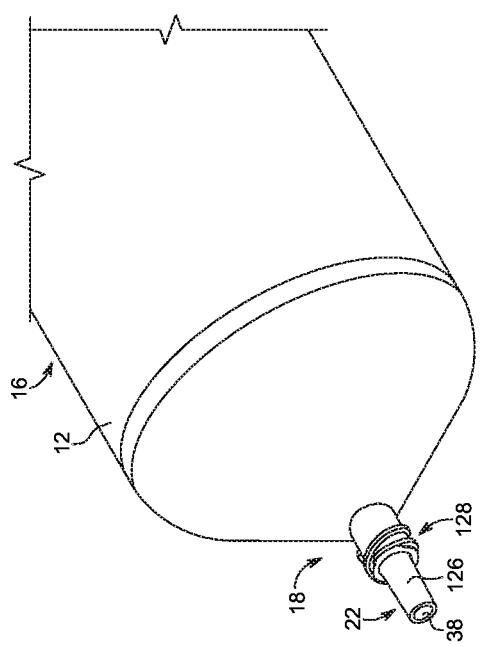
FIG. 30 is a perspective view of a syringe for use with the connector assembly shown in FIG. 29.

With reference to FIGS. 29-31, the connector assembly 32 is shown in accordance with another aspect. Referring initially to FIG. 29, the connector assembly 32 is shown prior to connection with the nozzle 22 of the syringe 12 (shown in FIGS. 30-31). In some aspects, the connector assembly 32 may be formed on a fluid path set 30 that is configured for delivering fluid from the syringe to the patient or a container for receiving the fluid. The connector assembly 32 is connected at its distal end to tubing 50 configured for delivering fluid from the syringe 12. The connector assembly 32 has a body 52 having a fluid fitting 54 at a proximal end thereof. The fluid fitting 54 is configured for engaging the nozzle 22 of the syringe 12. A central fluid channel 56 (shown in FIG. 31) extends through the body 52 of the connector assembly 32. The central fluid channel 56 is configured for being in fluid communication with the fluid channel 38 of the syringe 12 when the connector assembly 32 is connected to the syringe 12. The fluid fitting 54 includes a first connection member 120 on an inner surface facing the central fluid channel 56. In some aspects, the first connection member 120 may be a helical thread configured for engaging a corresponding thread on the nozzle 22. With reference to FIG. 31, at least a portion of the central fluid channel 56 has a tapering female element 122 that is configured for engaging a corresponding tapering male element 126 on the syringe nozzle 22 (shown in FIG. 30). The tapering female element 122 and the first connection member 120 are spaced apart axially along the longitudinal axis of the connector assembly 32. The connector assembly 32 includes at least one gripping arm 124 connected to the body 52. The at least one gripping arm 124 is configured for facilitating the handling of the connector assembly 32.

With reference to FIG. 30, the syringe 12 is illustrated in accordance with one aspect. A distal end 18 of the syringe 12 may have the nozzle 22 that is configured for releasable fluid connection with a fluid path set 30 that may be connected to the patient. The nozzle 22 has a tapering male element 126 that tapers in from the proximal end 16 to the distal end 18 of the syringe 12. A fluid channel 38 extends through the tapering male element 126 and is in fluid communication with the interior volume of the syringe 12. A second connection member 128 is provided proximally from the tapering male element 126. The second connection member 128 may be a helical thread configured for engaging a corresponding thread on the first connection member 120 of the connector assembly 32. The tapering male element 126 and the second connection member 128 are spaced apart axially along the longitudinal axis of the syringe 12.

With reference to FIG. 31, the connector assembly 32 is shown in connection with the syringe 12. The connector assembly 32 can be connected to the syringe 12 by aligning the fluid fitting 54 with the nozzle 22 of the syringe 12. The first connection member 120 of the connector assembly 32 is configured for engaging the second connection member 128 on the syringe nozzle 22. In some aspects, the first and second connection members 120, 128 may be connected by rotating one of the syringe 12 and the connector assembly 32 relative to the other of the syringe 12 and the connector assembly 32 to form a threaded engagement between the first and second connection members 120, 128. The connector assembly 32 is moved in a proximal direction as the first and second connection members 120, 128 are engaged with each other. Such proximal movement causes the outer surface of the tapering male element 126 of the nozzle 22 to engage the inner surface of the tapering female element 122 of the connector assembly 32. The interface between the first and second connection members 120, 128 is axially separated from the interface between the tapering male and female elements 126, 122.

To remove the connector assembly 32 from the syringe nozzle 22, one of the syringe 12 and the connector assembly 32 is rotated relative to the other of the syringe 12 and the connector assembly 32 to release the threaded engagement between the first and second connection members 120, 128. Rotation may be in a clockwise or a counterclockwise direction. Such rotation disengages the first and second connection members 120, 128. The connector assembly 32 can then be removed from the nozzle 22 by pulling the connector assembly 32 in a distal direction relative to the nozzle 22.

Figure 34:
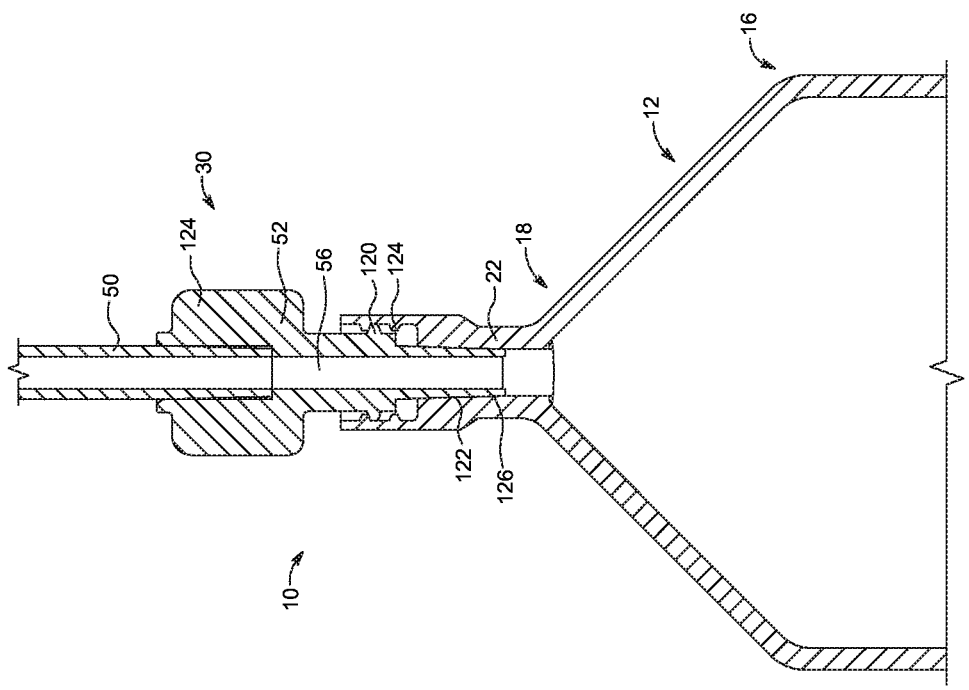
FIG. 34 is a side cross-sectional view of the syringe of FIG. 33 and the connector assembly of FIG. 32.
Figure 32:
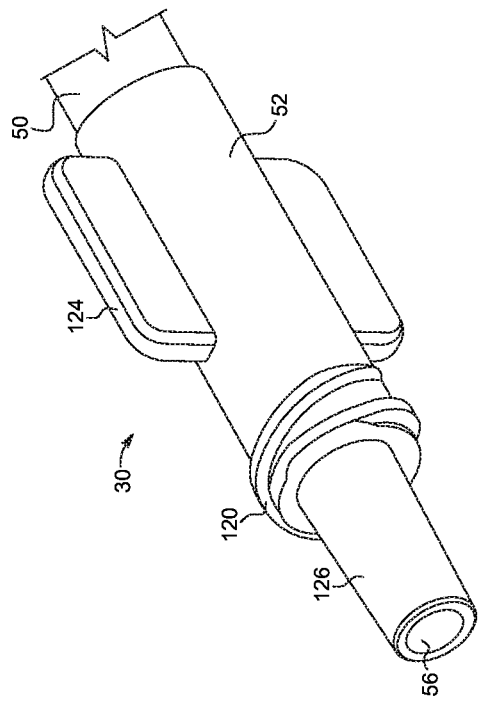
FIG. 32 is a perspective view of a connector assembly in accordance with another aspect.
Figure 33:
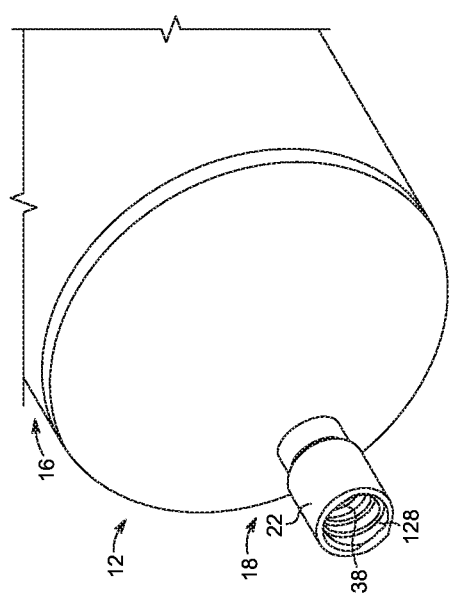
FIG. 33 is a perspective view of a syringe for use with the connector assembly shown in FIG. 32.

In other aspects, with reference to FIGS. 32-34, the arrangement of the first and second connection members 120, 128 and the tapering male and female elements 126, 122 may be reversed. In such aspects, tapering male element 126 may be provided on the connector assembly 32, while the tapering female element 122 may be provided on nozzle 22.

With reference to FIGS. 35-38B, a syringe 12 and connector assembly 32 is illustrated in accordance with another aspect. With specific reference to FIG. 35, a syringe 12 has a distal end 18 terminating at a nozzle 22. The nozzle 22 of the syringe 12 has an inner member 36 that tapers at an angle A relative to a longitudinal axis 13 of the syringe 12. In some aspects, the inner member 36 may be tapered at an angle A of 6%. The inner member 36 defines a fluid channel 38 that is in fluid communication with an interior volume 27 (shown in FIG. 4) of the syringe 12. The inner member 36 is surrounded by an outer annular skirt 40 that extends axially along at least a portion of the longitudinal length of the inner member 36. The inner member 36 is spaced apart radially from the outer annular skirt 40 by an annular space 42.

Figure 35:
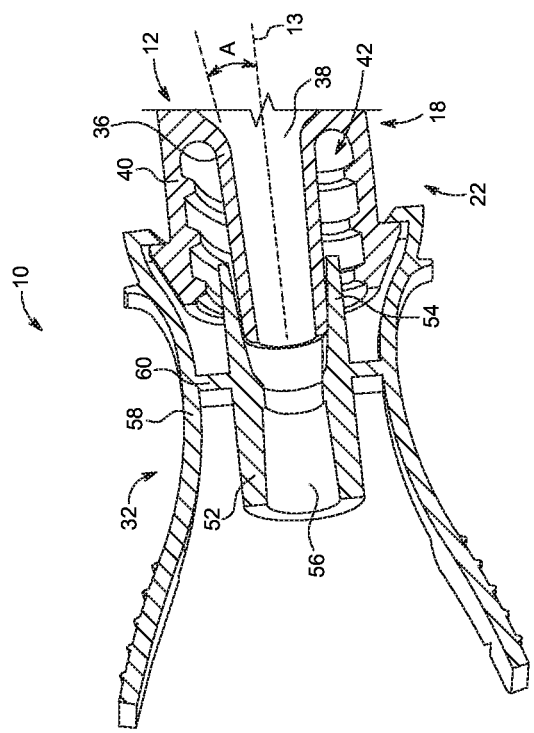
FIG. 35 is a cross-sectional view of a connection interface between a syringe nozzle and a connector in accordance with another aspect.

FIG. 35 illustrates a connector assembly 32 connected with the syringe 12. The connector assembly 32 has a body 52 having a fluid fitting 54 at a proximal end thereof. The fluid fitting 54 is configured for engaging the inner member 36 of the syringe 12. A central fluid channel 56 extends through the body 52 of the connector assembly 32. The central fluid channel 56 is configured for establishing fluid communication with the fluid channel 38 of the syringe 12 when the connector assembly 32 is connected to the nozzle 22 of the syringe 12. The connector assembly 32 includes at least a pair of flexible, resilient gripping arms 58 connected to the body 52 by a radial extension 60. The gripping arms 58 are deflectable in a radial direction about the radial extension 60 toward and away from the body 52. The gripping arms 58 are desirably deflectable away from the body 52 of the connector assembly 32 such that the gripping arms 58 can be distanced radially from the outer annular skirt 40 of the syringe 12 in order to allow the fluid fitting 54 to be engaged with the inner member 36 of the syringe 12. Other embodiments of gripping arms described herein may also be utilized with the central fluid channel configuration described below.

Figure 36:
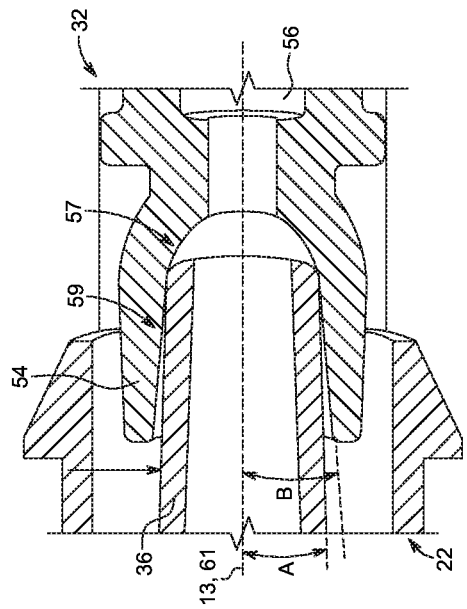
FIG. 36 is a first detailed cross-sectional view of the connection interface shown in FIG. 35.
Figure 37:
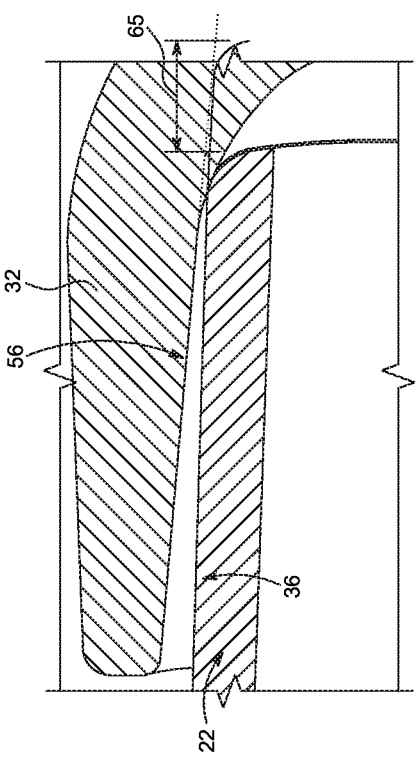
FIG. 37 is a second detailed cross-sectional view of the connection interface shown in FIG. 35.

With reference to FIG. 36, the central fluid channel 56 has a radiused distal end 57 that transitions into a substantially linear proximal end 59. The distal end of the central fluid channel 56 may taper at an angle B relative to a longitudinal axis 61 of the central fluid channel 56. The taper of angle B may be larger than, smaller than, or equal to the taper of angle A on the inner member 36 of the nozzle 22 (shown in FIG. 36). Desirably, the taper of angle A is smaller than the taper of angle B to allow the inner member 36 of the nozzle 22 to be inserted into the fluid fitting 54 of the connector assembly 32. Thus, angle B may be tapered at an angle that is larger than a standard 6% in standard luer fittings. Standard luer fittings have axial tolerance stacking issues due to manufacturing variability in the tapered sections of the male and female luer parts. Thus, a female luer with a smaller taper may prevent a male luer with a larger taper from being fully seated. By increasing the taper of angle B and providing a radiused distal end 57, axial tolerance is increased to compensate for any manufacturing variability between the syringe nozzle 22 and the connector assembly 32. With reference to FIG. 37, a tolerance zone 65 is defined as an axial distance between a first point of contact between the inner member 36 and the central fluid channel 56 for a connection interface with a smallest allowable tolerance necessary for a maximum interference fit (shown as X in FIG. 38A) and a second point of contact between the inner member 36 and the central fluid channel 56 for a connection interface with a largest allowable tolerance necessary for a minimum interference fit (shown as Y in FIG. 38B). It is also contemplated that, to maintain the seal strength at a reduced axial force, surface 56 could include a softer durometer material or a textured surface.

Figure 40:
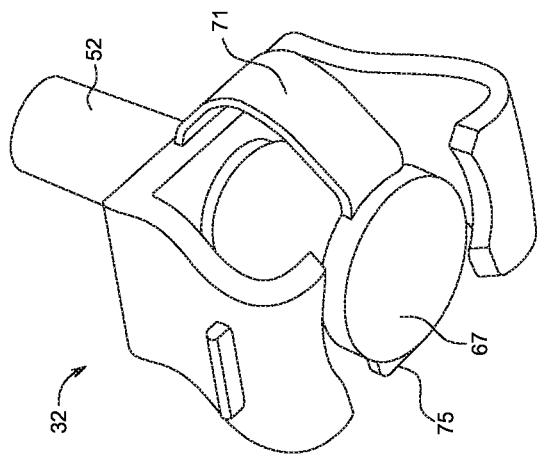
FIG. 40 is a perspective view of a connector assembly and dust cap in a closed position.
Figure 41:
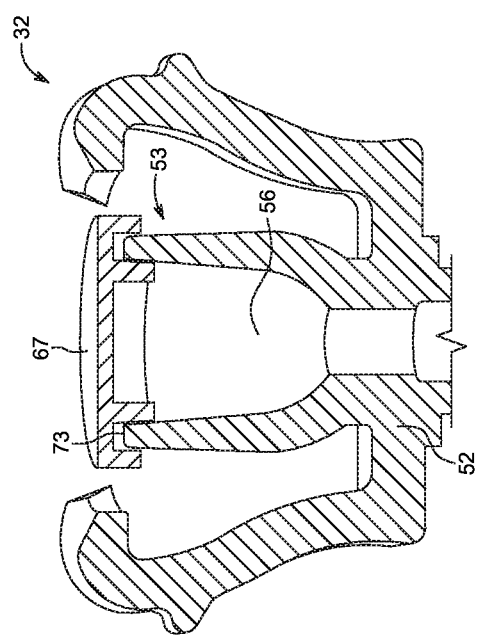
FIG. 41 is a cross-sectional view of the connector assembly and dust cap shown in FIG. 40.
Figures 38A, 38B:
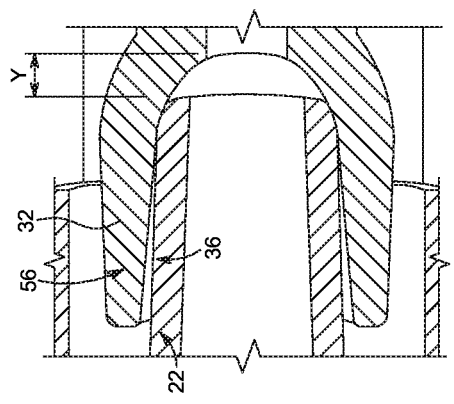
FIG. 38A is a detailed cross-sectional view of the connection interface at a minimum interference fit.
FIG. 38B is a detailed cross-sectional view of the connection interface at a maximum interference fit.
Figure 39:
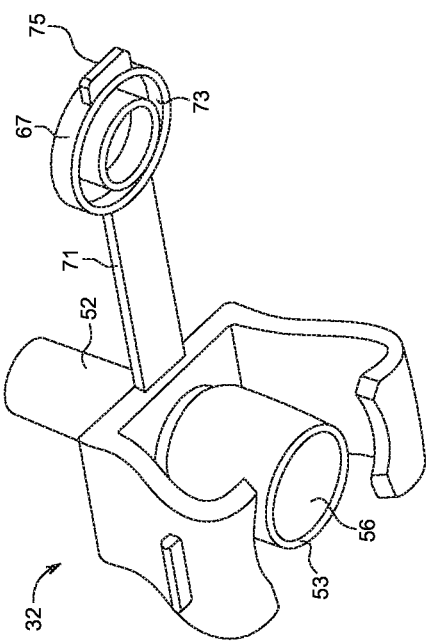
FIG. 39 is a perspective view of a connector assembly and dust cap in an open position.

With reference to FIGS. 39-41, a connector assembly 32 is illustrated in accordance with another aspect. The connector assembly 32 includes a removable dust cap 67 configured to seal a proximal end 53 of the body 52. The dust cap 67 may be connected to at least a portion of the body 52 by a flexible strap 71. An annular channel 73 on an inner portion of the dust cap 67 may be configured to receive at least a portion of an inner and outer sidewall of the body 52 at the proximal end 53, as shown in FIG. 41. The dust cap 67 may seal the central fluid channel 56 prior to connection with the nozzle 22 (shown in FIG. 2). A tab 75 may be provided on at least a portion of the dust cap 67 for facilitating removal of the dust cap 67 from a shielding position (shown in FIG. 40) and a non-shielding position (shown in FIG. 39).

Figure 22:
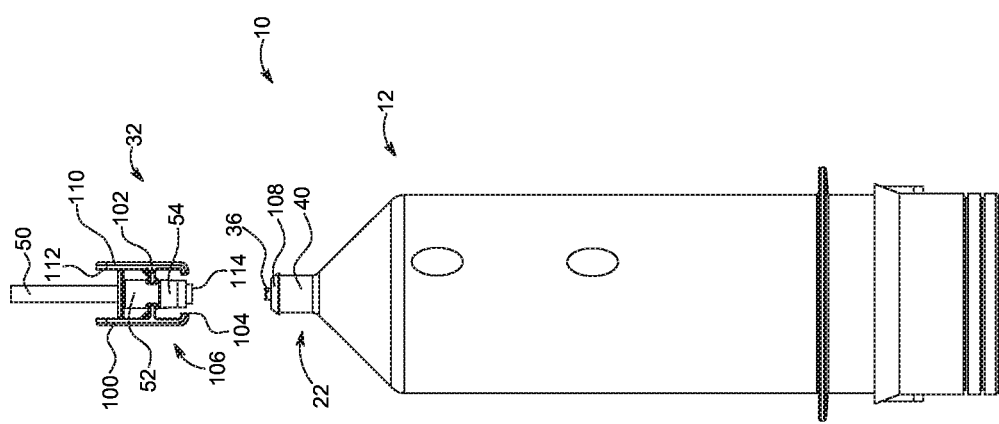
FIG. 22 is an exploded side view of a syringe and connector assembly in accordance with another aspect.
Figure 25:
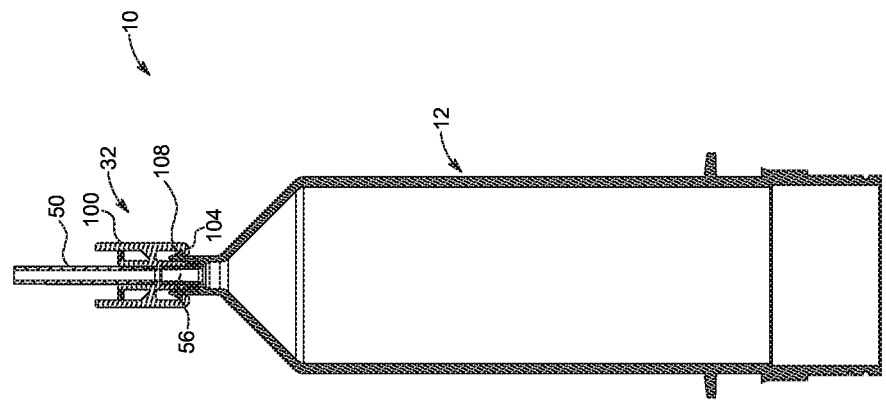
FIG. 25 is a side, cross-sectional view of the syringe and connector assembly of FIG. 23.
Figure 24:
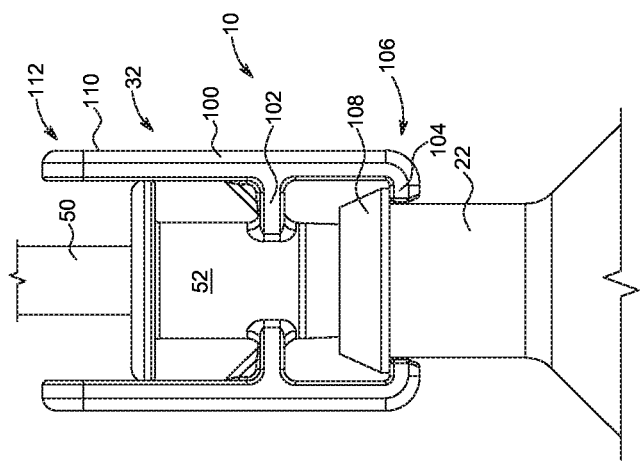
FIG. 24 is a detailed side view of the syringe nozzle and the connector assembly shown in FIG. 23.
Figure 42C:
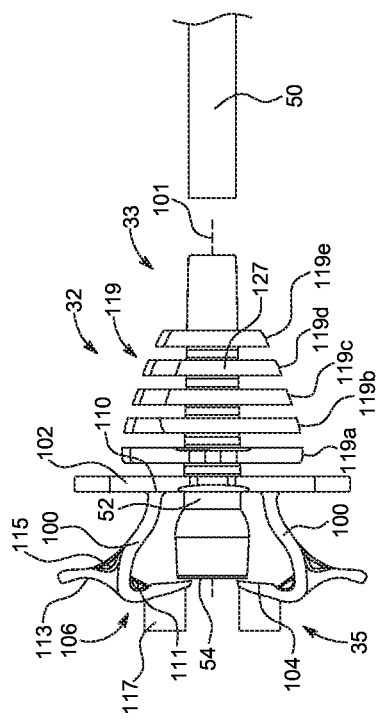
FIG. 42C is a side view of the connector assembly shown in FIG. 42A.
Figure 42A:
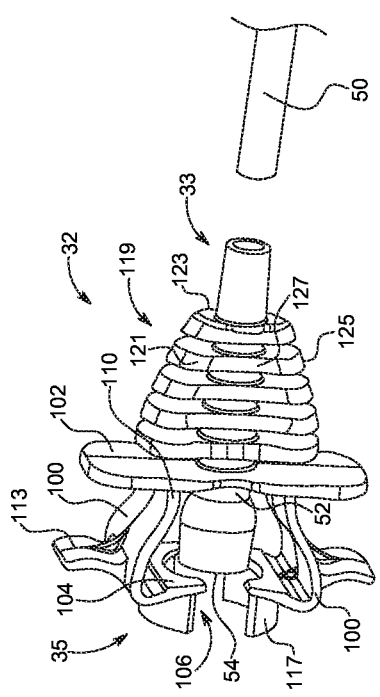
FIG. 42A is a front perspective view of a connector assembly in accordance with another aspect.
Figure 42B:
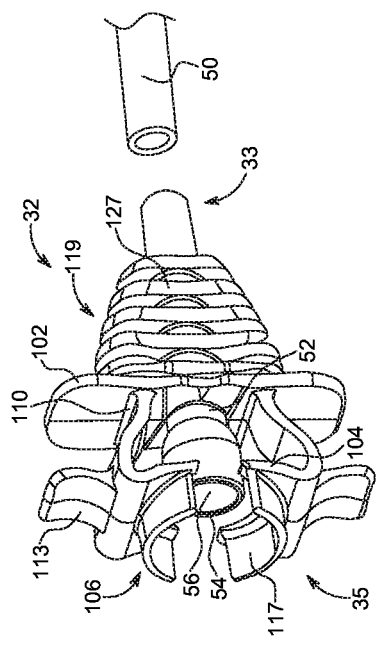
FIG. 42B is a rear perspective view of the connector assembly shown in FIG. 42A.

With reference to FIGS. 42A-42C, a connector assembly 32 is illustrated in accordance with another embodiment. A syringe, such as a syringe 12 shown in FIG. 22, is omitted from FIGS. 42A-42C for clarity. The connector assembly 32 may be connected at its distal end 33 to tubing 50 configured for delivering fluid from the syringe 12. The connector assembly 32 has a body 52 having a longitudinal axis 101 (shown in FIG. 42C) and a fluid fitting 54 at a distal end 35 thereof. The fluid fitting 54 is configured for engaging the inner member 36 of the nozzle 22 of the syringe 12 (shown in FIG. 47). A central fluid channel 56 (shown in FIG. 42B) extends through the body 52 of the connector assembly 32. The central fluid channel 56 is configured for being in fluid communication with the fluid channel 38 of the syringe 12 when the connector assembly 32 is connected to the syringe 12.

Figure 47:
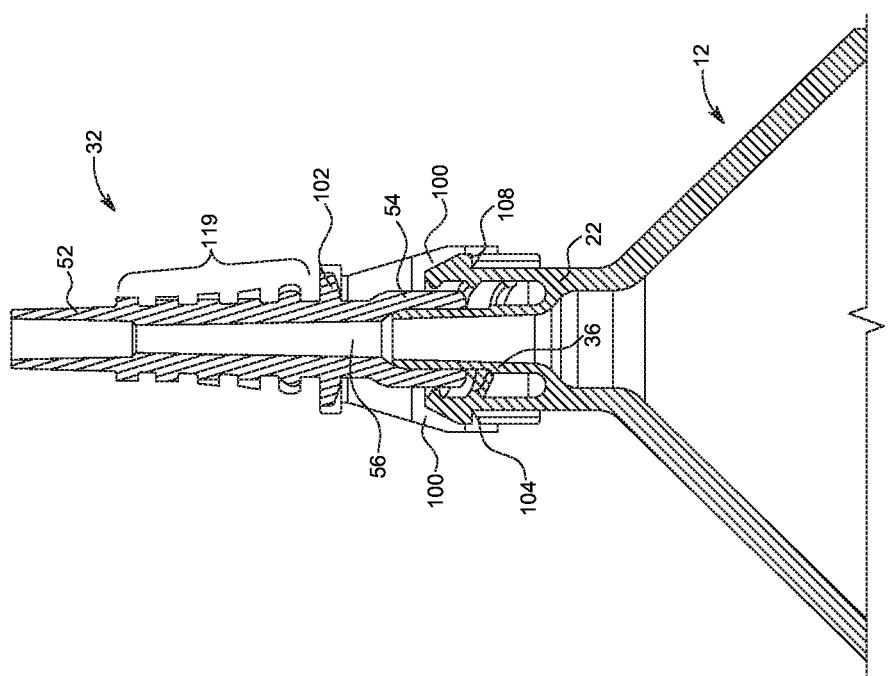
FIG. 47 is a side cross-sectional view of a connector assembly connected with a syringe.

With continued reference to FIGS. 42A-42C, the connector assembly 32 includes at least a pair of flexible, resilient locking arms 100 connected to a radial extension 102 protruding radially outward from the body 52. The radial extension 102 may be formed as a pair of arms protruding radially outward from the body 52. The radial extension 102 may be attached to (removably or non-removably) or monolithically formed with the body 52 of the connector assembly 32. The locking arms 100 extend along at least a portion of the longitudinal length of the body 52 between a distal end 110 connected to the radial extension 102 and a deflectable proximal end 106 opposite to the distal end 110. The locking arms 100 are deflectable in a radial direction toward and away from the body 52. The locking arms 100 are desirably deflectable away from the body 52 of the connector assembly 32 such that the locking arms 100 can be distanced radially from the lip 108 of the syringe 12 in order to allow the fluid fitting 54 to be engaged with the inner member 36 of the nozzle 22 of the syringe 12. The locking arms 100 may be linear, curved, or a combination thereof between an attachment point with the radial extension and a free end opposite the attachment point. Each locking arm 100 has one or more locking elements 104 at its proximal end 106. The one or more locking elements 104 may be directed toward the body 52 of the connector assembly 32 to allow interaction with the syringe 12. With reference to FIG. 47, the locking elements 104 are configured for engaging a lip 108 on a distal end of the nozzle 22 of the syringe 12. One or more reinforcing ribs 111 (shown in FIG. 42C) may provide structural strength to the locking elements 104 in order to prevent the locking elements 104 from bending relative to the body of the locking arm 100.

With continued reference to FIGS. 42A-42C, each locking arm 100 may have one or more releasing tabs 113 at a proximal end 106 thereof. The one or more releasing tabs 113 may face away from the body 52. In some aspects, the one or more releasing tabs 113 may be shaped to correspond to the user's fingers. For example, the one or more releasing tabs 113 may be curved to correspond to a shape of a user's finger. The one or more releasing tabs 113 may have one or more gripping features (not shown) to facilitate handling of the connector assembly 32 as the connector assembly 32 is disconnected from the syringe 12. The one or more releasing tabs 113, when pulled in a radially outward direction, causes the proximal end 106 of the locking arms 100 to be deflected radially outward such that the connector assembly 32 may be removed from the nozzle 22 of the syringe 12. One or more reinforcing ribs 115 (shown in FIG. 42C) may provide structural strength to the one or more releasing tabs 113 in order to prevent the one or more releasing tabs 113 from bending relative to the body of the locking arm 100.

Figure 48A:
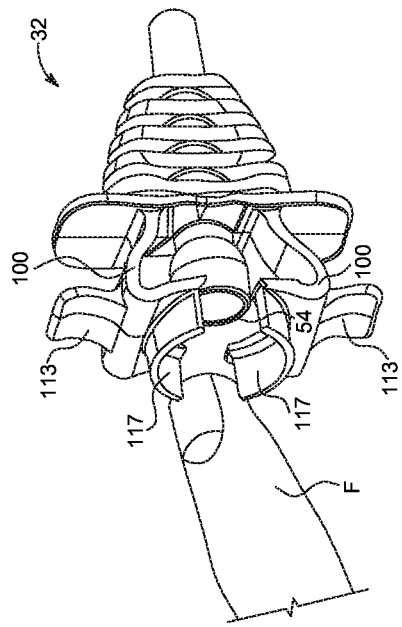
FIGS. 48A-48B are perspective views of a connector assembly showing a protective skirt.
Figure 48B:
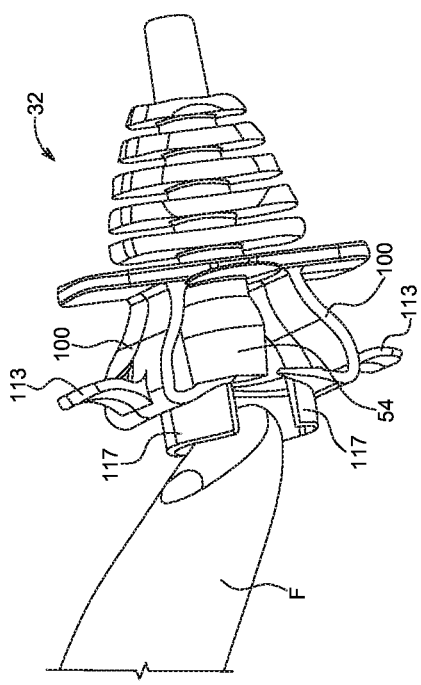

The proximal end 106 of the locking arms 100 may have a protective skirt 117 protruding proximally from the proximal end 106 along a longitudinal axis of the connector assembly 32. The protective skirt 117 may be shaped to surround at least a portion of the fluid fitting 54 and prevent inadvertent contact with the fluid fitting 54 which may contaminate the fluid fitting 54. For example, the protective skirt 117 may be formed a discontinuous (or continuous) ring that surrounds the fluid fitting 54 and is offset longitudinally from a proximal terminal surface of the fluid fitting 54. In this manner, the user's finger F or other objects may be prevented from contacting the fluid fitting 54 and inadvertently contaminating the fluid fitting 54 (shown in FIGS. 48A-48B.

Figure 52A:
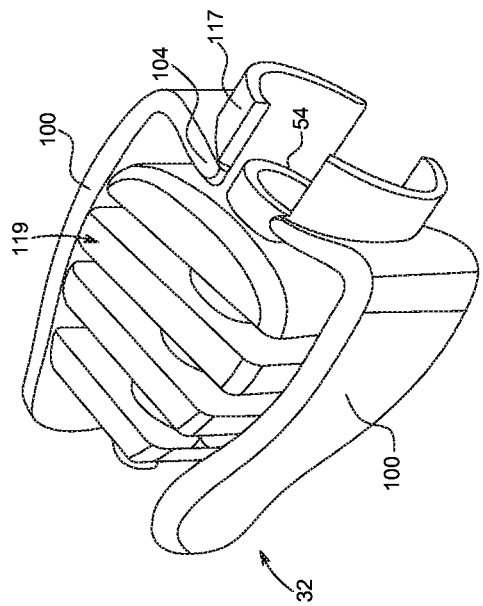
FIG. 52A is a perspective view of a connector assembly in accordance with another aspect.
Figure 52B:
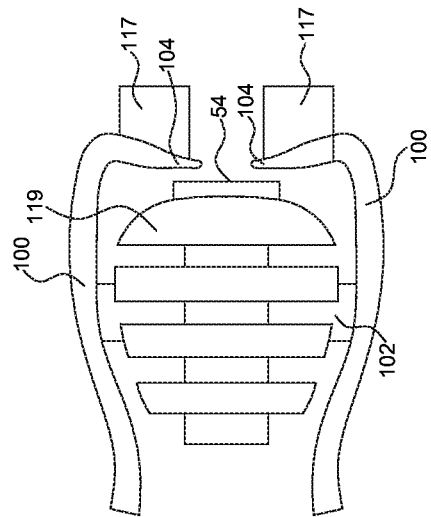
FIG. 52B is a side view of the connector assembly shown in FIG. 52A.

With continued reference to FIGS. 42A-42C and with reference to FIGS. 52A-52B, a gripping tab 119 may be provided for handling the connector assembly 32. In some aspects, the gripping tab 119 may be provided for handling the connector assembly 32 while the connector assembly 32 is being connected to the syringe 12. The gripping tab 119 allows the user to grasp the connector assembly 32 and orient the connector assembly 32 relative to the syringe 12 for connection with the nozzle 22 of the syringe 12. The gripping tab 119 may be attached to (removably or non-removably) or monolithically formed with the body 52 of the connector assembly 32. In some aspects, the gripping tab 119 may be formed as a plurality of individual tabs 119a-119e (shown in FIG. 42C) that protrude radially outward from the body 52. Each of the individual tabs 119a-119e may be axially offset from adjacent tabs in a longitudinal direction of the body 52. The plurality of individual tabs 119a-119e may be formed such that the overall outer shape of the gripping tab 119 expands radially from the distal end of the body 52 toward the proximal end. The space between the individual tabs 119a-119e may be filled with a material that may be co-molded with the gripping tab 119, such as shown in FIGS. 53A-53B and FIGS. 54A-54B. The gripping tab 119 may be shaped such that it has a substantially flattened cross-sectional profile having an oval, rectangular, or other geometric shape. For example, the gripping tab 119 may have a first surface 121 that is separated from a second surface 123 by a lateral surface 125 (shown in FIG. 42A). The first and second surfaces 123 may be wider than the lateral surface 125. At least a portion of the first and/or second surface 121, 123 of the gripping tab 119 may have a depressed area 127 shaped to correspond to a shape of the user's fingers and increase a contact area with the user's fingers. The depressed area 127 may be concavely shaped. The gripping tab 119 is desirably separated axially from the releasing tab 113 in order to separate a portion of the connector assembly 32 that is used for handling the connector assembly 32 during the connection process with the syringe 12 (gripping tab 119) from the portion of the connector assembly 32 that is used to release the connector assembly from the syringe 12 (releasing tab 113).

With reference to FIG. 47, to connect the connector assembly 32 with the syringe 12, the user grasps the connector assembly 32 by the gripping tab 119 and moves the connector assembly 32 toward the nozzle 22 of the syringe 12 until the locking arms 100 may be brought into engagement with the lip 108. Continued movement of the connector assembly 32 in a proximal direction causes the locking arms 100 to spread apart in a radially outward direction relative to the body 52 to allow the locking elements 104 to clear the lip 108. Once the locking elements 104 clear the lip 108, the locking arms 100 move radially inward such that the locking elements 104 engage the syringe 12 below the lip 108. During engagement between the locking elements 104 and the lip 108 of the syringe 12, the fluid fitting 54 on the connector assembly 32 is brought in fluid communication with the inner member 36 on the syringe nozzle 22. In some embodiments, the connector assembly 32 may be connected with the syringe 12 upon application of a proximally-directed force of approximately 5-35 pounds. In other embodiments, the force needed to connect the connector assembly 32 with the syringe 12 may be more or less than 5-35 pounds. It is also contemplated that, to maintain the seal strength at a reduced axial force, surface 56 could include a softer durometer material or a textured surface. In some embodiments, the force needed to connect the connector assembly 32 with the syringe 12 is chosen such that the connector assembly 32 is pushed by the user into engagement with the nozzle 22 of the syringe 12 such that a fluid-tight connection is established between the inner member 36 of the nozzle 22 and the fluid fitting 54 of the connector assembly 32. The connection between the connector assembly 32 and the syringe nozzle 22 may be formed without rotating the connector assembly 32 relative to the syringe nozzle 22.

To remove the connector assembly 32 from the syringe nozzle 22, the locking arms 100 may be moved radially outward relative to the body 52 by engaging the one or more releasing tabs 113 on the proximal end of the locking arms 100 and pulling the one or more releasing tabs 113 in a radially outward direction. Such movement of the locking arms 100 disengages the locking elements 104 from the lip 108 on the syringe nozzle 22. The connector assembly 32 can then be removed from the nozzle 22 by pulling the connector assembly 32 in a distal direction relative to the nozzle 22.

With reference to FIGS. 43A-43C, a connector assembly 32 is illustrated in accordance with another embodiment. The components of the connector assembly 32 shown in FIGS. 43A-43C are substantially similar to the components of the connector assembly 32 described herein with reference to FIGS. 42A-42C. Reference numerals in FIGS. 43A-43C are used to illustrate identical or similar components of the corresponding reference numerals in FIGS. 42A-42C. As the previous discussion regarding the connector assembly 32 generally shown in FIGS. 42A-42C is applicable to the aspect of the present disclosure shown in FIGS. 43A-43C, only the relative differences between the connector assembly 32 shown in FIGS. 43A-43C and the connector assembly 32 shown in FIGS. 42A-42C are discussed hereinafter. A syringe, such as a syringe 12 shown in FIG. 22 or 47, is omitted from FIGS. 43A-43C for clarity.

Figure 51:
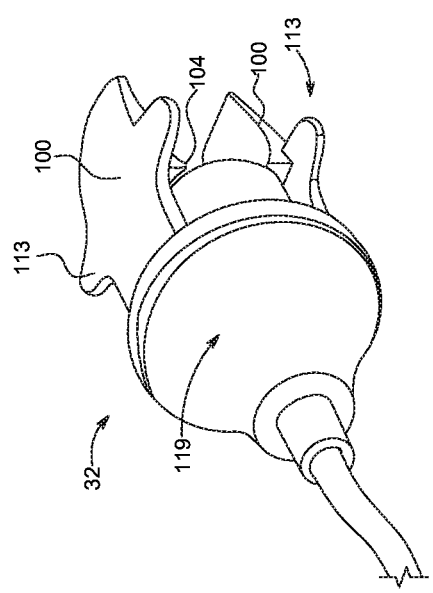
FIG. 51 is a perspective view of a connector assembly in accordance with another aspect.

With reference to FIGS. 43A-43C, the connector assembly 32 includes at least a pair of flexible, resilient locking arms 100 connected to a radial extension 102 protruding radially outward from the body 52. The radial extension 102 may be formed as a ring protruding radially outward from the body 52. The radial extension 102 may be attached to (removably or non-removably) or monolithically formed with the body 52 of the connector assembly 32. A gripping tab 119 may be provided for handling the connector assembly 32 while the connector assembly 32 is being connected to the syringe 12. The gripping tab 119 allows the user to grasp the connector assembly 32 and orient the connector assembly 32 relative to the syringe 12 for connection with the nozzle 22 of the syringe 12. The gripping tab 119 may be attached to (removably or non-removably) or monolithically formed with the body 52 of the connector assembly 32. In some aspects, the gripping tab 119 may be formed as a plurality of individual tabs 119a-119d (shown in FIG. 43C) that protrude radially outward from the body 52. Each of the individual tabs 119a-119d may be axially offset from adjacent tabs in a longitudinal direction of the body 52. Each of the individual tabs 119a-119d may be formed as a ring that protrudes radially outward from the body 52. The plurality of individual tabs 119a-119d may be formed such that the overall outer shape of the gripping tab 119 expands radially from the distal end of the body 52 toward the proximal end. In some aspects, such as shown in FIG. 51, the gripping tab 119 may have a bell or cone shape formed as a solid, continuous surface.

Figure 44C:
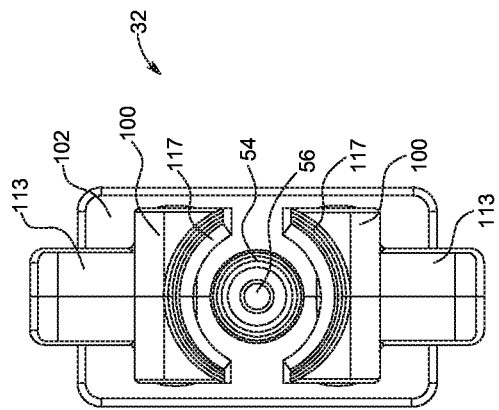
FIG. 44C is a rear view of the connector assembly shown in FIG. 44A.
Figure 44A:
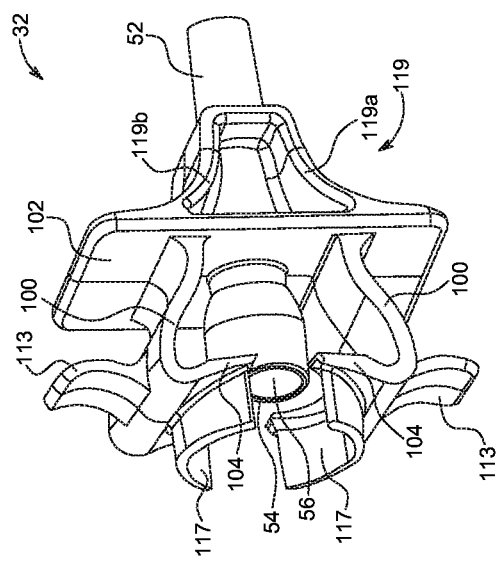
FIG. 44A is a rear perspective view of a connector assembly in accordance with another aspect.
Figure 44B:
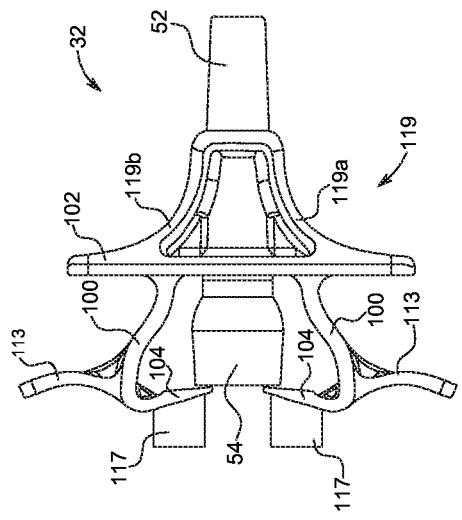
FIG. 44B is a side view of the connector assembly shown in FIG. 44A.

With reference to FIGS. 44A-44C, a connector assembly 32 is illustrated in accordance with another embodiment. The components of the connector assembly 32 shown in FIGS. 44A-44C are substantially similar to the components of the connector assembly 32 described herein with reference to FIGS. 42A-42C. Reference numerals in FIGS. 44A-44C are used to illustrate identical or similar components of the corresponding reference numerals in FIGS. 42A-42C. As the previous discussion regarding the connector assembly 32 generally shown in FIGS. 42A-42C is applicable to the aspect of the present disclosure shown in FIGS. 44A-44C, only the relative differences between the connector assembly 32 shown in FIGS. 44A-44C and the connector assembly 32 shown in FIGS. 42A-42C are discussed hereinafter. A syringe, such as a syringe 12 shown in FIG. 22 or 47, is omitted from FIGS. 44A-44C for clarity.

Figure 57A:
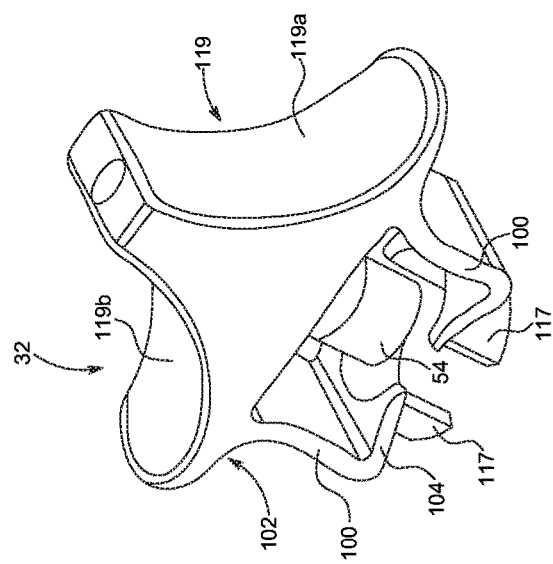
FIG. 57A is a perspective view of a connector assembly in accordance with another aspect.
Figure 57B:
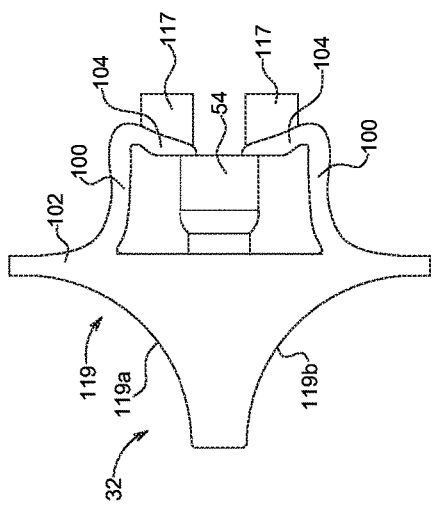
FIG. 57B is a side view of the connector assembly shown in FIG. 57A.

A gripping tab 119 (shown in FIGS. 44A-44B) may be provided for handling the connector assembly 32 while the connector assembly 32 is being connected to the syringe 12. The gripping tab 119 allows the user to grasp the connector assembly 32 and orient the connector assembly 32 relative to the syringe 12 for connection with the nozzle 22 of the syringe 12. The gripping tab 119 may be attached to (removably or non-removably) or monolithically formed with the body 52 of the connector assembly 32. In some aspects, the gripping tab 119 may be formed as a pair of individual tabs 119a-119b that that are connected at one end to the body 52 and at the other end to the radial extension 102 that protrudes radially outward relative to the body 52. In this manner, each of the individual tabs 119a-119b may have a curved or angled shape. The individual tabs 119a-119b may be formed such that the overall outer shape of the gripping tab 119 expands radially from the distal end of the body 52 toward the proximal end. In some aspects, the gripping tab 119 may be shaped to correspond to the user's fingers. For example, the gripping tab 119 may be curved to correspond to a shape of the user's fingers. The gripping tab 119 may have one or more gripping features (not shown) to facilitate handling of the connector assembly 32 as the connector assembly 32 is connected to the syringe 12. FIGS. 57A-57B illustrate a gripping tab 119 with a pair of individual tabs 119a-119b formed to have a curved shape that corresponds to the user's fingers to facilitate handling of the connector assembly 32.

Figure 45C:
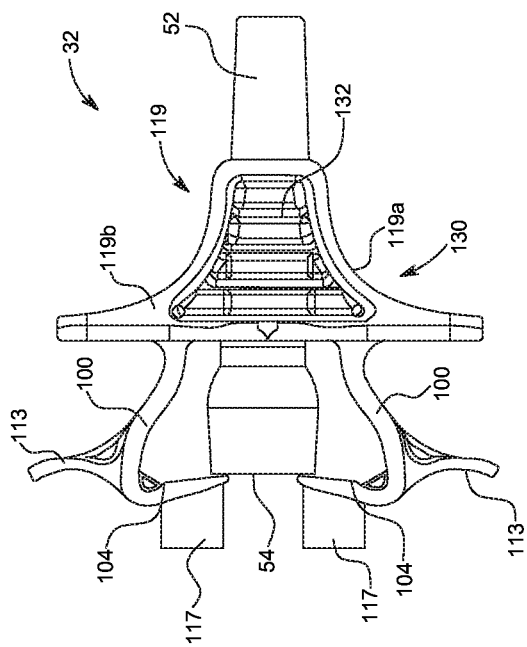
FIG. 45C is a side view of the connector assembly shown in FIG. 45A.
Figure 45A:
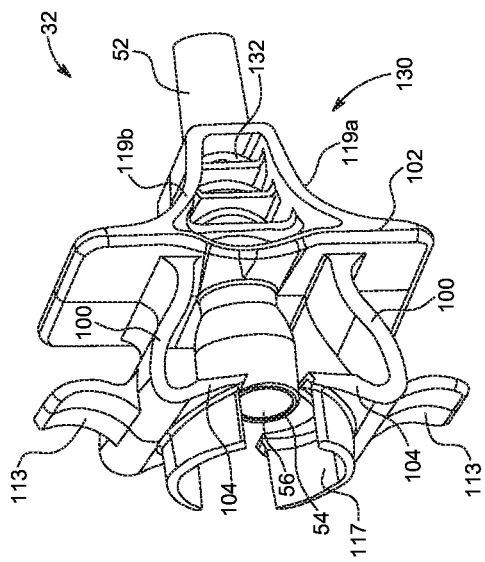
FIG. 45A is a rear perspective view of a connector assembly in accordance with another aspect.
Figure 45B:
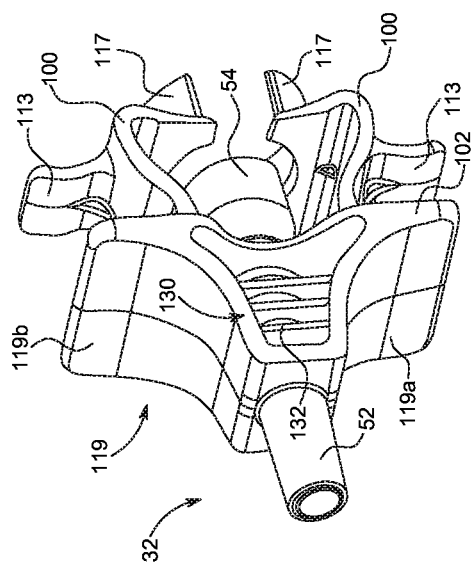
FIG. 45B is a front perspective view of a connector assembly shown in FIG. 45A.

With reference to FIGS. 45A-45C, a connector assembly 32 is illustrated in accordance with another embodiment. The components of the connector assembly 32 shown in FIGS. 45A-45C are substantially similar to the components of the connector assembly 32 described herein with reference to FIGS. 42A-42C. Reference numerals in FIGS. 45A-45C are used to illustrate identical or similar components of the corresponding reference numerals in FIGS. 42A-42C. As the previous discussion regarding the connector assembly 32 generally shown in FIGS. 42A-42C is applicable to the aspect of the present disclosure shown in FIGS. 45A-45C, only the relative differences between the connector assembly 32 shown in FIGS. 45A-45C and the connector assembly 32 shown in FIGS. 42A-42C are discussed hereinafter. A syringe, such as a syringe 12 shown in FIG. 22 or 47, is omitted from FIGS. 45A-45C for clarity.

With reference to FIGS. 45A-45C, the connector assembly 32 has a fluid wicking element 130 that is configured to wick fluid (by capillary action) that may spill from the fluid fitting 54. In some aspects, the fluid wicking element 130 has a plurality of tiered drip flanges 132 separated from each other by a narrow circumferential space defined between any two tiers of drip flanges 132. The fluid wicking element 130 may be monolithically formed with the connector assembly 32, or it may be separately installed onto the connector assembly 32. In some aspects, the fluid wicking element 130 is provided in a space between the tabs 119a-119b and the radial extension 102. The plurality of tiered drip flanges 132 may be formed as a flat plates or planes that are stacked in a spaced apart relationship to define a space therebetween. The drip flanges 132 may be parallel with one another, or they may be angled relative to one another.

The gap or distance between the flat plates is selected such that fluid introduced in the space defined between the plates forms a capillary bridge or fluid bridge. As described with particularity herein, a fluid bridge is formed between two solid surfaces (e.g., flanges, planes, flat plates). The fluid bridge can lead to the appearance of attractive (adhesive) force between the two solid surfaces owing to the decreased pressure inside the fluid bridge and the direct action of the surface tension force exerted around the annulus of the meniscus. The capillary bridge force is oriented normally to the plane of a contact line and consists of contributions from the capillary pressure and surface tension. Any fluid that may spill from the fluid fitting 54 is directed along the body of the fluid fitting 54 and into the fluid wicking element 130 by way of a recess 134 on the radial extension 102. Dripping fluid may accumulate within the fluid wicking element 130 until a maximum fluid volume, defined by a size of the fluid wicking element 130, is accumulated in the gaps between the drip flanges 132. After the maximum fluid volume is accumulated, any additional fluid may flow over the fluid wicking element 130 and down the body of the connector assembly 32.

Although in the example of FIGS. 45A-45C the tiered drip flanges 132 are flat, in an alternative aspect, the tiered drip flanges 132 may be arranged in a winged, corrugated, curved, or other configuration where the drip flanges 132 are angled with respect to a vertical axis but still parallel relative to each other. In yet another aspect, tiered drip flanges 132 may be arranged in a winged, corrugated, curved, or other configuration where the drip flanges 132 are angled with respect to a vertical axis and are not parallel relative to each other.

The gap between the tiered drip flanges 132 may be defined such that a gap width is constant between all drip flanges 132. In other aspects, the gap width may be variable. For example, the gap width may increase, decrease, or be varied arbitrarily between the adjacent drip flanges 132.

Figure 46C:
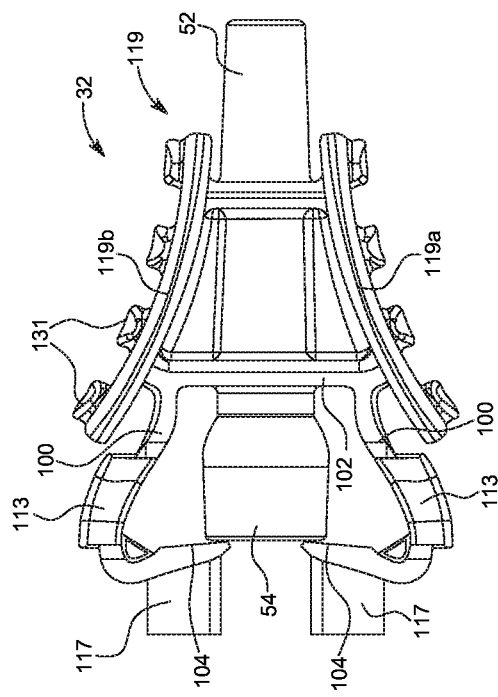
FIG. 46C is a side view of the connector assembly shown in FIG. 46A.
Figure 46A:
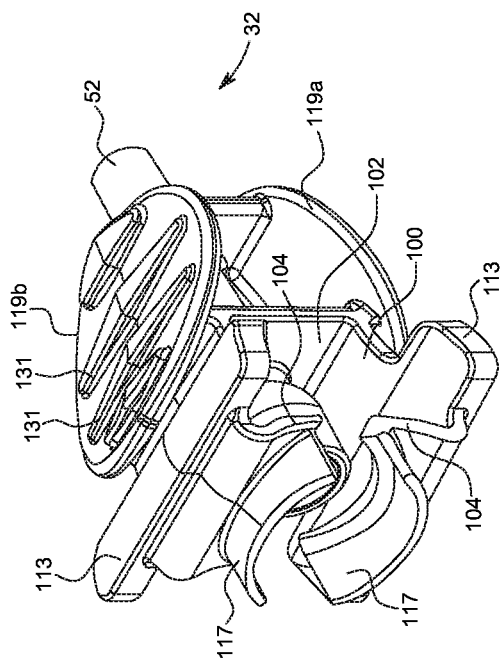
FIG. 46A is a rear perspective view of a connector assembly in accordance with another aspect.
Figure 46B:
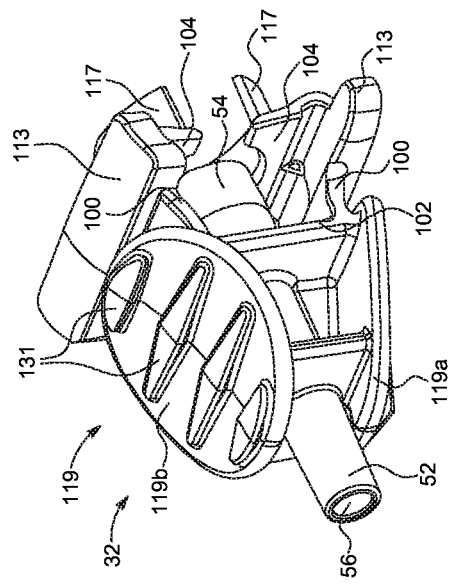
FIG. 46B is a front perspective view of a connector assembly shown in FIG. 46A.

With reference to FIGS. 46A-46C, a connector assembly 32 is illustrated in accordance with another embodiment. The components of the connector assembly 32 shown in FIGS. 46A-46C are substantially similar to the components of the connector assembly 32 described herein with reference to FIGS. 42A-42C. Reference numerals in FIGS. 46A-46C are used to illustrate identical or similar components of the corresponding reference numerals in FIGS. 42A-42C. As the previous discussion regarding the connector assembly 32 generally shown in FIGS. 42A-42C is applicable to the aspect of the present disclosure shown in FIGS. 46A-46C, only the relative differences between the connector assembly 32 shown in FIGS. 46A-46C and the connector assembly 32 shown in FIGS. 42A-42C are discussed hereinafter. A syringe, such as a syringe 12 shown in FIG. 22 or 47, is omitted from FIGS. 46A-46C for clarity.

A gripping tab 119 may be provided for handling the connector assembly 32 while the connector assembly 32 is being connected to the syringe 12. The gripping tab 119 allows the user to grasp the connector assembly 32 and orient the connector assembly 32 relative to the syringe 12 for connection with the nozzle 22 of the syringe 12. The gripping tab 119 may be attached to (removably or non-removably) or monolithically formed with the body 52 of the connector assembly 32. In some aspects, the gripping tab 119 may be formed as a pair of individual tabs 119a-119b that that are connected at one end to the body 52 and at the other end to the radial extension 102 that protrudes radially outward relative to the body 52. In this manner, each of the individual tabs 119a-119b may have a curved or angled shape. The individual tabs 119a-119b may be formed such that the overall outer shape of the gripping tab 119 is round or oval in shape. In some aspects, the gripping tab 119 may be shaped to correspond to the user's fingers. For example, the gripping tab 119 may be curved to correspond to a shape of the user's fingers. The gripping tab 119 may have one or more gripping elements 131 to facilitate handling of the connector assembly 32 as the connector assembly 32 is connected to the syringe 12. The one or more gripping elements 131 may be formed as indicia, such as shown in FIGS. 53A-53B.

Figure 49B:
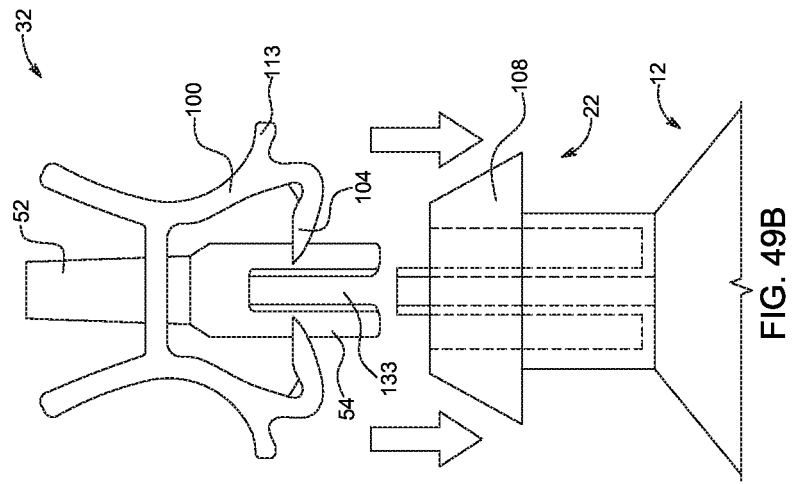
FIG. 49B is a side view of the connector assembly shown in FIG. 49A.
Figure 49A:
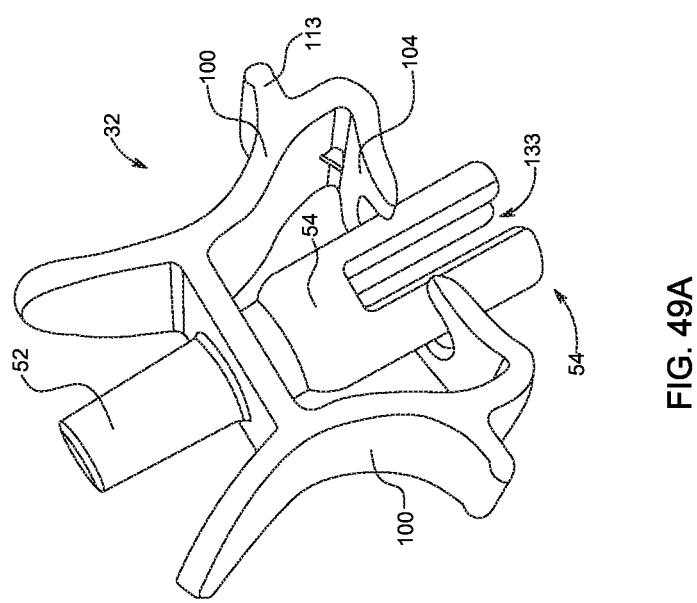
FIG. 49A is a perspective view of a connector assembly in accordance with another aspect.

FIGS. 49A-57B illustrate various additional embodiments of the connector assembly 32. With reference to FIGS. 49A-49B, the connector assembly 32 may have a fluid fitting 54 that extends proximally relative to a terminal point of the locking arms 100. In some aspects, the fluid fitting 54 may have a slit 133 extending along a longitudinal axis of the connector assembly 32. The fluid fitting 54 may guide the connector assembly 32 toward the nozzle 22 of the syringe 12 (shown in FIG. 49B) in a coaxial orientation if the connector assembly 32 is attempted to be inserted at angle relative to the nozzle 22 of the syringe 12.

Figure 50:
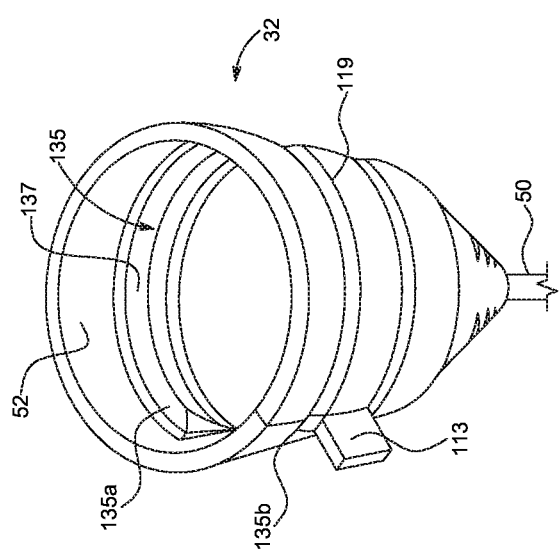
FIG. 50 is a perspective view of a connector assembly in accordance with another aspect.

With reference to FIG. 50, the connector assembly 32 may be formed as a substantially annular or ring-shaped element with a circumferential tab 135. A first end 135a of the circumferential tab 135 is attached to a sidewall of the connector assembly 32 while a second end 135b of the circumferential tab 135 extends circumferentially around an interior of the connector assembly 32 and is deflectable radially relative to the first end 135a. An inner surface of the circumferential tab 135 has a locking tab 137 that interacts with the nozzle 22 of the syringe 12 (shown in FIG. 47). To connect the connector assembly 32 to the syringe 12, the user grasps the body 52 of the connector assembly 32 and urges the connector assembly 32 with a proximally-directed force onto the nozzle 22. As the connector assembly 32 is moved in a proximal direction relative to the nozzle 22, the circumferential tab 135 is deflected radially outward such that the locking tab 137 clears the lip 108 on the nozzle 22. Once the locking tab 137 clears the lip 108 on the nozzle 22, the circumferential tab 135 springs back to its initial position due to an elastically resilient property of the body of the circumferential tab 135. To remove the connector assembly 32 from the nozzle 32, the circumferential tab 135 is manually deflected in a radially outward direction by a user, for example by pushing on releasing tab 113 at the second end 135b of circumferential tab 135.

With reference to FIGS. 53A-53B, the locking arms 100 may be formed without a release feature. In such aspects, the locking arms 100, once connected with the syringe 12, cannot be removed from the syringe 12. To connect the connector assembly 32 to the syringe 12, the connector assembly 32 may be pushed onto the nozzle 22 of the syringe 12, as described herein. After use, the connector assembly 32 and the syringe 12 may be disposed.

Figure 55A:
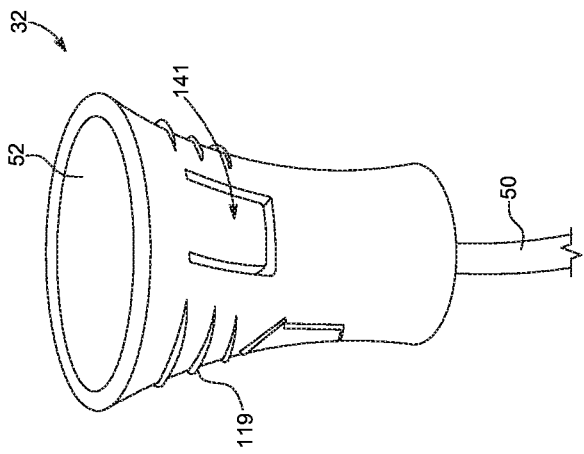
FIG. 55A is a perspective view of a connector assembly in accordance with another aspect.
Figure 55B:
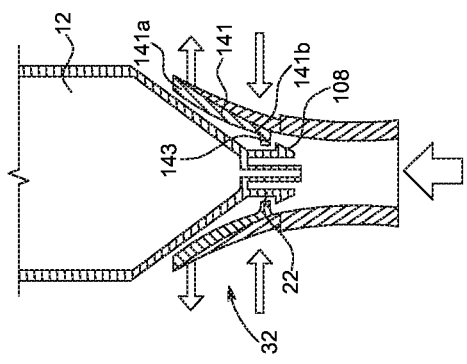
FIG. 55B is a side view of the connector assembly shown in FIG. 55A.

With reference to FIGS. 55A-55B, the connector assembly 32 may be formed as a substantially annular or ring-shaped element with a longitudinal tab 141. With reference to FIG. 55B, a first end 141a of the longitudinal tab 141 is attached to a sidewall of the connector assembly 32 while a second end 141b of the longitudinal tab 141 extends proximally relative to the first end 141a and is deflectable radially relative to the first end 141a. An inner surface of the longitudinal tab 141 has a locking tab 143 formed at the second end 141b that interacts with the nozzle 22 of the syringe 12 (shown in FIG. 55B). To connect the connector assembly 32 to the syringe 12, the user grasps the body 52 of the connector assembly 32 and urges the connector assembly 32 with a proximally-directed force onto the nozzle 22. As the connector assembly 32 is moved in a proximal direction relative to the nozzle 22, the second end 141b of the longitudinal tab 141 is deflected radially outward such that the locking tab 143 clears the lip 108 on the nozzle 22. Once the locking tab 137 clears the lip 108 on the nozzle 22, the second end 141b of the longitudinal tab 141 springs back to its initial position due to an elastically resilient property of the body of the longitudinal tab 141. In some aspects, the connector assembly 32 may be non-removably or removably connected to the syringe 12.

Figure 56A:
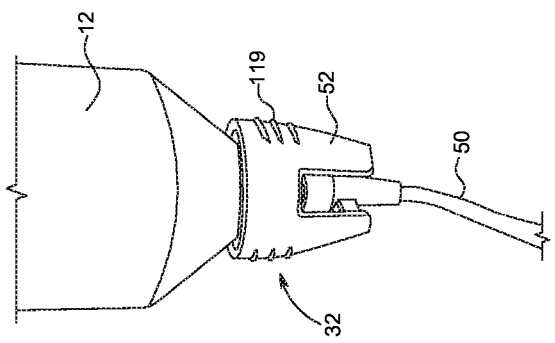
FIG. 56A is a perspective view of a connector assembly in accordance with another aspect.
Figure 56B:
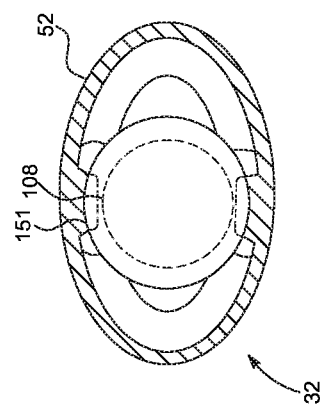
FIG. 56B is a top cross-sectional view of the connector assembly shown in FIG. 56A in a first position.
Figure 56C:
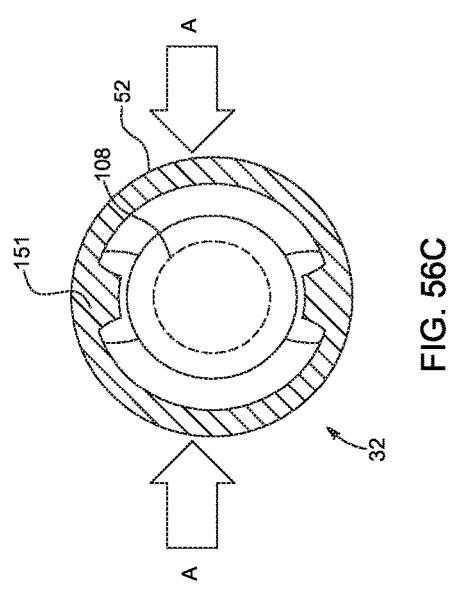
FIG. 56C is a top cross-sectional view of the connector assembly shown in FIG. 56A in a second position.

With reference to FIGS. 56A-56C, the connector assembly 32 may be formed as a substantially annular or ring-shaped element. At least a portion of the body 52 of the connector assembly 32 may be deformable from a first position to a second position to allow the connector assembly 32 to be connected to and disconnected from the syringe 12. For example, the body 52 may have a substantially oval shape such that the locking tabs 151 on an inner surface of the body 52 engage with a lip 108 on the syringe 12. To release the connector assembly 32 from the syringe 12, at least a portion of the body 52 may be compressed, such as by a radially directed force in a direction of arrows A in FIG. 56C, to deform the body 52 from a substantially oval shape (shown in FIG. 56B) to a substantially circular shape (shown in FIG. 56C) to allow the locking tab 151 to disengage from the lip 108 on the syringe 12. In various other aspects, the body 52 can be deformable to a variety of other shapes, such as from a first circular position to a second oval position.

With reference to FIGS. 58-72, a fluid transfer assembly 300 is illustrated in accordance with another aspect. The fluid transfer assembly 300 is used, in this aspect, to connect a first container, such as a syringe 12, and a second container 302 as described herein, using a fill adapter 304 configured to deliver fluid from the second container 302 to the syringe 12. The second fluid container 302 has a generally cylindrical barrel formed from glass, metal or a suitable medical-grade plastic. The barrel has a proximal end and a distal end, with a sidewall extending therebetween along a longitudinal axis. A fluid delivery section, such as a nozzle, extends from the distal end of the barrel. The barrel has an outer surface and an inner surface that defines an interior volume configured for receiving a fluid therein. With specific reference to FIG. 63, the distal end of the second fluid container 302 may include a connection interface, such as a piercable septum 320, for connecting with the fill adapter 304. When pierced, the fill adapter 304 of the fluid transfer assembly 300 facilitates the transfer of fluid from the second fluid container 302 to the syringe 12. It is also contemplated that a rolling diaphragm syringe 600 such as the one shown in FIG. 83 and described hereinabove may also be used with the fill adapter 304.

Figure 59:
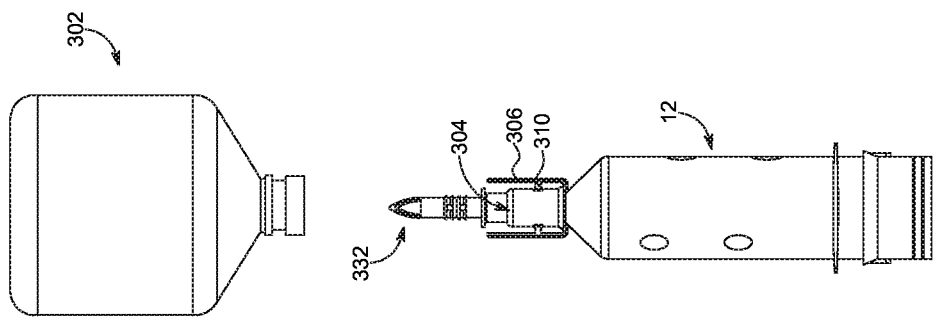
FIG. 59 is a front view of the syringe and the connector assembly of FIG. 58 assembled apart from the fluid container.
Figure 58:
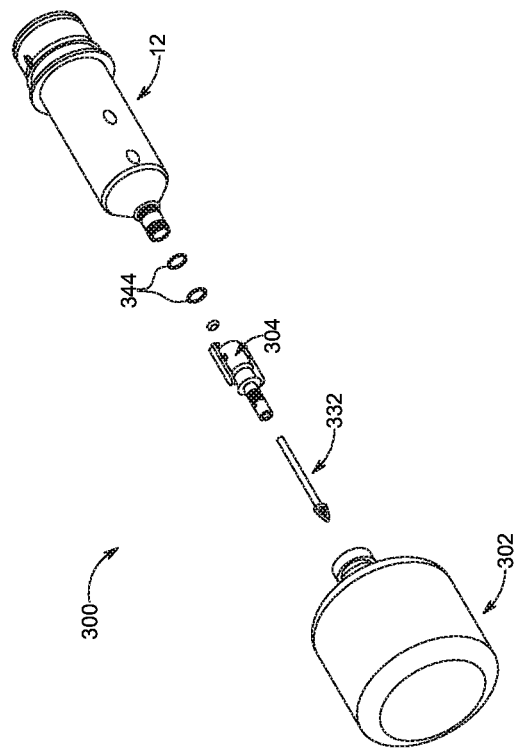
FIG. 58 is an exploded perspective view of a syringe, a connector system, and a fluid container in accordance with another aspect.
Figure 61:
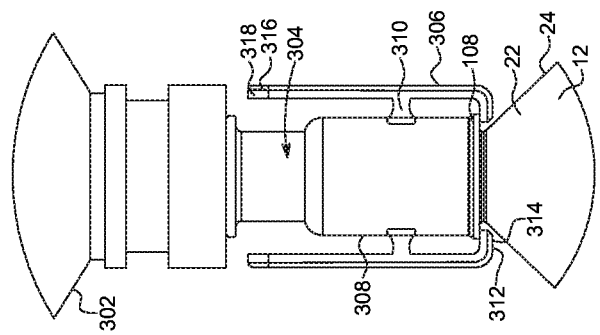
FIG. 61 is an isolated view of the connector system of FIG. 58 connected to the syringe and the fluid container.
Figure 60:
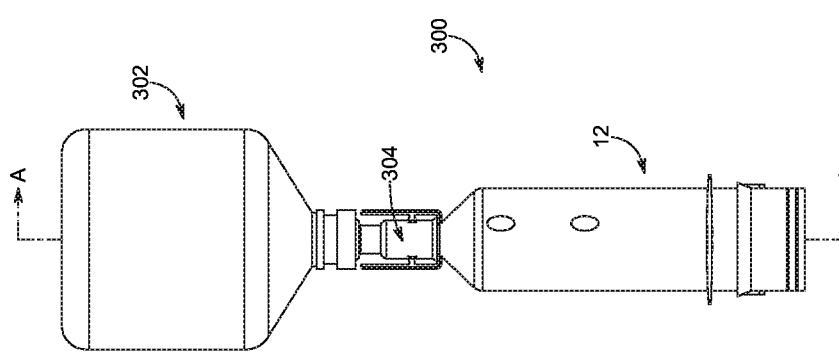
FIG. 60 is a front view of the syringe, the connector assembly, and the fluid container of FIG. 58 assembled.

With specific reference to FIG. 59, the fill adapter 304 may include at least a pair of flexible, resilient gripping arms 306 connected to a body 308 by a radial extension 310. The gripping arms 306 extend along at least a portion of the longitudinal length of the body 308. The gripping arms 306 are deflectable in a radial direction about the radial extension 310 toward and away from the body 308. The gripping arms 306 are desirably deflectable away from the body 308 such that the gripping arms 306 are distanced radially from the outer surface 24 of the syringe 12 in order to allow the body 308 to slide over a lip 108 located on the outer surface 24 of the nozzle 22. Each gripping arm 306 has one or more gripping elements 312 at a proximal end 314. The gripping elements 312 may be oriented to face toward the body 308. The one or more gripping elements 312 are configured for engaging the lip 108 when the body 308 is positioned over the nozzle 22. The gripping arms 306 also have a pressing surface 316 at a distal end 318 and facing away from the body 308. The pressing surface 316, when pressed between the user's fingers, causes the proximal end 314 of the gripping arms 306 to be deflected radially outward, into a first position, such that the fill adapter 304 may be inserted into the nozzle 22 of the syringe 12. When the force on the pressing surface 316 is released, the gripping elements 312 move back into a second position, towards the body 308 and engage the lip 108. After the transfer of fluid from the second fluid container 302 to the first fluid container 12 is complete, the user may apply force to the pressing surface 316 to cause the proximal end 314 of the gripping arms 306 to deflect radially outwards away from the lip 108, so that the fill adapter 304 may be disengaged from the syringe nozzle 22.

Figure 63:
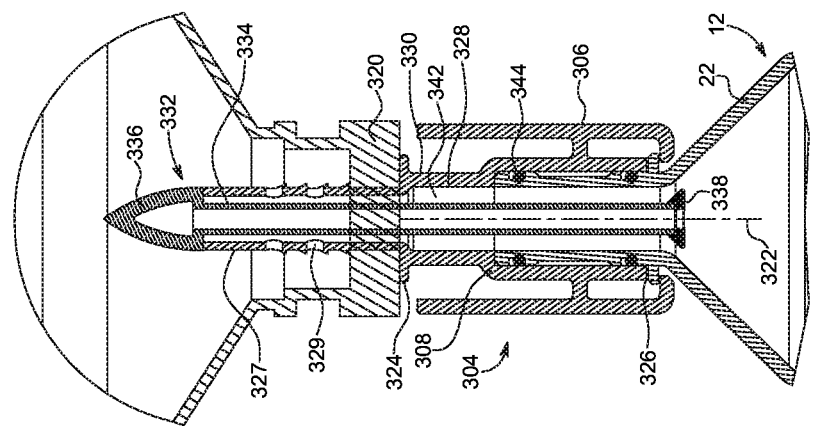
FIG. 63 is an isolated cross-sectional view of the assembly of FIG. 60.
Figure 62:
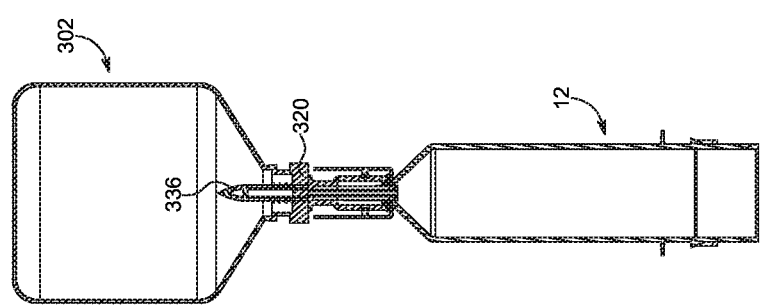
FIG. 62 is a cross-section view of the assembly of FIG. 60 along line A-A.
Figure 65:
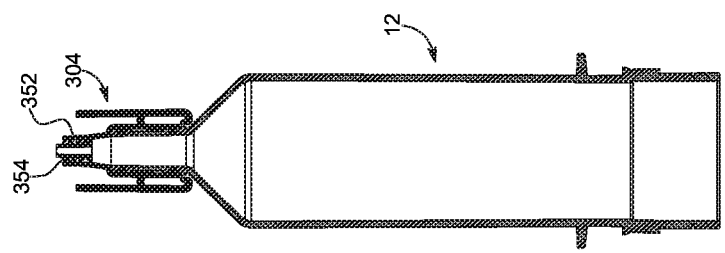
FIG. 65 is a cross-sectional view of an alternate aspect of an assembly of FIG. 60.

With specific reference to FIG. 63, the body 308 of the fill adapter 304 has a generally cylindrical shape and is formed from glass, metal or a suitable medical-grade plastic. The body 308 has a longitudinal axis 322, a distal end 324, and a proximal end 326 configured to releasably connect to the nozzle 22. The body 308 further includes an inner and outer sidewall 328 and 330 extending between the proximal end 326 and the distal end 324 along the longitudinal axis 322. The inner sidewall 328 is configured to interface with the outer surface of the nozzle 22. A proximal portion of the body 308 includes a fluid transfer body 327 that extends from the distal end 324 of the body 308. The fluid transfer body 327 has a diameter smaller than an outer diameter of the body 308. The fluid transfer body 327 defines a passageway configured to receive a piercing member 332, described below. The fluid transfer body 329 may define at least one aperture 329 to permit fluid to flow therethrough. In one aspect, a plurality of apertures 329 are circumferentially spaced along at least a length of the fluid transfer body 329.

With specific reference to FIG. 63, the body 308 and fluid transfer body 327 removably receive a piercing member 332 configured for penetrating the piercable septum 320 of the second fluid container 302. The piercing member 332 has a generally cylindrical body 334, a piercing point 336 located on a distal end, and a flared base 338, flaring radially away from the longitudinal axis, located on a proximal end. With specific reference to FIG. 63, when received within the body 308 of the fill adapter 304, the body 306 of the fill adapter 304 surrounds the body 334 of the piercing member 332 and the piercing point 336 may extend beyond the distal end, while the flared base 338 extends toward the proximal end and into the nozzle 22. The longitudinal axis of the piercing member 332 may be coaxial with the longitudinal axis 322 of the body 308.

Figure 64:
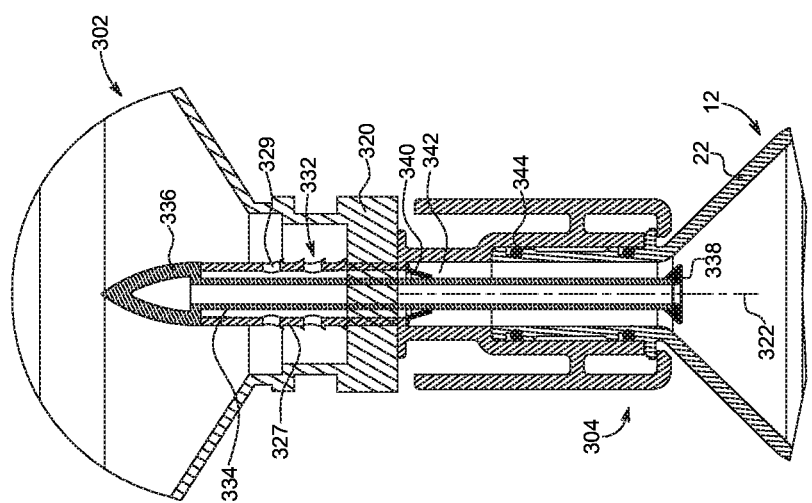
FIG. 64 is a cross-section isolated view of the assembly of FIG. 60 including the use of a deflectable seal.
Figure 67:
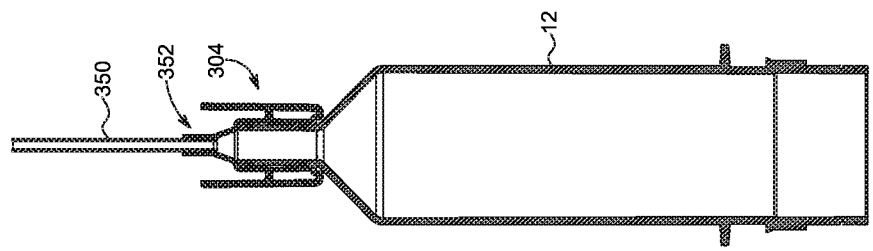
FIG. 67 is a cross-sectional view of the assembly of FIG. 65 showing tubing connected to the connector assembly.
Figure 66:
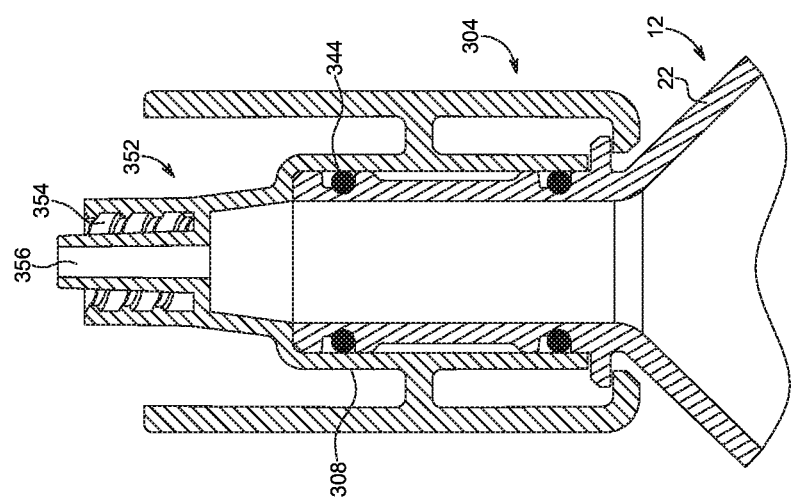
FIG. 66 is an isolated cross-sectional view of the assembly of FIG. 65.
Figure 69:
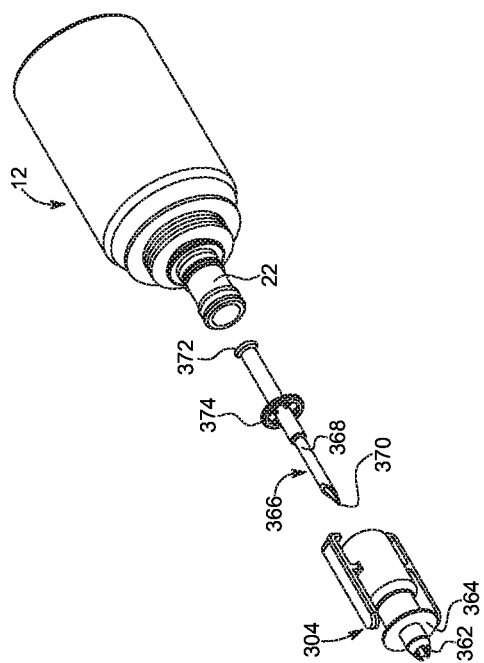
FIG. 69 is an exploded perspective view of a syringe and a connector system in accordance with another aspect.
Figure 68:
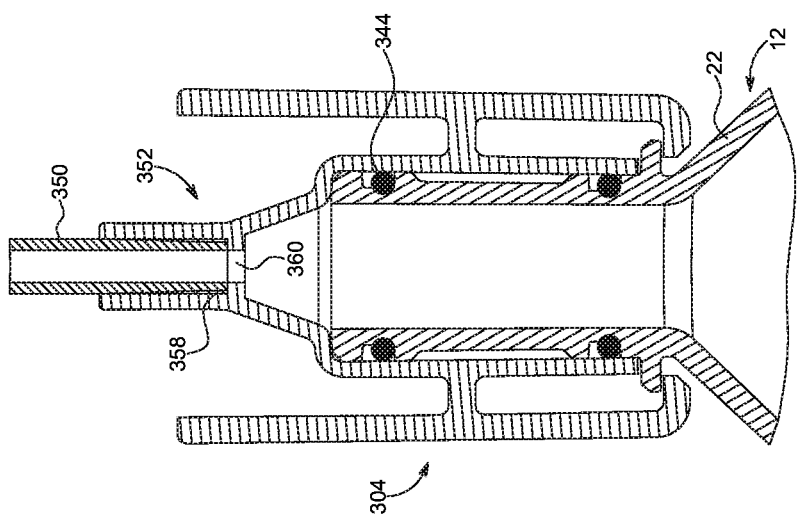
FIG. 68 is an isolated cross-sectional view of the assembly of FIG. 67.
Figure 71:
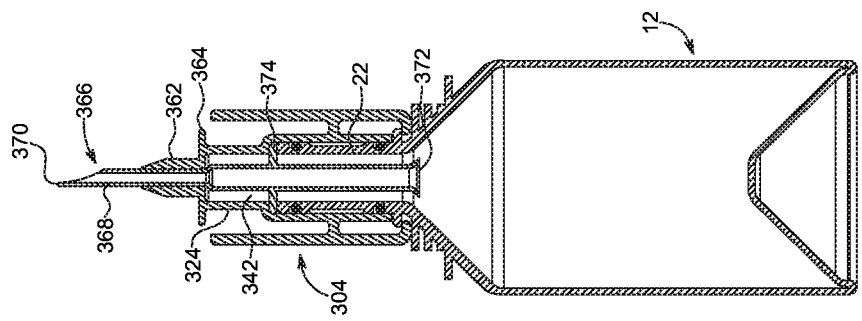
FIG. 71 is a cross-sectional view of the syringe and the connector system of FIG. 70 along line B-B.
Figure 70:
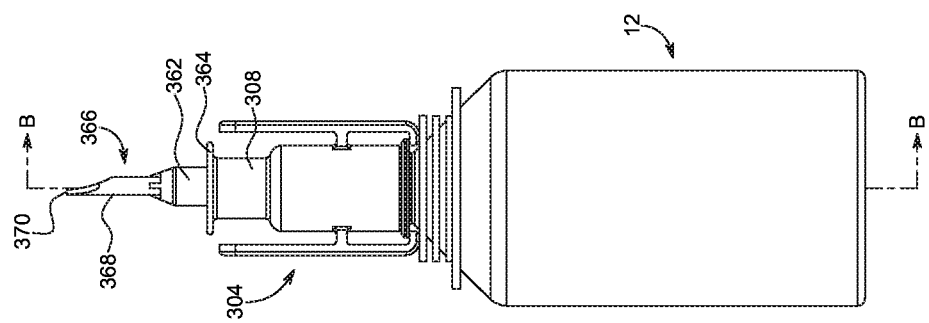
FIG. 70 is a front view of the syringe and connector system of FIG. 69 assembled.

With specific reference to FIG. 64, in another aspect, a deflectable seal 340 may be formed within a passageway 342 defined by the body 308 to prevent fluid flow from the syringe 12 to the second fluid container 302 via the passageway 342. The deflectable seal 340 may be a flap extending inwards towards the flared base 338 of the piercing member 332 until it contacts the exterior of the passageway 342. Thus, the deflectable seal 340 permits fluid to flow in only one direction. The deflectable seal 340 permits fluid flow from the distal end of the piercing member 332 to the proximal end of the piercing member 332 while preventing fluid flow in the opposite direction. With continued reference to FIG. 64, at least one sealing ring 344 may be provided in recesses formed in the nozzle 22 of the syringe 12. In another aspect, two sealing rings 344 are provided on the nozzle 22. The sealing rings 344 assist in preventing fluid leakage between nozzle 22 and body 308 of the fluid adapter 304.

In another embodiment, and with specific reference to FIGS. 65-68, the piercing member 332 is removed and tubing 350 may be inserted to create a fluid path connecting the syringe 12 to a patient. With specific reference to FIGS. 66 and 68, the piercing member 332 may be removed and replaced with a cap 352 housing a female threading 354 member of a luer lock. In other aspects, the arrangement of the female threading 354 and a male member (not shown) may be reversed. In such aspects, the male elements may be provided on the nozzle cap 352, while the tapering female threading 354 may be provided on the connective tubing 350. The nozzle cap 352 may be formed integral with the body 308 of the fluid adapter 304. In this aspect, the fluid transfer body 327 is removed from the fluid adapter 304. The nozzle cap 352 defines a passageway 356 that permits transfer of fluid from the syringe 12 to the tubing 350. In another aspect shown in FIG. 68, the nozzle cap 352 does not include the female threading 354, but instead defines a receiving portion 358 that receives the connective tubing 350. The connective tubing 350 may be held in the receiving portion 358 by a friction fit, welded connection, adhesive, or molding to one another. An aperture 360 is defined in a proximal end of the receiving portion 358 to establish fluid communication between the syringe 12 and the connective tubing 350. In this arrangement, fluid from the syringe 12 flows though the nozzle 22 and into the connective tubing 350 to the patient.

With reference to FIGS. 69-72, another aspect of the fluid adapter 304 is described. In this aspect, the fluid adapter 304 is substantially the same as that shown in FIGS. 58-64, but does not include the fluid transfer body 327. Instead, a protruding member 362 and a flange 364 are formed on the distal end 324 of the body 308. The flange 364 is configured to abut a fluid container (not shown) when the adapter 304 is connected thereto. The protruding member 362 defines a passageway that extends into the passageway 342 defined by the body 308.

The adapter 304 also includes a piercing member 366 that is slidably received within the body 308 and extends through the passageway defined by the protruding member 362. The piercing device 366 has a generally cylindrical body 368, a piercing point 370 located on a distal end, and a flared base 372, flaring radially away from a longitudinal axis of the body 368, located on a proximal end. With specific reference to FIG. 72, when received within the body 308 of the fill adapter 304, the body 306 of the fill adapter 304 surrounds the body 368 of the piercing device 366 and the piercing point 370 may extend beyond the distal end of the protruding member 362, while the flared base 372 extends toward the proximal end of the body 308 and into the nozzle 22. The longitudinal axis of the piercing device 366 may be coaxial with the longitudinal axis 322 of the body 308. The piercing device 366 also includes a flange 374 formed at an intermediate location on the body 368. The flange 374 extends circumferentially around the outer surface of the body 368.

Figure 72:
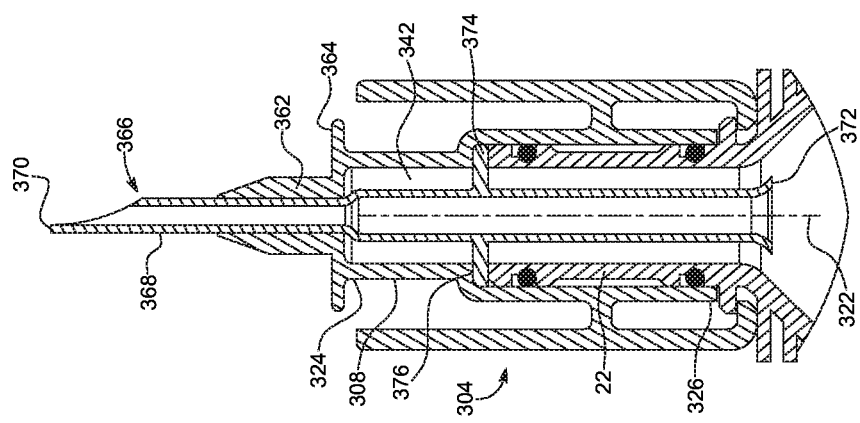
FIG. 72 is an isolated cross-sectional view of the syringe and the connector system of FIG. 70.

With reference to FIG. 72, to assembly the piercing device 366 within the body 308 of the fluid adapter 304, the piercing point 370 of the piercing device 366 is inserted into the proximal end 326 of the body 308. The piercing device 366 is inserted through the passageway 342 defined by the body 308 and the passageway defined by the protruding member 362. Insertion of the piercing device 366 into the body 308 is stopped upon the flange 374 of the piercing device 366 abutting a step 376 defined by an inner surface of the body 308. The step 376 prevents further insertion of the piercing device 366 into the body 308 so that the piercing device 366 extends from the protruding member 362 a predetermined distance. The fluid adapter 304 is then fit onto the nozzle 22 of the syringe 12 as described above. As shown in FIG. 72, after the fluid adapter 304 has been fit onto the nozzle 22, the flange 374 of the piercing device 366 is held between a distal end of the nozzle 22 and the step 376 defined by the body 308.

Figure 73:
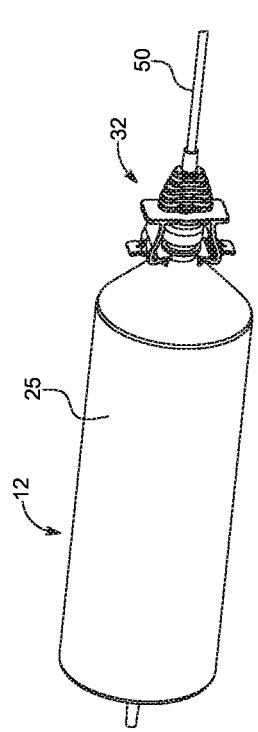
FIG. 73 is a side perspective view of a syringe and connector system in accordance with another aspect.
Figure 74:
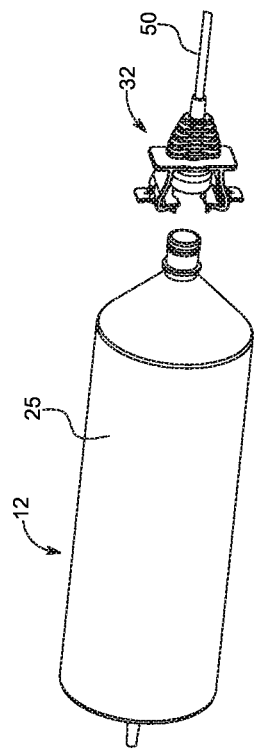
FIG. 74 is a side perspective view of the syringe and connector system of FIG. 73 disconnected from one another.

With reference to FIGS. 73 and 74, a use of the connector assembly 32 of FIGS. 42A-42C is shown. The connector assembly 32 may be connected to a syringe 12 according to the method described above and to tubing 50. In this aspect, the syringe 12 is for use with a fluid injector (not shown) and generally includes a hollow body that includes a forward or distal end configured for connection to the connector assembly 32, a rearward or proximal end, and a flexible sidewall 25, such as a rolling diaphragm, extending therebetween. In use, the proximal end is configured for insertion into the throughbore of a pressure jacket (not shown) such that the sidewall 25 is surrounded by the interior surface of the pressure jacket. At least a portion of the distal end of the syringe 12 may be exposed from a distal end of the pressure jacket. In some examples, the syringe 12 may be formed using a blow-molding technique. In other examples, the syringe 12 may be injection molded. The sidewall 25 of the syringe 12 defines a soft, pliable or flexible, yet self-supporting body that is configured to unroll and roll in upon itself as a rolling diaphragm under the action of a drive member from a fluid injector (not shown) driven against the proximal end of the syringe 12. In particular, the sidewall 25 of the syringe 12 is configured to roll such that its outer surface is folded and inverted in a radially inward direction as the drive member is moved in a distal direction, and unroll and unfold in the opposite manner in a radially outward direction as the drive member is retracted in a proximal direction. Examples of such syringes 12 are described in International Patent Application Publication No. WO 2015/164783, the disclosure of which is hereby incorporated in its entirety by reference.

Figure 75:
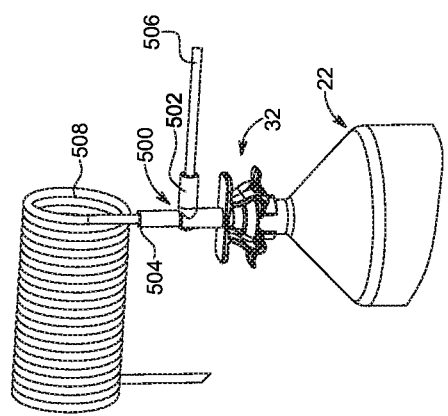
FIG. 75 is a front perspective view of a syringe, a connector system, and a tubing manifold in accordance with another aspect.
Figure 76:
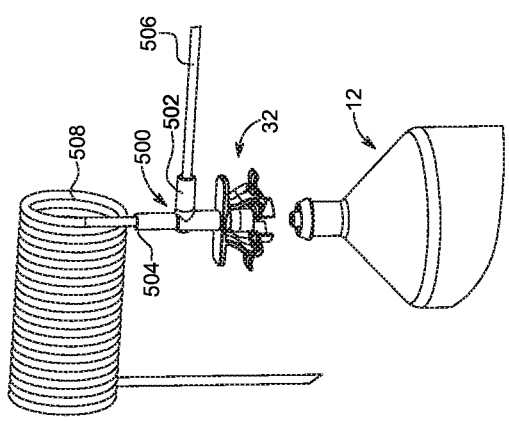
FIG. 76 is a front perspective view of the syringe, the connector system, and the tubing manifold of FIG. 75 disconnected from one another.

With reference to FIGS. 75 and 76, a use of the connector assembly 32 of FIGS. 42A-42C is shown. In this aspect of the connector assembly 32, the gripping tab 119 has been removed such that only a portion of the body 52 extends distally from the radial extension 102. A manifold 500 may be fit onto the portion of the body 52 that extends distally from the radial extension 102. The manifold 500 may be held on the connector assembly 32 by a friction fit, a welded connection, an adhesive, or by molding the two components to one another. In another aspect, the manifold 500 could be integrally formed with the connector assembly 32. The manifold 500 includes two ports 502, 504 configured to receive tubing 506, 508 to transfer fluid to and/or from the syringe 12 to a patient. In one aspect, the ports 502, 504 are arranged substantially perpendicular to one another. It is also contemplated that more than two ports may be provided on the manifold 500. The connector assembly 32 is connected to and/or removed from the syringe 12 according to the methods described above to establish or prevent, respectively, fluid communication between the syringe 12 and the tubing 506, 508.

Figure 78:
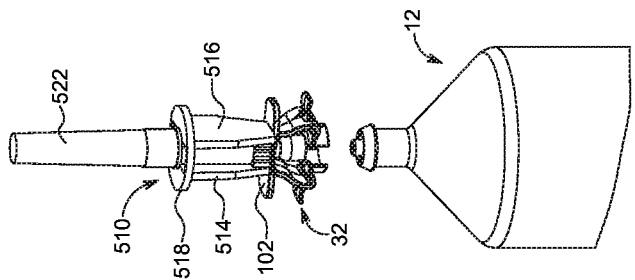
FIG. 78 is a front perspective view of the syringe and connector system of FIG. 77 disconnected from one another.
Figure 77:
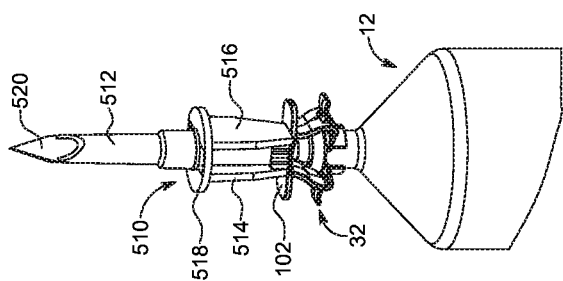
FIG. 77 is a front perspective view of a syringe and connector system in accordance with another aspect.

With reference to FIGS. 77-78, another use of the connector assembly 32 of FIGS. 42A-42C is shown. In this aspect of the connector assembly 32, the gripping tab 119 has been removed. In place of the gripping tab 119, a piercing member clip 510 is provided on the radial extension 102. In one aspect, the piercing member clip 510 includes a spike member 512 for piercing a septum or seal of a fluid container. The piercing member clip 510 may include a pair of arms 514, 516 that extend distally from the radial extension 102. A flange 518 is provided on a distal end of the arms 514, 516 and defines an aperture configured to receive the spike member 512 that extends distally from the radial extension 102 through the aperture. The spike member 512 and the proximal ends of the arms 514, 516 are connected to the radial extension 102 using a welded connection, an adhesive, or a fastening arrangement, or by molding the components integrally with one another as a single-piece component. The spike member 512 defines a passageway 520 that extends from a proximal end to a distal end of the spike member 512. During use, the connector assembly 32 is connected to and/or removed from the syringe 12 according to the methods described above to establish and prevent, respectively, fluid communication between the syringe 12 and the spike member 512. The spike member 512 is then pierced into a second fluid container to establish fluid communication between the syringe 12 and the second container. A cap 522 is also removably provided on the piercing member clip 510 to cover the spike member 512 when not in use to prevent inadvertent contact with the spike member 512.

Figure 79:
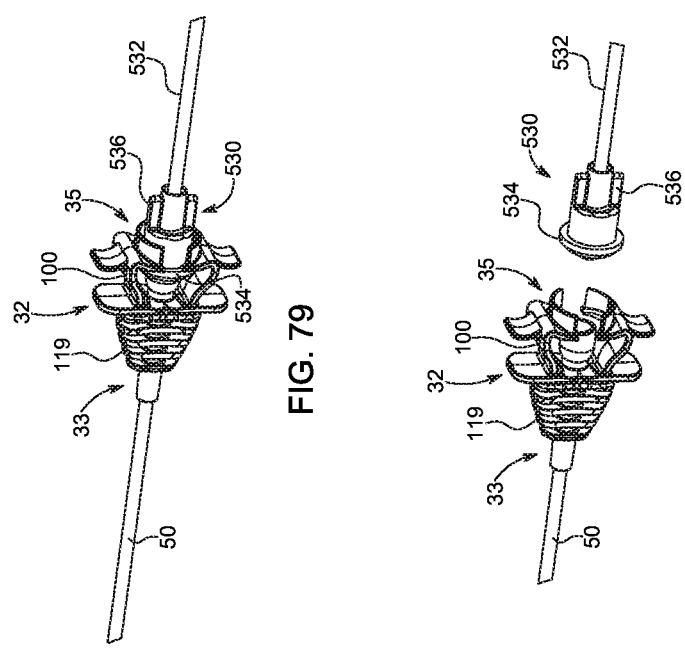
FIG. 79 is a side perspective view of a connector system and tubing connection in accordance with another aspect.
Figure 80:
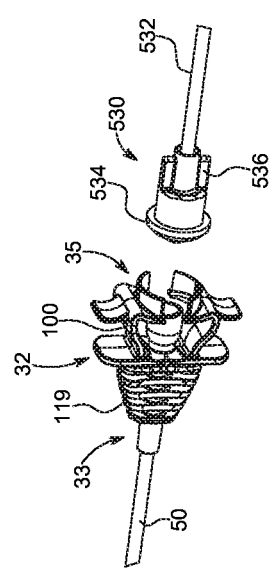
FIG. 80 is a side perspective view of the connector system and tubing connection of FIG. 79 disconnected from one another.

With reference to FIGS. 79-80, another use of the connector system 32 of FIGS. 42A-42C is shown. As described above, tubing 50 is removably connected to the distal end 33 of the connector system 32. The proximal end 35 of the connector system 32 is removably connected to a tubing connector 530. The tubing connection 530 is connected to tubing 532 to an opposing end of the tubing connection 530. Similar to the connection of the connector system 32 to the syringe 12 described above, the connector system 32 is removably connected to the tubing connection 530 by the user grasping the connector assembly 32 by the gripping tab 119 and moving the connector assembly 32 toward the tubing connection 530 until the locking arms 100 may be brought into engagement with a lip 534 on the tubing connection 530. The lip 534 is provided on a distal end of the tubing connection 530 and extends circumferentially around the tubing connection 530. Continued movement of the connector assembly 32 in a proximal direction causes the locking arms 100 to spread apart in a radially outward direction relative to the body 52 to allow the locking elements 104 to clear the lip 534. Once the locking elements 104 clear the lip 534, the locking arms 100 move radially inward such that the locking elements 104 engage the tubing connection 530 below the lip 534. During engagement between the locking elements 104 and the lip 534 of the tubing connection 530, the fluid fitting 54 on the connector assembly 32 is brought in fluid communication with the a passageway (not shown) defined in the tubing connection 530 to permit fluid flow between the tubing 50, 532. In some aspects, the connector assembly 32 may be connected with the tubing connection 530 upon application of a proximally-directed force of approximately 5-35 pounds. In other aspects, the force needed to connect the connector assembly 32 with the tubing connection 530 may be more or less than 5-35 pounds. In some aspects, the force needed to connect the connector assembly 32 with the tubing connection 530 is chosen such that the connector assembly 32 is pushed by the user into engagement with the tubing connection 530 such that a fluid-tight connection is established between the passageway of the tubing connection 530 and the fluid fitting 54 of the connector assembly 32. The connection between the connector assembly 32 and the tubing connection 530 may be formed without rotating the connector assembly 32 relative to the tubing connection 530. In other aspects, however, the tubing connection 530 may include tabs 536 that allow for rotation of the tubing connection 530 by the user.

Figure 82:
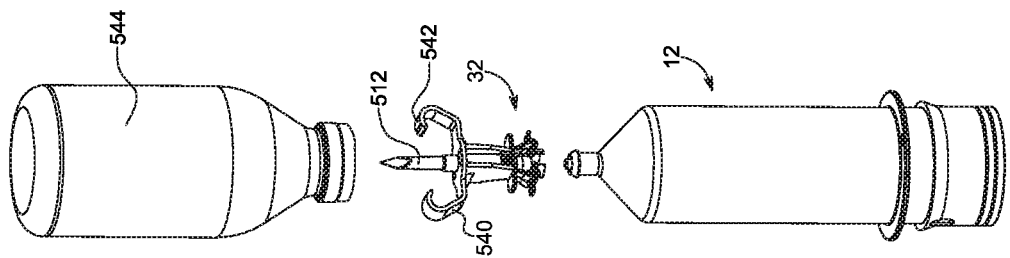
FIG. 82 is a front perspective view of the syringe, the connector system, and the fluid container of FIG. 81 disconnected from one another.
Figure 81:
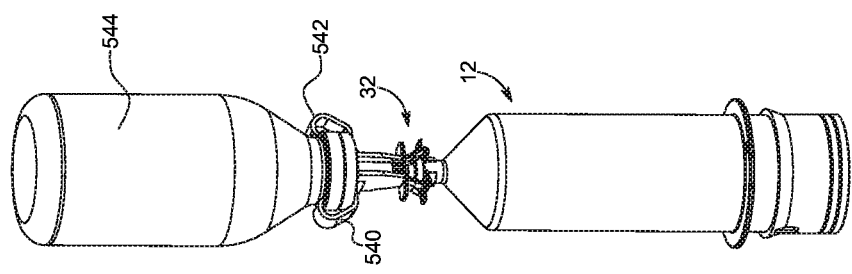
FIG. 81 is a front perspective view of a syringe, a connector system, and a fluid container in accordance with another aspect.

With reference to FIGS. 81-82, a use of the connector assembly 32 of FIGS. 77-78 is described. The connector system 32 shown in FIGS. 81-82 is substantially the same as the connector system 32 of FIGS. 77-78, but also includes a pair of latching arms 540, 542 that extend from the flange 518. The latching arms 540, 542 are formed integral with the flange 518, but may be separately attached to the flange 518 using an adhesive, a welded connection, or a fastening arrangement. The latching arms 540, 542 are generally hook-shaped and are configured to latch on to a fluid container 544 to transfer fluid from the fluid container 544 to the syringe 12. The latching arms 540, 542 are deflectable radially outwards to latch on to the fluid container 544. Using the connector system 32, the syringe 12 is fluidly connected to the fluid container 544. The proximal end of the connector system 32 is connected to the syringe 12 as described above. The opposing end of the connector system 32 is connected to the fluid container 544 by first piercing a septum or seal in the fluid container 544 with the spike 512. The connector system 32 is then moved in a distal direction to further insert the spike 512 into the fluid container 544, while creating contact between the fluid container 544 and the latching arms 540, 542. As the connector system 32 continues to be moved in a distal direction, the fluid container 544 moves the latching arms 540, 542 outwardly in a radial direction. After the cap of the fluid container 544 has moved past the latching arms 540, 542, the latching arms 540, 542 move radially inward to engage the fluid container 544. It is also contemplated that the user may move the latching arms 540, 542 radially outwards during connection of the connector system 32 to the fluid container 544.

It is also contemplated that the connector systems described above may be used to attach other different injector system parts to the syringe nozzles.

While several aspects of syringes, connectors, adapters, and systems and methods of connection for use in medical fluid delivery systems are shown in the accompanying figures and described hereinabove in detail, other aspects will be apparent to, and readily made by, those skilled in the art without departing from the scope and spirit of the disclosure. For example, it is to be understood that this disclosure contemplates that, to the extent possible, one or more features of any aspect can be combined with one or more features of any other aspect. Accordingly, the foregoing description is intended to be illustrative rather than restrictive.

We claim:

1. A connector assembly comprising:
 a body having a proximal end and a distal end spaced apart along a longitudinal axis and a fluid fitting at the proximal end of the body, wherein the fluid fitting is configured for releasably engaging a syringe nozzle;
 a passageway defined by and extending through the body and the fluid fitting, wherein the passageway has an inner surface with a radiused distal end that transitions into a substantially linear proximal end and wherein the substantially linear proximal end of the passageway has a taper having an angle (B) that is larger than an angle (A) of a taper of an inner member of the syringe nozzle;
 at least one deflectable locking arm having a distal end connected to the body and a proximal end, wherein the proximal end of the at least one deflectable locking arm is configured for deflecting in a radially outward direction from the body to releasably engage an engagement portion of the syringe nozzle; and
 at least one locking element disposed on at least a portion of the at least one deflectable locking arm, the at least one locking element movable with movement of the at least one deflectable locking arm between a first position where the at least one locking element is disengaged from the engagement portion of the syringe nozzle and a second position where the at least one locking element is engaged with the engagement portion of the syringe nozzle and the passageway is in fluid communication with the syringe nozzle.

2. The connector assembly of claim 1, further comprising at least one releasing tab provided on the at least one deflectable locking arm to assist in deflecting the proximal end of the at least one deflectable locking arm in the radial direction relative to the distal end of the at least one deflectable locking arm.

3. The connector assembly of claim 1, further comprising at least one gripping tab on the body for gripping the connector assembly.

4. The connector assembly of claim 1, wherein the at least one deflectable locking arm comprises two deflectable locking arms provided on opposing sides of the longitudinal axis of the body, and
 wherein the proximal end of each of the two deflectable locking arms are movable apart from one another to move the at least one locking element of each of the two deflectable locking arms radially outward relative to the longitudinal axis of the body.

5. The connector assembly of claim 1, further comprising a protective skirt provided at the proximal end of the at least one deflectable locking arm,
 wherein the protective skirt is shaped to surround at least a portion of the syringe nozzle when the connector assembly is engaged with the syringe nozzle.

6. The connector assembly of claim 1, further comprising an opposing fitting provided at the distal end of the body for connecting to tubing of a tube set.

7. The connector assembly of claim 1, wherein the at least one deflectable locking arm is deflected radially outward by a lip on the engagement portion of the syringe nozzle upon pressing the connector assembly against the lip to releasably engage the at least one locking element with the engagement portion of the syringe nozzle.

8. The connector assembly of claim 1, further comprising a piercing member extending from a distal end of the body, wherein the piercing member is in fluid communication with the passageway.

9. The connector assembly of claim 1, further comprising a tubing manifold provided on a distal end of the connector assembly.

10. The connector assembly of claim 2, wherein the at least one deflectable locking arm disengages the engagement portion of the syringe nozzle by a user deflecting the proximal end of the at least one deflectable locking arm in the radially outward direction relative to the body using the at least one releasing tab.

11. A syringe and connector system for use in a medical injection procedure, the syringe and connector system comprising:
    a syringe having a proximal end and a distal end with a syringe nozzle on the distal end; and
    a connector assembly configured for releasably engaging the syringe nozzle, the connector assembly comprising:
    a body having a proximal end and a distal end spaced apart along a longitudinal axis and a fluid fitting at the proximal end of the body, wherein the fluid fitting is configured for releasably engaging the syringe nozzle;
    a passageway defined by and extending through the body and the fluid fitting, wherein the passageway has an inner surface with a radiused distal end that transitions into a substantially linear proximal end and wherein the substantially linear proximal end of the passageway has a taper having an angle (B) that is larger than an angle (A) of a taper of an inner member of the syringe nozzle;
    at least one deflectable locking arm having a distal end connected to the body and a proximal end, wherein the proximal end of the at least one deflectable locking arm is configured for deflecting in a radially outward direction from the body to releasably engage an engagement portion of the syringe nozzle; and
    at least one locking element disposed on at least a portion of the at least one deflectable locking arm, the at least one locking element movable with movement of the at least one deflectable locking arm between a first position where the at least one locking element is disengaged from the engagement portion of the syringe nozzle and a second position where the at least one locking element is engaged with the engagement portion of the syringe nozzle and the passageway is in fluid communication with the syringe nozzle.

12. The syringe and connector system of claim 11, further comprising at least one releasing tab provided on the at least one deflectable locking arm to assist in deflecting the proximal end of the at least one deflectable locking arm in the radial direction relative to the distal end.

13. The syringe and connector system of claim 11, further comprising at least one gripping tab on the body for gripping the connector assembly.

14. The syringe and connector system of claim 11, wherein the at least one deflectable locking arm comprises two deflectable locking arms provided on opposing sides of the longitudinal axis of the body, and
    wherein the proximal end of each of the two deflectable locking arms are movable apart from one another to move the at least one locking element of each of the two deflectable locking arms radially outward relative to the longitudinal axis of the body.

15. The syringe and connector system of claim 11, further comprising a protective skirt provided at the proximal end of the at least one deflectable locking arm,
    wherein the protective skirt is shaped to surround at least a portion of the syringe nozzle when the connector assembly is engaged with the syringe nozzle.

16. The syringe and connector system of claim 11, further comprising an opposing fitting provided at the distal end of the body for connecting to tubing of a tube set.

17. The syringe and connector system of claim 11, wherein the at least one deflectable locking arm is deflected radially outward by a lip on the engagement portion of the syringe nozzle upon pressing the connector assembly against the lip to releasably engage the at least one locking element with the engagement portion of the syringe nozzle.

18. The syringe and connector system of claim 11, wherein the syringe nozzle comprises:
    a fluid channel through the inner member, wherein the fluid channel is in fluid communication with an interior volume of the syringe; and
    an outer annular skirt spaced apart from the inner member by an annular space,
    wherein the engagement portion of the syringe nozzle is located on a radially outer surface of the outer annular skirt.

19. The syringe and connector system of claim 11, further comprising a tubing manifold provided on a distal end of the connector assembly.

20. The syringe and connector system of claim 12, wherein the at least one deflectable locking arm disengages the engagement portion of the syringe nozzle by a user deflecting the proximal end of the at least one deflectable locking arm in the radially outward direction relative to the body using the at least one releasing tab.

* * * * *